US012729236B2

(12) United States Patent
Jackson et al.

(10) Patent No.: US 12,729,236 B2
(45) Date of Patent: Sep. 8, 2026

(54) HYDROPHILIC LINKERS FOR ANTIBODY OR DARPIN CONJUGATES

(71) Applicant: Valitor, Inc., Berkeley, CA (US)

(72) Inventors: Wesley M. Jackson, Berkley, CA (US); Amy A. Twite, Berkeley, CA (US); Livia Wilz Brier, Berkeley, CA (US)

(73) Assignee: VALITOR, INC., Berkeley, CA (US)

(*) Notice: Subject to any disclaimer, the term of this patent is extended or adjusted under 35 U.S.C. 154(b) by 1145 days.

(21) Appl. No.: 17/622,467

(22) PCT Filed: Jul. 1, 2020

(86) PCT No.: PCT/US2020/040430

§ 371 (c)(1),
(2) Date: Dec. 23, 2021

(87) PCT Pub. No.: WO2021/003223

PCT Pub. Date: Jan. 7, 2021

(65) Prior Publication Data

US 2022/0251185 A1 Aug. 11, 2022

Related U.S. Application Data

(60) Provisional application No. 62/869,233, filed on Jul. 1, 2019, provisional application No. 62/898,967, filed on Sep. 11, 2019.

(51) Int. Cl.

| | |
|---|---|
| ***C07K 16/24*** | (2006.01) |
| ***A61K 9/00*** | (2006.01) |
| ***A61K 39/00*** | (2006.01) |
| ***A61K 47/61*** | (2017.01) |
| ***A61P 29/00*** | (2006.01) |
| ***A61P 35/00*** | (2006.01) |

(52) U.S. Cl.

CPC .......... *C07K 16/241* (2013.01); *A61K 9/0019* (2013.01); *A61K 47/61* (2017.08); *A61P 29/00* (2018.01); *A61P 35/00* (2018.01); *A61K 39/00* (2013.01); *C07K 2317/94* (2013.01); *C07K 2319/31* (2013.01)

(58) Field of Classification Search

CPC .............. C07K 16/241; C07K 2319/31; A61K 9/0019; A61K 47/61; A61K 39/00; A61K 38/00; A61K 2039/6093; A61P 29/00; A61P 35/00

See application file for complete search history.

(56) References Cited

U.S. PATENT DOCUMENTS

| | | | |
|---|---|---|---|
| 5,162,218 | A | 11/1992 | Schultz |
| 6,781,030 | B1 | 8/2004 | Baguisi et al. |
| 6,964,859 | B2 | 11/2005 | Rajbhandary et al. |
| 7,122,636 | B1 | 10/2006 | Hsei et al. |
| 8,591,885 | B2 | 11/2013 | Chang et al. |
| 8,759,322 | B2 | 6/2014 | Akiyoshi et al. |
| 9,034,624 | B2 | 5/2015 | D'Este et al. |
| 9,221,893 | B2 | 12/2015 | Hahn et al. |
| 9,428,561 | B2 | 8/2016 | Healy et al. |
| 9,925,237 | B2 | 3/2018 | Healy et al. |
| 10,350,267 | B2 | 7/2019 | Healy et al. |
| 10,485,882 | B2 | 11/2019 | Santamaria |
| 10,653,621 | B2 | 5/2020 | Wu et al. |
| 10,765,759 | B2 | 9/2020 | Healy et al. |
| 10,787,490 | B2 | 9/2020 | Bhandari et al. |
| 10,899,828 | B2 | 1/2021 | Koenig et al. |
| 10,941,182 | B2 | 3/2021 | Holder et al. |
| 11,111,291 | B2 | 9/2021 | Famili et al. |
| 11,229,709 | B2 | 1/2022 | Hammond et al. |
| 11,291,707 | B2 | 4/2022 | Healy et al. |
| 11,553,879 | B2 | 1/2023 | Bremer |
| 11,723,982 | B2 | 8/2023 | Healy et al. |
| 2003/0003048 | A1 | 1/2003 | Li et al. |
| 2003/0236214 | A1 | 12/2003 | Wolff et al. |
| 2004/0038876 | A1 | 2/2004 | Pepinsky et al. |
| 2004/0116348 | A1 | 6/2004 | Chau et al. |
| 2005/0025752 | A1 | 2/2005 | Kutryk et al. |
| 2005/0260651 | A1 | 11/2005 | Calias et al. |
| 2005/0282747 | A1 | 12/2005 | Clark et al. |

(Continued)

FOREIGN PATENT DOCUMENTS

| | | | |
|---|---|---|---|
| WO | 0045848 | A1 | 8/2000 |
| WO | 03031581 | A1 | 4/2003 |

(Continued)

OTHER PUBLICATIONS

Ahmad, R., El Mabrouk, M., Sylvester, J., & Zafarullah, M. (2009). Human osteoarthritic chondrocytes are impaired in matrix metalloproteinase-13 inhibition by IFN-γ due to reduced IFN-γ receptor levels. *Osteoarthritis and Cartilage*, 17(8), 1049-1055.

(Continued)

*Primary Examiner* — Elly-Gerald Stoica

(74) *Attorney, Agent, or Firm* — Mintz Levin Cohn Ferris Glovsky and Popeo, P.C.

(57) ABSTRACT

The present disclosure is directed to peptide-polymer conjugates utilizing hydrophilic linkers, and their use in treating diseases or disorders. In one embodiment, the present invention provides a conjugate of Formula I: (X—Y)n-Z Formula (I) wherein each X is independently a peptide having a molecular weight of from about 5 kDa to about 200 kDa; each Y is independently a hydrophilic linker; Z is a biocompatible polymer having a molecular weight of from about 0.1 MDa to about 3 MDa; and subscript n is an integer from 10 to 1000.

18 Claims, 14 Drawing Sheets

Specification includes a Sequence Listing.

(56) References Cited

U.S. PATENT DOCUMENTS

2006/0034833 A1 2/2006 Beirnaert
2006/0034846 A1 2/2006 Ezban et al.
2006/0094643 A1 5/2006 Svirkin et al.
2006/0171920 A1 8/2006 Shechter et al.
2006/0246523 A1 11/2006 Bieniarz et al.
2007/0026518 A1 2/2007 Healy et al.
2008/0113935 A1 5/2008 Yedgar et al.
2008/0268051 A1 10/2008 Hughes et al.
2010/0104585 A1 4/2010 Kiessling et al.
2010/0210509 A1 8/2010 Oh et al.
2011/0046038 A1 2/2011 Healy et al.
2011/0053865 A1 3/2011 Sauders
2011/0111035 A1 5/2011 Washburn et al.
2012/0014975 A1 1/2012 Hegen et al.
2012/0282211 A1 11/2012 Washburn et al.
2014/0038892 A1 2/2014 Yayon et al.
2015/0030626 A1 1/2015 Pietersz et al.
2015/0110782 A1 4/2015 Silence et al.
2016/0158270 A1 6/2016 Singh et al.
2017/0112899 A1 4/2017 Healy et al.
2018/0293360 A1 10/2018 Kelley et al.
2018/0318431 A1 11/2018 Healy et al.
2018/0325999 A1 11/2018 Healy et al.
2019/0142953 A1 5/2019 Edelman et al.
2019/0216945 A1 7/2019 Yang et al.
2020/0085910 A1 3/2020 Healy et al.
2020/0095340 A1 3/2020 Wesche et al.
2020/0384130 A1 12/2020 Detappe et al.
2021/0046181 A1 2/2021 Jackson et al.
2021/0113655 A1 4/2021 Healy et al.
2021/0113702 A1 4/2021 Healy et al.
2022/0265763 A1 8/2022 Healy et al.
2024/0148882 A1 5/2024 Healy et al.

FOREIGN PATENT DOCUMENTS

WO 2005054860 A1 6/2005
WO 2005110489 A2 11/2005
WO 2009120893 A2 10/2009
WO 2011039370 7/2011
WO 2012028716 3/2012
WO WO2016147031 * 9/2016
WO 2017100470 A1 6/2017
WO WO2017196986 * 11/2017 ............ A61K 47/56
WO 2019173777 A1 9/2019
WO 2023183786 9/2023
WO 2023201335 A2 10/2023
WO 2023201336 A2 10/2023
WO 2023201337 10/2023

OTHER PUBLICATIONS

Jha et al., "Perlecan domain I-conjugated, hyaluronic acid-based hydrogel particles for enhanced chondrogenic differentiation via BMP-2 release", Biomaterials, 2009, 30(36), 6964-6975.

Magalhães et al. "Methods of Endotoxin Removal from Biological Preparations: a Review." J. Pharm. Pharmaceut. Sci., 2007, pp. 388-404.

Schneier et al. "Current technologies to endotoxin detection and removal for biopharmaceutical purification," Biotechnology and Bioengineering, Apr. 25, 2020, 117(8), pp. 2588-2609.

Sweander et al., "Filtration Removal of Endotoxin (Pyrogens) in Solution in Different States of Aggregation," Applied and Environmental Microbiology, Oct. 1977, 34(4), pp. 382-385.

Washburn et al. Polymer-conjuugated inhibitors of tumor necrosis factor-a for local control of inflammation., Biomatter, Jul. 10, 2013, vol. 3, No. 3. Article e25597, p. 1-7, Fig 2A.

Westacott et al., "Tumor necrosis factor alpha can contribute to focal loss of cartilage in osteoarthritis," *Osteoarthritis and Cartilage*, 8(3), 213-221 (2000).

International Search Report & Written Opinion of PCT/US2023/64741 mailed Aug. 28, 2023, 11 pages.

International Search Report & Written Opinion of PCT/US2023/65779 mailed Oct. 6, 2023, 12 pages.

International Search Report and Written Opinion for Application No. PCT/US2020/040430, Mailed on Oct. 1, 2020, 10 pages.

International Search Report and Written Opinion for International PCT Application No. PCT/US2019/021460, mailed on May 24, 2019, 11 pages.

International Search Report and Written Opinion received for PCT Application No. PCT/US2009/038446, mailed on Dec. 14, 2009, 10 pages.

International Search Report and Written Opinion received for PCT Application No. PCT/US2016/065653, mailed on Feb. 24, 2017, 10 pages.

Al-Muhammed et al. (1996) "In-Vivo Studies on Dexamethasone Sodium Phosphate Liposomes", Journal of Microencapsulation, 13(3):293-306.

Altiok et al. (Jul. 2016) "Multivalent Hyaluronic Acid Bioconjugates Improve sFlt-1 Activity in Vitro", Biomaterials, 93:95-105(27 pages).

Altiok Eda I. (Oct. 2015) "Improving Anti-VEGF Drugs in the Vitreous", Dissertation, UC Berkeley, 94 pages.

Aoyagi et al. (1999) "Peptide Drug Carrier: Studies on Incorporation of Vasopressin into Nano-associates Comprising Poly(ethylene glycol)-poly (L-aspartic acid) Block Copolymer", Colloids and Surfaces B: Biointerfaces, 16(1-4):237-242.

Arpicco et al. (2002) "Novel Poly(ethylene glycol) Derivatives for Preparation of Ribosome-Inactivating Protein Conjugates", Bioconjugate Chemistry, 13(4):757-765.

Cairo et al. (Feb. 2, 2002) "Control of Multivalent Interactions by Binding Epitope Density", Journal of the American Chemical Society, 124(8):1615-1619.

Chen et al. (1997) "Mitogenic Activities of Water-Soluble and-Insoluble Insulin Conjugates", Bioconjugate Chemistry, 8(2):106-110.

Chonn et al. (1995) "Recent Advances in Liposomal Drug-Delivery Systems", Current Opinion in Biotechnology, 6(6):698-708.

Eyles et al. (Jul. 1997) "Oral Delivery and Fate of Poly(Lactic Acid) Microsphere-Encapsulated Interferon in Rats", Journal of Pharmacy and Pharmacology, 49(7):669-674.

Gao et al. (Jun. 1995) "Controlled Release of a Contraceptive Steroid from Biodegradable and Injectable Gel Formulations: In Vitro Evaluation", Pharmaceutical Research, 12(6):857-863.

Gestwicki et al. (2002) "Influencing Receptor-Ligand Binding Mechanisms with Multivalent Ligand Architecture", Journal of the American Chemical Society, 124(50):14922-14933.

Glass et al. (Jun. 1996) "Characterization of a Hyaluronic Acid-Arg-Gly-Asp Peptide Cell Attachment Matrix", Biomaterials, 17(11):1101-1108.

Itoda et al. (2003) "Evaluation of the Molecular Recognition of Peptide-Conjugated Polymer", Analytical Sciences, 19(1):185-187.

Line et al. (Sep. 2005) "Targeting Tumor Angiogenesis: Comparison of Peptide and Polymer-Peptide Conjugates", Journal of Nuclear Medicine, 46(9):1552-1560.

Mammen et al. (1998) "Polyvalent Interactions in Biological Systems: Implications for Design and Use of Multivalent Ligands and Inhibitors", Angewandte Chemie International Edition, 37(20):2754-2794.

Merrifield Robert B. (Jul. 20, 1963) "Solid Phase Peptide Synthesis. I. The Synthesis of a Tetrapeptide", Journal of the American Chemical Society, 85(14):2149-2154.

Minto et al. (Apr. 1, 1997) "Pharmacokinetics and Pharmacodynamics of Nandrolone Esters in Oil Vehicle: Effects of Ester, Injection Site and Injection Volume", The Journal of Pharmacology and Experimental Therapeutics, 281(1):93-102.

Mitra et al. (2006) "Polymer-Peptide Conjugates for Angiogenesis Targeted Tumor Radiotherapy", Nuclear Medicine and Biology, 33:43-52.

Morgen et al. (2013) "Nanoparticles for Improved Local Retention after Intra-Articular Injection into the Knee Joint", Pharmaceutical Research, 30:257-268.

Ostro et al. (1989) "Use of Liposomes as Injectable-Drug Delivery Systems", American Journal of Health-System Pharmacy, 46(8):1576-1587.

(56) References Cited

OTHER PUBLICATIONS

Payne et al. (Apr. 2012) "Expression of Recombinant Canine sFlt1 as an Experimental Anti-angiogenic Agent", The FASEB Journal, 26(1):2 pages.
Presle et al. (1999) "Cartilage Protection by Nitric Oxide Synthase Inhibitors After Intraarticular Injection of Interleukin-1 Beta in Rats", Arthritis & Rheumatology, 42(10):2094-2102.
Rao K. Paduranga, (1995) "Recent Developments of Collagen-Based Materials for Medical Applications and Drug Delivery Systems", Journal of Biomaterials Science, Polymer Edition, 7(7):623-645.
Shahangian et al. (Mar. 2015) "A Conformation-Based Phage-Display Panning to Screen Neutralizing Anti-VEGF VHHs with VEGFR2 Mimicry Behavior", International Journal of Biological Macromolecules, 77:222-234.
Smith et al. (2003) "Conjugation of Arginine—Glycine—Aspartic Acid Peptides to Thermoreversible N-Isopropylacrylamide Polymers", Journal of Polymer Science: Part A: Polymer Chemistry, 41(24):3989-4000.
Urech et al. (2010) "Anti-inflammatory and Cartilage-protecting Effects of an Intra-articularly Injected Anti-TNFα Single-chain Fv Antibody (ESBA 105) Designed for Local Therapeutic Use", Annals of the Rheumatic Diseases, 69(2):443-449.
Wall et al. (Apr. 2008) "Multivalency of Sonic Hedgehog Conjugated to Linear Polymer Chains Modulates Protein Potency", Bioconjugate Chemistry, 19(4):806-812.
Yu et al. (2015) "Injectable Chemically Crosslinked Hydrogel for the Controlled Release of Bevacizumab in Vitreous: A 6-Month In Vivo Study", Translational Vision Science and Technology, Article 5, 4(2):11 pages.

* cited by examiner

C8 mAb RP HPLC intermediates 40 (EMCH) and 41 (MP2H) 230 nm traces

Lower MP2H retention time indicates lower hydrophobicity

FIG. 9
Avastin MVP PAGE analysis, no sample heating High EDC MVPs
A. 6 µg purified 200525 9500 equivalents EDC EMCH Avastin MVP
   - 122 maleimides
B. 6 µg pure 200527 9500 equivalents EDC MP2H Avastin MVP reaction
   - 95 maleimides
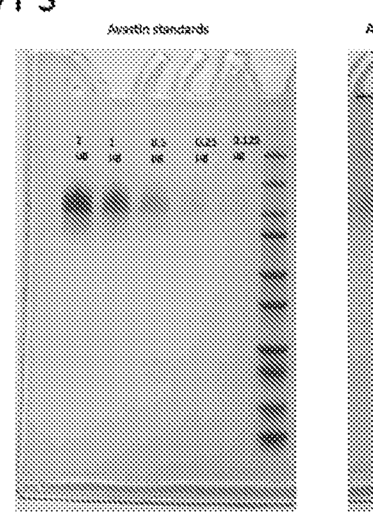
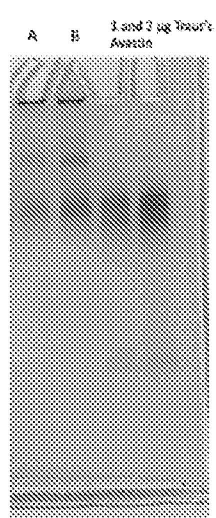
FIG. 10
Goat anti human IgG MVP PAGE with sample heating
- A: Ladder
- B: goat anti-human IgG MVP
- MP2H high EDC intermediate
  - 95 valency
- Antibody valency = 5
- Reaction efficiency = 42%
  - Maleimide in excess
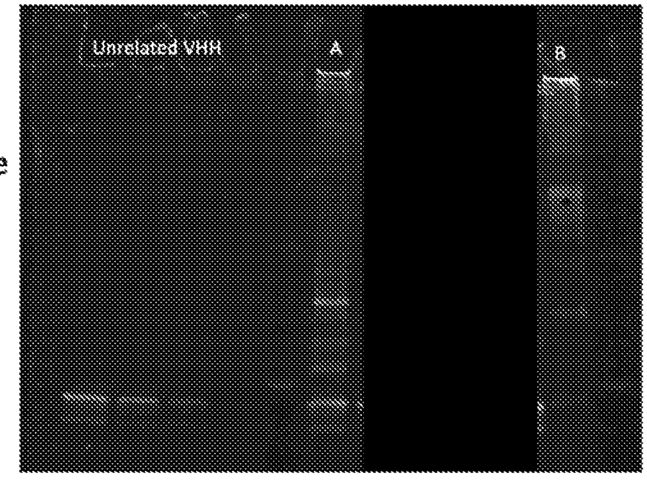

Purified Conjugate 24 (MP2H) and 25 (EMCH) anti-VEGF G5-1 VHH conjugates 280 nm SEC trace DARPin conjugates 30 and 31 SEC traces 280 nm EMCH conjugate showed lower reaction efficiency,
higher percentage of unreacted DARPin, and smaller MVP size by SEC FIG. 13
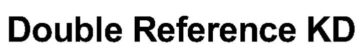
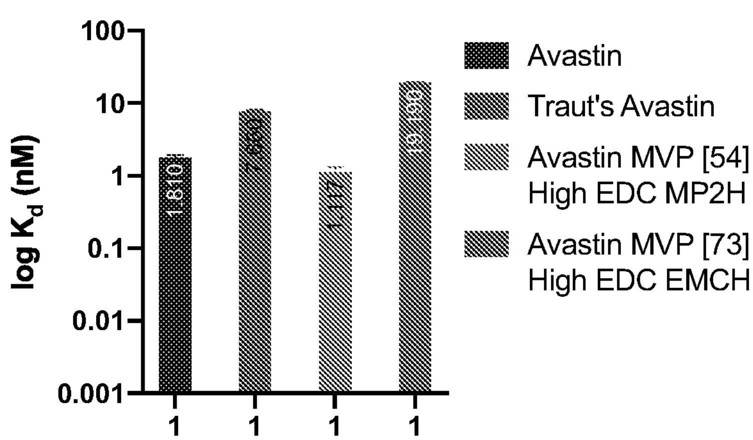
FIG. 14
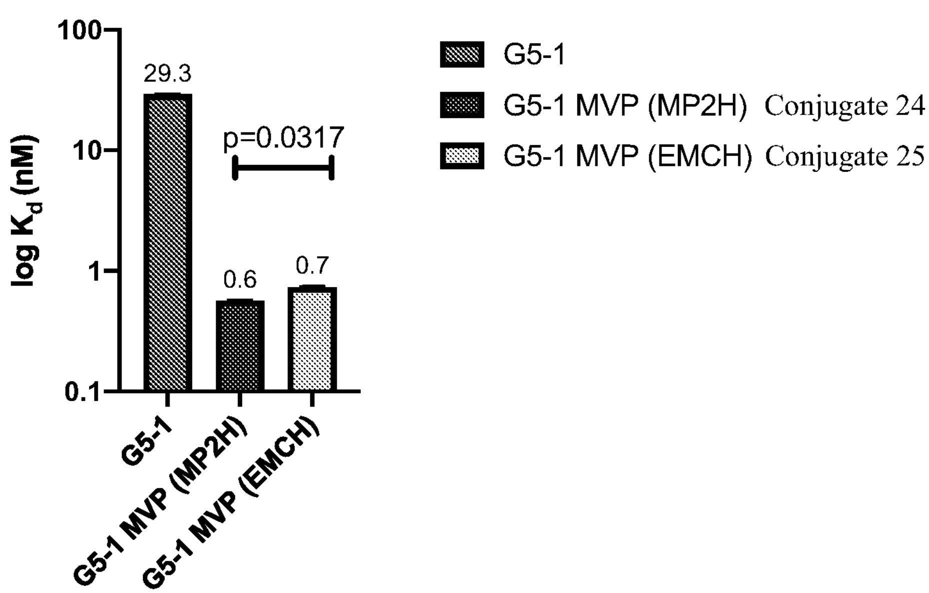

FIG. 18A

Purified 2 kDa natriuretic peptide (NP) polymer conjugate PAGE

A. EMCH NP conjugate synthesized with 0.5 equivalents TCEP

B. MP2H NP conjugate

C. MP2H NP conjugate synthesized with 0.5 equivalents TCEP

D. EMCH NP conjugate

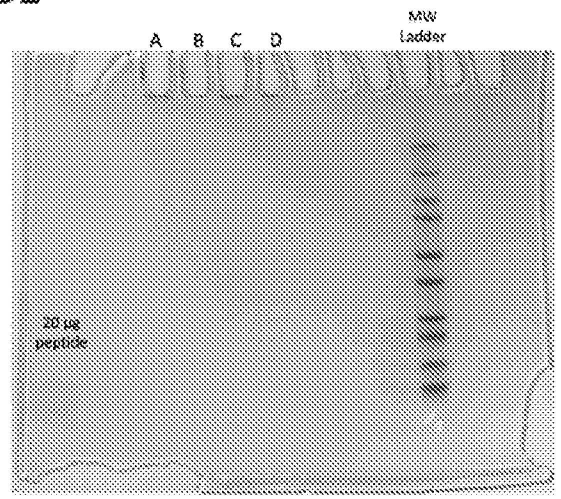

FIG. 18B

Purified 2 kDa natriuretic peptide (NP) polymer conjugate PAGE-heated sample

A. EMCH NP conjugate synthesized with 0.5 equivalents TCEP

B. MP2H NP conjugate

C. MP2H NP conjugate synthesized with 0.5 equivalents TCEP

D. EMCH NP conjugate

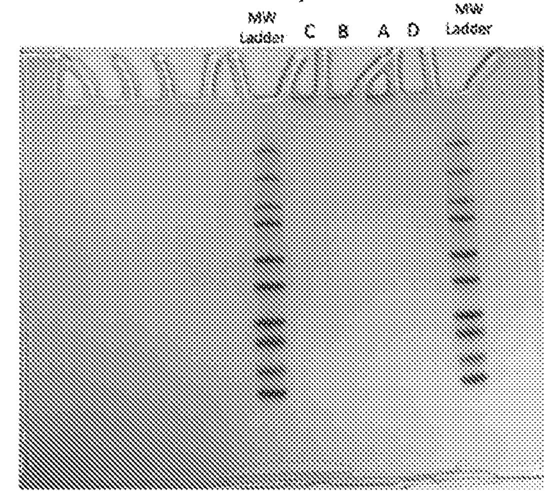

SEQ ID NO:18 anti-VEGF VHH E1-1

SEQ ID NO:19 anti-VEGF VHH G5-1

SEQUENCE LISTING

```
<160> NUMBER OF SEQ ID NOS: 21

<210> SEQ ID NO 1
<211> LENGTH: 129
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-TNFa single-domain heavy chain (VHH)
      antibody

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asp His
            20                  25                  30

Ser Gly Tyr Thr Tyr Thr Ile Gly Trp Phe Arg Gln Ala Pro Gly Lys
        35                  40                  45

Glu Arg Glu Phe Val Ala Arg Ile Tyr Trp Ser Ser Gly Asn Thr Tyr
    50                  55                  60

Tyr Ala Asp Ser Val Lys Gly Arg Phe Ala Ile Ser Arg Asp Ile Ala
65                  70                  75                  80

Lys Asn Thr Val Asp Leu Thr Met Asn Asn Leu Glu Pro Glu Asp Thr
                85                  90                  95

Ala Val Tyr Tyr Cys Ala Ala Arg Asp Gly Ile Pro Thr Ser Arg Ser
            100                 105                 110

Val Glu Ser Tyr Asn Tyr Trp Gly Gln Gly Thr Gln Val Thr Val Ser
        115                 120                 125

Ser


<210> SEQ ID NO 2
<211> LENGTH: 149
```

<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-TNFa single-domain heavy chain (VHH) antibody

<400> SEQUENCE: 2

```
Ser Asn Ala Gln Val Gln Leu Gln Glu Ser Gly Gly Gly Leu Val Gln
1               5                   10                  15

Pro Gly Gly Ser Leu Arg Leu Ser Cys Ala Ala Ser Gly Arg Thr Phe
            20                  25                  30

Ser Asp His Ser Gly Tyr Thr Tyr Thr Ile Gly Trp Phe Arg Gln Ala
        35                  40                  45

Pro Gly Lys Glu Arg Glu Phe Val Ala Arg Ile Tyr Trp Ser Ser Gly
    50                  55                  60

Asn Thr Tyr Tyr Ala Asp Ser Val Lys Gly Arg Phe Ala Ile Ser Arg
65                  70                  75                  80

Asp Ile Ala Lys Asn Thr Val Asp Leu Thr Met Asn Asn Leu Glu Pro
                85                  90                  95

Glu Asp Thr Ala Val Tyr Tyr Cys Ala Ala Arg Asp Gly Ile Pro Thr
            100                 105                 110

Ser Arg Ser Val Glu Ser Tyr Asn Tyr Trp Gly Gln Gly Thr Gln Val
        115                 120                 125

Thr Val Ser Ser Ser Pro Ser Thr Pro Pro Thr Pro Ser Pro Ser Thr
    130                 135                 140

Pro Pro Gly Gly Cys
145
```

<210> SEQ ID NO 3
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 3

```
Asp His Ser Gly Tyr Thr Tyr Thr Ile Gly
1               5                   10
```

<210> SEQ ID NO 4
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 4

```
Ala Arg Ile Tyr Trp Ser Ser Gly Asn Thr Tyr Tyr Ala Asp Ser Val
1               5                   10                  15

Lys Gly
```

<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

Arg Asp Gly Ile Pro Thr
1 5

<210> SEQ ID NO 6
<211> LENGTH: 65
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-TNFa affibody

<400> SEQUENCE: 6

Ser Asn Ala Cys Gly Gly Gly Val Asp Asn Lys Phe Asn Lys Glu Val
1 5 10 15

Gly Trp Ala Phe Gly Glu Ile Gly Ala Leu Pro Asn Leu Asn Ala Leu
20 25 30

Gln Phe Arg Ala Phe Ile Ile Ser Leu Trp Asp Asp Pro Ser Gln Ser
35 40 45

Ala Asn Leu Leu Ala Glu Ala Lys Lys Leu Asn Asp Ala Gln Ala Pro
50 55 60

Lys
65

<210> SEQ ID NO 7
<211> LENGTH: 168
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-TNFa single-domain heavy chain (VHH) antibody

<400> SEQUENCE: 7

Ser Asn Ala Gln Val Gln Leu Gln Glu Ser Gly Gly Gly Leu Val Gln
1 5 10 15

Pro Gly Gly Ser Leu Arg Leu Ser Cys Ala Ala Ser Gly Arg Thr Phe
20 25 30

Ser Asp His Ser Gly Tyr Thr Tyr Thr Ile Gly Trp Phe Arg Gln Ala
35 40 45

Pro Gly Lys Glu Arg Glu Phe Val Ala Arg Ile Tyr Trp Ser Ser Gly
50 55 60

Asn Thr Tyr Tyr Ala Asp Ser Val Lys Gly Arg Phe Ala Ile Ser Arg
65 70 75 80

Asp Ile Ala Lys Asn Thr Val Asp Leu Thr Met Asn Asn Leu Glu Pro
85 90 95

Glu Asp Thr Ala Val Tyr Tyr Cys Ala Ala Arg Asp Gly Ile Pro Thr
100 105 110

Ser Arg Ser Val Glu Ser Tyr Asn Tyr Trp Gly Gln Gly Thr Gln Val
115 120 125

Thr Val Ser Ser Ser Pro Ser Thr Pro Pro Thr Pro Ser Pro Ser Thr
130 135 140

Pro Pro Gly Gly Cys Asp Asp Asp Asp Lys His His His His His His
145 150 155 160

Asp Tyr Lys Asp Asp Asp Asp Lys
165

-continued

<210> SEQ ID NO 8
<211> LENGTH: 169
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-TNFa designed ankyrin repeat protein (DARPin)

<400> SEQUENCE: 8

Ser Asn Ala Asp Leu Gly Lys Lys Leu Leu Glu Val Ala Arg Ala Gly
1               5                   10                  15

Gln Asp Asp Glu Val Arg Ile Leu Met Ala Asn Gly Ala Asp Val Asn
            20                  25                  30

Ala Ala Asp His Gln Ser Phe Thr Pro Leu His Leu Tyr Ala Ile Phe
        35                  40                  45

Gly His Leu Glu Ile Val Glu Val Leu Leu Lys Asn Gly Ala Asp Val
    50                  55                  60

Asn Ala Ser Asp Trp His Gly Asn Thr Pro Leu His Leu Ala Ala Trp
65                  70                  75                  80

Ile Gly His Leu Glu Ile Val Glu Val Leu Leu Lys Tyr Gly Ala Asp
                85                  90                  95

Val Asn Ala Thr Asp His Ser Gly Ser Thr Pro Leu His Leu Ala Ala
            100                 105                 110

Thr Leu Gly His Leu Glu Ile Val Glu Val Leu Leu Lys Tyr Gly Ala
        115                 120                 125

Asp Val Asn Ala Gln Asp Lys Phe Gly Lys Thr Ala Phe Asp Ile Ser
    130                 135                 140

Ile Asp Asn Gly Asn Glu Asp Leu Ala Glu Ile Leu Gln Lys Ala Ala
145                 150                 155                 160

Gly Gly Gly Ser Gly Gly Gly Ser Cys
                165

<210> SEQ ID NO 9
<211> LENGTH: 268
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-IL-1B single-chain (scFv) antibody

<400> SEQUENCE: 9

Ser Asn Ala Glu Ile Val Met Thr Gln Ser Pro Ser Thr Leu Ser Ala
1               5                   10                  15

Ser Val Gly Asp Arg Val Ile Ile Thr Cys Gln Ala Ser Gln Ser Ile
            20                  25                  30

Asp Asn Trp Leu Ser Trp Tyr Gln Gln Lys Pro Gly Lys Ala Pro Lys
        35                  40                  45

Leu Leu Ile Tyr Arg Ala Ser Thr Leu Ala Ser Gly Val Pro Ser Arg
    50                  55                  60

Phe Ser Gly Ser Gly Ser Gly Ala Glu Phe Thr Leu Thr Ile Ser Ser
65                  70                  75                  80

Leu Gln Pro Asp Asp Phe Ala Thr Tyr Tyr Cys Gln Asn Thr Gly Gly
                85                  90                  95

Gly Val Ser Ile Ala Phe Gly Gln Gly Thr Lys Leu Thr Val Leu Gly
            100                 105                 110

-continued

Gly Gly Gly Gly Ser Gly Gly Gly Gly Ser Gly Gly Gly Gly Ser Gly
115 120 125

Gly Gly Gly Ser Glu Val Gln Leu Val Glu Ser Gly Gly Gly Leu Val
130 135 140

Gln Pro Gly Gly Ser Leu Arg Leu Ser Cys Thr Ala Ser Gly Phe Ser
145 150 155 160

Leu Ser Ser Ala Ala Met Ala Trp Val Arg Gln Ala Pro Gly Lys Gly
165 170 175

Leu Glu Trp Val Gly Ile Ile Tyr Asp Ser Ala Ser Thr Tyr Tyr Ala
180 185 190

Ser Trp Ala Lys Gly Arg Phe Thr Ile Ser Arg Asp Thr Ser Lys Asn
195 200 205

Thr Val Tyr Leu Gln Met Asn Ser Leu Arg Ala Glu Asp Thr Ala Val
210 215 220

Tyr Tyr Cys Ala Arg Glu Arg Ala Ile Phe Ser Gly Asp Phe Val Leu
225 230 235 240

Trp Gly Gln Gly Thr Leu Val Thr Val Ser Ser Ser Pro Ser Thr Pro
245 250 255

Pro Thr Pro Ser Pro Ser Thr Pro Pro Gly Gly Cys
260 265

<210> SEQ ID NO 10
<211> LENGTH: 340
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: soluble interleukin receptor 2 (sILR2)

<400> SEQUENCE: 10

His Thr Gly Ala Ala Arg Ser Cys Arg Phe Arg Gly Arg His Tyr Lys
1 5 10 15

Arg Glu Phe Arg Leu Glu Gly Glu Pro Val Ala Leu Arg Cys Pro Gln
20 25 30

Val Pro Tyr Trp Leu Trp Ala Ser Val Ser Pro Arg Ile Asn Leu Thr
35 40 45

Trp His Lys Asn Asp Ser Ala Arg Thr Val Pro Gly Glu Glu Thr
50 55 60

Arg Met Trp Ala Gln Asp Gly Ala Leu Trp Leu Leu Pro Ala Leu Gln
65 70 75 80

Glu Asp Ser Gly Thr Tyr Val Cys Thr Thr Arg Asn Ala Ser Tyr Cys
85 90 95

Asp Lys Met Ser Ile Glu Leu Arg Val Phe Glu Asn Thr Asp Ala Phe
100 105 110

Leu Pro Phe Ile Ser Tyr Pro Gln Ile Leu Thr Leu Ser Thr Ser Gly
115 120 125

Val Leu Val Cys Pro Asp Leu Ser Glu Phe Thr Arg Asp Lys Thr Asp
130 135 140

Val Lys Ile Gln Trp Tyr Lys Asp Ser Leu Leu Leu Asp Lys Asp Asn
145 150 155 160

Glu Lys Phe Leu Ser Val Arg Gly Thr Thr His Leu Leu Val His Asp
165 170 175

Val Ala Leu Glu Asp Ala Gly Tyr Tyr Arg Cys Val Leu Thr Phe Ala
180 185 190

His Glu Gly Gln Gln Tyr Asn Ile Thr Arg Ser Ile Glu Leu Arg Ile
195 200 205

Lys Lys Lys Lys Glu Glu Thr Ile Pro Val Ile Ile Ser Pro Leu Lys
210 215 220

Thr Ile Ser Ala Ser Leu Gly Ser Arg Leu Thr Ile Pro Cys Lys Val
225 230 235 240

Phe Leu Gly Thr Gly Thr Pro Leu Thr Thr Met Leu Trp Trp Thr Ala
245 250 255

Asn Asp Thr His Ile Glu Ser Ala Tyr Pro Gly Gly Arg Val Thr Glu
260 265 270

Gly Pro Arg Gln Glu Tyr Ser Glu Asn Asn Glu Asn Tyr Ile Glu Val
275 280 285

Pro Leu Ile Phe Asp Pro Val Thr Arg Glu Asp Leu His Met Asp Phe
290 295 300

Lys Cys Val Val His Asn Thr Leu Ser Phe Gln Thr Leu Arg Thr Thr
305 310 315 320

Val Lys Glu Ser Pro Ser Thr Pro Pro Thr Pro Ser Pro Ser Thr Pro
325 330 335

Pro Gly Gly Cys
340

<210> SEQ ID NO 11
<211> LENGTH: 155
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-(mouse) TNFa single-domain heavy-chain (VHH) antibody

<400> SEQUENCE: 11

Ser Asn Ala Gln Val Gln Leu Gln Asp Ser Gly Gly Gly Leu Val Gln
1 5 10 15

Ala Gly Gly Ser Leu Arg Leu Ser Cys Ala Ala Ser Gly Gly Thr Phe
20 25 30

Ser Ser Ile Ile Met Ala Trp Phe Arg Gln Ala Pro Gly Lys Glu Arg
35 40 45

Glu Phe Val Gly Ala Val Ser Trp Ser Gly Gly Thr Thr Val Tyr Ala
50 55 60

Asp Ser Val Leu Gly Arg Phe Glu Ile Ser Arg Asp Ser Ala Arg Lys
65 70 75 80

Ser Val Tyr Leu Gln Met Asn Ser Leu Lys Pro Glu Asp Thr Ala Val
85 90 95

Tyr Tyr Cys Ala Ala Arg Pro Tyr Gln Lys Tyr Asn Trp Ala Ser Ala
100 105 110

Ser Tyr Asn Val Trp Gly Gln Gly Thr Gln Val Thr Val Ser Ser Ser
115 120 125

Pro Ser Thr Pro Pro Thr Pro Ser Pro Ser Thr Pro Pro Gly Gly Cys
130 135 140

Asp Asp Asp Asp Lys His His His His His His
145 150 155

<210> SEQ ID NO 12
<211> LENGTH: 755
<212> TYPE: PRT

<213> ORGANISM: Artificial sequence
<220> FEATURE:
<223> OTHER INFORMATION: Synthetic polypeptide

<400> SEQUENCE: 12

```
Gly Ser Lys Leu Lys Asp Pro Glu Leu Ser Leu Lys Gly Thr Gln His
1               5                   10                  15

Ile Met Gln Ala Gly Gln Thr Leu His Leu Gln Cys Arg Gly Glu Ala
            20                  25                  30

Ala His Lys Trp Ser Leu Pro Glu Met Val Ser Lys Glu Ser Glu Arg
        35                  40                  45

Leu Ser Ile Thr Lys Ser Ala Cys Gly Arg Asn Gly Lys Gln Phe Cys
    50                  55                  60

Ser Thr Leu Thr Leu Asn Thr Ala Gln Ala Asn His Thr Gly Phe Tyr
65                  70                  75                  80

Ser Cys Lys Tyr Leu Ala Val Pro Thr Ser Lys Lys Lys Glu Thr Glu
                85                  90                  95

Ser Ala Ile Tyr Ile Phe Ile Ser Asp Thr Gly Arg Pro Phe Val Glu
            100                 105                 110

Met Tyr Ser Glu Ile Pro Glu Ile Ile His Met Thr Glu Gly Arg Glu
        115                 120                 125

Leu Val Ile Pro Cys Arg Val Thr Ser Pro Asn Ile Thr Val Thr Leu
    130                 135                 140

Lys Lys Phe Pro Leu Asp Thr Leu Ile Pro Asp Gly Lys Arg Ile Ile
145                 150                 155                 160

Trp Asp Ser Arg Lys Gly Phe Ile Ile Ser Asn Ala Thr Tyr Lys Glu
                165                 170                 175

Ile Gly Leu Leu Thr Cys Glu Ala Thr Val Asn Gly His Leu Tyr Lys
            180                 185                 190

Thr Asn Tyr Leu Thr His Arg Gln Thr Asn Thr Ile Ile Asp Val Gln
        195                 200                 205

Ile Ser Thr Pro Arg Pro Val Lys Leu Leu Arg Gly His Thr Leu Val
    210                 215                 220

Leu Asn Cys Thr Ala Thr Thr Pro Leu Asn Thr Arg Val Gln Met Thr
225                 230                 235                 240

Trp Ser Tyr Pro Asp Glu Lys Asn Lys Arg Ala Ser Val Arg Arg Arg
                245                 250                 255

Ile Asp Gln Ser Asn Ser His Ala Asn Ile Phe Tyr Ser Val Leu Thr
            260                 265                 270

Ile Asp Lys Met Gln Asn Lys Asp Lys Gly Leu Tyr Thr Cys Arg Val
        275                 280                 285

Arg Ser Gly Pro Ser Phe Lys Ser Val Asn Thr Ser Val His Ile Tyr
    290                 295                 300

Asp Lys Ala Phe Ile Thr Val Lys His Arg Lys Gln Gln Val Leu Glu
305                 310                 315                 320

Thr Val Ala Gly Lys Arg Ser Tyr Arg Leu Ser Met Lys Val Lys Ala
                325                 330                 335

Phe Pro Ser Pro Glu Val Val Trp Leu Lys Asp Gly Leu Pro Ala Thr
            340                 345                 350

Glu Lys Ser Ala Arg Tyr Leu Thr Arg Gly Tyr Ser Leu Ile Ile Lys
        355                 360                 365

Asp Val Thr Glu Glu Asp Ala Gly Asn Tyr Thr Ile Leu Leu Ser Ile
    370                 375                 380

Lys Gln Ser Asn Val Phe Lys Asn Leu Thr Ala Thr Leu Ile Val Asn
```

-continued

```
385                 390                 395                 400

Val Lys Pro Gln Ile Tyr Glu Lys Ala Val Ser Ser Phe Pro Asp Pro
                405                 410                 415

Ala Leu Tyr Pro Leu Gly Ser Arg Gln Ile Leu Thr Cys Thr Ala Tyr
            420                 425                 430

Gly Ile Pro Gln Pro Thr Ile Lys Trp Phe Trp His Pro Cys Asn His
        435                 440                 445

Asn His Ser Glu Ala Arg Cys Asp Phe Cys Ser Asn Asn Glu Glu Ser
    450                 455                 460

Phe Ile Leu Asp Ala Asp Ser Asn Met Gly Asn Arg Ile Glu Ser Ile
465                 470                 475                 480

Thr Gln Arg Met Ala Ile Ile Glu Gly Lys Asn Lys Met Ala Ser Thr
                485                 490                 495

Leu Val Val Ala Asp Ser Arg Ile Ser Gly Ile Tyr Ile Cys Ile Ala
            500                 505                 510

Ser Asn Lys Val Gly Thr Val Gly Arg Asn Ile Ser Phe Tyr Ile Thr
        515                 520                 525

Asp Val Pro Asn Gly Phe His Val Asn Leu Glu Lys Met Pro Thr Glu
    530                 535                 540

Gly Glu Asp Leu Lys Leu Ser Cys Thr Val Asn Lys Phe Leu Tyr Arg
545                 550                 555                 560

Asp Val Thr Trp Ile Leu Leu Arg Thr Val Asn Asn Arg Thr Met His
                565                 570                 575

Tyr Ser Ile Ser Lys Gln Lys Met Ala Ile Thr Lys Glu His Ser Ile
            580                 585                 590

Thr Leu Asn Leu Thr Ile Met Asn Val Ser Leu Gln Asp Ser Gly Thr
        595                 600                 605

Tyr Ala Cys Arg Ala Arg Asn Val Tyr Thr Gly Glu Glu Ile Leu Gln
    610                 615                 620

Lys Lys Glu Ile Thr Ile Arg Asp Gln Glu Ala Pro Tyr Leu Leu Arg
625                 630                 635                 640

Asn Leu Ser Asp His Thr Val Ala Ile Ser Ser Ser Thr Thr Leu Asp
                645                 650                 655

Cys His Ala Asn Gly Val Pro Glu Pro Gln Ile Thr Trp Phe Lys Asn
            660                 665                 670

Asn His Lys Ile Gln Gln Glu Pro Gly Ile Ile Leu Gly Pro Gly Ser
        675                 680                 685

Ser Thr Leu Phe Ile Glu Arg Val Thr Glu Glu Asp Glu Gly Val Tyr
    690                 695                 700

His Cys Lys Ala Thr Asn Gln Lys Gly Ser Val Glu Ser Ser Ala Tyr
705                 710                 715                 720

Leu Thr Val Gln Gly Thr Ser Asp Lys Ser Asn Leu Glu Leu Ile Thr
                725                 730                 735

Leu Thr Cys Thr Cys Val Ala Ala Thr Leu Phe Trp Leu Leu Leu Thr
            740                 745                 750

Leu Phe Ile
        755
```

<210> SEQ ID NO 13
<211> LENGTH: 303
<212> TYPE: PRT
<213> ORGANISM: Artificial sequence
<220> FEATURE:
<223> OTHER INFORMATION: Synthetic polypeptide

<400> SEQUENCE: 13

Gly Ser Lys Leu Lys Asp Pro Glu Leu Ser Leu Lys Gly Thr Gln His
1 5 10 15

Ile Met Gln Ala Gly Gln Thr Leu His Leu Gln Cys Arg Gly Glu Ala
20 25 30

Ala His Lys Trp Ser Leu Pro Glu Met Val Ser Lys Glu Ser Glu Arg
35 40 45

Leu Ser Ile Thr Lys Ser Ala Cys Gly Arg Asn Gly Lys Gln Phe Cys
50 55 60

Ser Thr Leu Thr Leu Asn Thr Ala Gln Ala Asn His Thr Gly Phe Tyr
65 70 75 80

Ser Cys Lys Tyr Leu Ala Val Pro Thr Ser Lys Lys Lys Glu Thr Glu
85 90 95

Ser Ala Ile Tyr Ile Phe Ile Ser Asp Thr Gly Arg Pro Phe Val Glu
100 105 110

Met Tyr Ser Glu Ile Pro Glu Ile Ile His Met Thr Glu Gly Arg Glu
115 120 125

Leu Val Ile Pro Cys Arg Val Thr Ser Pro Asn Ile Thr Val Thr Leu
130 135 140

Lys Lys Phe Pro Leu Asp Thr Leu Ile Pro Asp Gly Lys Arg Ile Ile
145 150 155 160

Trp Asp Ser Arg Lys Gly Phe Ile Ile Ser Asn Ala Thr Tyr Lys Glu
165 170 175

Ile Gly Leu Leu Thr Cys Glu Ala Thr Val Asn Gly His Leu Tyr Lys
180 185 190

Thr Asn Tyr Leu Thr His Arg Gln Thr Asn Thr Ile Ile Asp Val Gln
195 200 205

Ile Ser Thr Pro Arg Pro Val Lys Leu Leu Arg Gly His Thr Leu Val
210 215 220

Leu Asn Cys Thr Ala Thr Thr Pro Leu Asn Thr Arg Val Gln Met Thr
225 230 235 240

Trp Ser Tyr Pro Asp Glu Lys Asn Lys Arg Ala Ser Val Arg Arg Arg
245 250 255

Ile Asp Gln Ser Asn Ser His Ala Asn Ile Phe Tyr Ser Val Leu Thr
260 265 270

Ile Asp Lys Met Gln Asn Lys Asp Lys Gly Leu Tyr Thr Cys Arg Val
275 280 285

Arg Ser Gly Pro Ser Phe Lys Ser Val Asn Thr Ser Val His Ile
290 295 300

<210> SEQ ID NO 14
<211> LENGTH: 187
<212> TYPE: PRT
<213> ORGANISM: Artificial sequence
<220> FEATURE:
<223> OTHER INFORMATION: Synthetic polypeptide

<400> SEQUENCE: 14

Ile Pro Glu Ile Ile His Met Thr Glu Gly Arg Glu Leu Val Ile Pro
1 5 10 15

Cys Arg Val Thr Ser Pro Asn Ile Thr Val Thr Leu Lys Lys Phe Pro
20 25 30

Leu Asp Thr Leu Ile Pro Asp Gly Lys Arg Ile Ile Trp Asp Ser Arg
35 40 45

Lys Gly Phe Ile Ile Ser Asn Ala Thr Tyr Lys Glu Ile Gly Leu Leu

```
    50                  55                  60

Thr Cys Glu Ala Thr Val Asn Gly His Leu Tyr Lys Thr Asn Tyr Leu
65                  70                  75                  80

Thr His Arg Gln Thr Asn Thr Ile Ile Asp Val Gln Ile Ser Thr Pro
                85                  90                  95

Arg Pro Val Lys Leu Leu Arg Gly His Thr Leu Val Leu Asn Cys Thr
            100                 105                 110

Ala Thr Thr Pro Leu Asn Thr Arg Val Gln Met Thr Trp Ser Tyr Pro
        115                 120                 125

Asp Glu Lys Asn Lys Arg Ala Ser Val Arg Arg Arg Ile Asp Gln Ser
    130                 135                 140

Asn Ser His Ala Asn Ile Phe Tyr Ser Val Leu Thr Ile Asp Lys Met
145                 150                 155                 160

Gln Asn Lys Asp Lys Gly Leu Tyr Thr Cys Arg Val Arg Ser Gly Pro
                165                 170                 175

Ser Phe Lys Ser Val Asn Thr Ser Val His Ile
            180                 185


<210> SEQ ID NO 15
<211> LENGTH: 350
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: sFlt sequence

<400> SEQUENCE: 15

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
```

```
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Cys Asp Asp Asp Asp Lys His His His His His His
            340                 345                 350


<210> SEQ ID NO 16
<211> LENGTH: 280
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: scFv anti-VEGF antibody

<400> SEQUENCE: 16

Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Ile Ile His Ser
            20                  25                  30

Trp Leu Ala Trp Tyr Gln Gln Lys Pro Gly Lys Ala Pro Lys Leu Leu
        35                  40                  45

Ile Tyr Leu Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Val Tyr Leu Ala Ser
                85                  90                  95

Thr Asn Gly Ala Asn Phe Gly Gln Gly Thr Lys Leu Thr Val Leu Gly
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Thr Ala Ser Gly Phe Ser
145                 150                 155                 160

Leu Thr Asp Tyr Tyr Tyr Met Thr Trp Val Arg Gln Ala Pro Gly Lys
                165                 170                 175

Gly Leu Glu Trp Val Gly Phe Ile Asp Pro Asp Asp Asp Pro Tyr Tyr
            180                 185                 190

Ala Thr Trp Ala Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
```

```
    210                 215                 220

Val Tyr Tyr Cys Ala Gly Gly Asp His Asn Ser Gly Trp Gly Leu Asp
225                 230                 235                 240

Ile Trp Gly Gln Gly Thr Leu Val Thr Val Ser Ser Ser Pro Ser Thr
                245                 250                 255

Pro Pro Thr Pro Ser Pro Ser Thr Pro Pro Gly Gly Cys Asp Asp Asp
            260                 265                 270

Asp Lys His His His His His His
        275                 280


<210> SEQ ID NO 17
<211> LENGTH: 156
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-VEGF VHH

<400> SEQUENCE: 17

Ser Asn Ala Asp Val Gln Leu Val Glu Ser Gly Gly Gly Leu Val Gln
1               5                   10                  15

Pro Gly Gly Ser Leu Arg Leu Ser Cys Ala Ala Ser Gly Arg Thr Phe
            20                  25                  30

Ser Ser Tyr Ser Met Gly Trp Phe Arg Gln Ala Pro Gly Lys Glu Arg
        35                  40                  45

Glu Phe Val Val Ala Ile Ser Lys Gly Gly Tyr Lys Tyr Asp Ala Val
    50                  55                  60

Ser Leu Glu Gly Arg Phe Thr Ile Ser Arg Asp Asn Ala Lys Asn Thr
65                  70                  75                  80

Val Tyr Leu Gln Ile Asn Ser Leu Arg Pro Glu Asp Thr Ala Val Tyr
                85                  90                  95

Tyr Cys Ala Ser Ser Arg Ala Tyr Gly Ser Ser Arg Leu Arg Leu Ala
            100                 105                 110

Asp Thr Tyr Glu Tyr Trp Gly Gln Gly Thr Leu Val Thr Val Ser Ser
        115                 120                 125

Ser Pro Ser Thr Pro Pro Thr Pro Ser Pro Ser Thr Pro Pro Gly Gly
    130                 135                 140

Cys Asp Asp Asp Asp Lys His His His His His His
145                 150                 155


<210> SEQ ID NO 18
<211> LENGTH: 136
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-VEGF VHH E1-1

<400> SEQUENCE: 18

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Gly Ser Asp Ala Gly
            20                  25                  30

Thr Met Gly Trp Phe Arg Gln Ala Pro Gly Lys Glu Arg Glu Phe Val
        35                  40                  45
```

```
Ser Ala Ile Ser Trp Ala Gly Thr Ala Trp Arg Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Leu Gly Ser Tyr Glu Met Asp His His Tyr Trp Gly Gln Gly
            100                 105                 110

Thr Gln Val Thr Val Ser Ser Ser Pro Ser Thr Pro Pro Thr Pro Ser
        115                 120                 125

Pro Ser Thr Pro Pro Gly Gly Cys
    130                 135


<210> SEQ ID NO 19
<211> LENGTH: 128
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-VEGF VHH G5-1

<400> SEQUENCE: 19

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Thr Tyr Ala Asn Tyr
            20                  25                  30

Val Met Gly Trp Phe Arg Gln Ala Pro Gly Lys Glu Arg Glu Phe Val
        35                  40                  45

Ser Ala Ile Ser Ala Phe Asn Asp Glu Val Leu Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Arg Ala Gly Gln Glu Glu Ala Ser Lys Asn Ala Pro Gly Gln
            100                 105                 110

Glu Pro Val Arg Tyr Trp Gly Gln Gly Thr Gln Val Thr Val Ser Ser
        115                 120                 125


<210> SEQ ID NO 20
<211> LENGTH: 22
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: natriuretic peptide, C-type
<220> FEATURE:
<221> NAME/KEY: misc_feature
<222> LOCATION: (6)..(22)
<223> OTHER INFORMATION: disulfide bridge

<400> SEQUENCE: 20

Gly Leu Ser Lys Gly Cys Phe Gly Leu Lys Leu Asp Arg Ile Gly Ser
1               5                   10                  15

Met Ser Gly Leu Gly Cys
            20
```

-continued

<210> SEQ ID NO 21
<211> LENGTH: 138
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: anti-VEGF DARPin

<400> SEQUENCE: 21

Ser Asn Ala Gly Ser Asp Leu Asp Lys Lys Leu Leu Glu Ala Ala Arg
1 5 10 15

Ala Gly Gln Asp Asp Glu Val Arg Ile Leu Met Ala Asn Gly Ala Asp
20 25 30

Val Asn Ala Arg Asp Ser Thr Gly Trp Thr Pro Leu His Leu Ala Ala
35 40 45

Pro Trp Gly His Pro Glu Ile Val Glu Val Leu Leu Lys Asn Gly Ala
50 55 60

Asp Val Asn Ala Ala Asp Phe Gln Gly Trp Thr Pro Leu His Leu Ala
65 70 75 80

Ala Ala Val Gly His Leu Glu Ile Val Glu Val Leu Leu Lys Tyr Gly
85 90 95

Ala Asp Val Asn Ala Gln Asp Lys Phe Gly Lys Thr Ala Phe Asp Ile
100 105 110

Ser Ile Asp Asn Gly Asn Glu Asp Leu Ala Glu Ile Leu Gln Lys Ala
115 120 125

Ala Gly Gly Gly Ser Gly Gly Gly Ser Cys
130 135

HYDROPHILIC LINKERS FOR ANTIBODY OR DARPIN CONJUGATES

CROSS-REFERENCES TO RELATED APPLICATIONS

This application is a U.S. National Phase Application of PCT International Application No. PCT/US2020/040430, filed Jul. 1, 2020, which is an International Application of and claims the benefit of U.S. Provisional Application Nos. 62/869,233, filed Jul. 1, 2019, and 62/898,967, filed Sep. 11, 2019, each of which is incorporated herein in its entirety.

STATEMENT REGARDING SEQUENCE LISTING

This application contains a Sequence Listing which has been submitted electronically in ASCII format and is hereby incorporated by reference in its entirety. Said ASCII copy, created on Jun. 30, 2020, is named 052566_505001WO_SequenceListing_ST25.txt and is 37,450 bytes in size.

BACKGROUND OF THE INVENTION

The use of biopolymers to modify the properties of biologically active agents is a recurring theme across a wide range of medical and biological applications. A variety of chemical linkers can be used to attach bioactive peptides or proteins to biopolymers to modify the pharmacological properties of the resulting conjugate for use as a drug that can provide optimal treatment of specific diseases. Peptide-polymer conjugate comprising multiple copies of one or more species of peptide conjugated to a single biopolymer chain have been employed to impart specific improvements to the pharmacological properties of the peptides, including: (1) higher binding affinity to the biological target, (2) slower diffusivity through a target tissue, and (3) inhibition of proteases that could deactivate the biological activity of the peptides or proteins.

These improved pharmacological properties of peptide-polymer conjugates are particularly useful for the delivery of potent drugs that are be delivered directly into the diseased tissue. The dose delivered directly into the tissue can be lower than would be required to achieve the same therapeutic effect after systemic administration because the drug has been administered locally to the target tissue. It is also possible to administer to drugs to tissues that otherwise have poor transport properties from the blood. Specific examples of tissues where direct drug administration is common include the posterior eye chamber via intravitreal injection and articular joints via intra-articular injection.

However, local tissue administration requires a professional to safely provide the required injection, which makes them more burdensome and costly to administer compared to systemic administration. When the peptide drug is administered as part of a peptide-polymer conjugate, it is possible to substantially reduce the frequency of drug administration, thereby reducing the burden on the patient to receive effective treatment. Furthermore, a reduction in the number of local injections reduces the risk of local tissue injury or adverse effects to the injection. Finally, the need for less frequent administrations can reduce the amount of time that the drug concentration in the target tissue is below the therapeutic concentration, thereby improving the overall efficacy of the drug. Based on these advantages, there is a strong motivation to develop protein-polymer drug products for a variety of diseases.

To appropriately formulate a peptide-polymer conjugate as a drug product, it is necessary to achieve sufficiently high drug concentrations to enable appropriate dosing in the patient. Achieving sufficient dosing requires achieving both an appropriate concentration of the peptide polymer conjugates in the drug product solution as well as the appropriate drug load of peptide conjugated to each polymer. It is also necessary to filter the peptide-polymer drug substance through a 0.22-micron filter to eliminate any bacteria or pathogens that may be contaminating the solution. Finally, the peptide-polymer drug product must exhibit shelf-stability by remaining in solution for up to two years from the date of manufacture to the date of clinical use. Interactions between the peptide-polymer conjugates can negatively impact the ability to complete any of these drug-enabling properties.

The linkers used to attach the polymer and the peptides can have a substantial impact on the pharmacological properties of the conjugates, intra-conjugate interactions, as well as conjugate-to-conjugate interactions. Therefore, there is a need to develop peptide-polymer conjugates with the specific linker chemistries that will enable them to achieve the preferred pharmacological properties for a given disease as well as to be successfully formulated into a drug product. The present invention meets this and other needs.

BRIEF SUMMARY OF THE INVENTION

In one embodiment, the present invention provides a conjugate of Formula I:

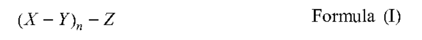

Formula (I)

wherein each X is independently a peptide having a molecular weight of from about 5 kDa to about 200 kDa; each Y is independently a hydrophilic linker; Z is a biocompatible polymer having a molecular weight of from about 0.1 MDa to about 3 MDa; and subscript n is an integer from 10 to 1000.

In another embodiment, the present invention provides a pharmaceutical composition including a conjugate of the present invention and a pharmaceutically acceptable excipient.

In another embodiment, the present invention provides a method of treating an ocular disease or disorder, the method comprising intravitreal administration to a subject in need thereof, a therapeutically effective amount of a conjugate of the present invention, thereby treating the ocular disease or disorder.

In another embodiment, the present invention provides a method of treating a disease or disorder in an articular joint, the method comprising injecting into the articular joint an effective amount of a conjugate of the present invention, thereby treating the disease or disorder in the articular joint.

BRIEF DESCRIPTION OF THE DRAWINGS

FIG. 9 shows PAGE analysis of Avastin polymer conjugates made with 830 kDa HA intermediate with EMCH linker (labeled A) or MP2H linker (labeled B) done without heating PAGE samples. Band that did not migrate into the gel is indicative of conjugate formation.

FIG. 10 shows PAGE analysis of goat anti-human IgG polymer conjugates made with 830 kDa HA intermediate with MP2H linker (labeled). Band that did not migrate into the gel is indicative of conjugate formation.

FIG. 13 shows BLI bioactivity data showing improved binding kinetics for MP2H Avastin IgG conjugate compared to EMCH Avastin conjugate or Avastin alone. Traut's Avastin indicates binding data for the Avastin IgG after activation with 2-iminothiolane (Traut's reagent).

FIG. 14 shows Bioactivity data showing binding kinetics for MP2H G5-1 anti-VEGF conjugate and EMCH G5-1 conjugate compared to G5-1 alone. G5-1 MP2H=conjugate 24, G5-1 EMCH=conjugate 25.

FIG. 18A and FIG. 18B shows PAGE analysis of purified peptide polymer conjugates using 2 kDa Natriuretic Peptide and polymer intermediates containing EMCH (labeled A or D) or MP2H (labeled B or C) ran with (FIG. 18B) and without (FIG. 18A) sample heat denaturation. Band that did not migrate into the gel is indicative of conjugate formation.

DETAILED DESCRIPTION OF THE INVENTION

I. General

Figure 1:
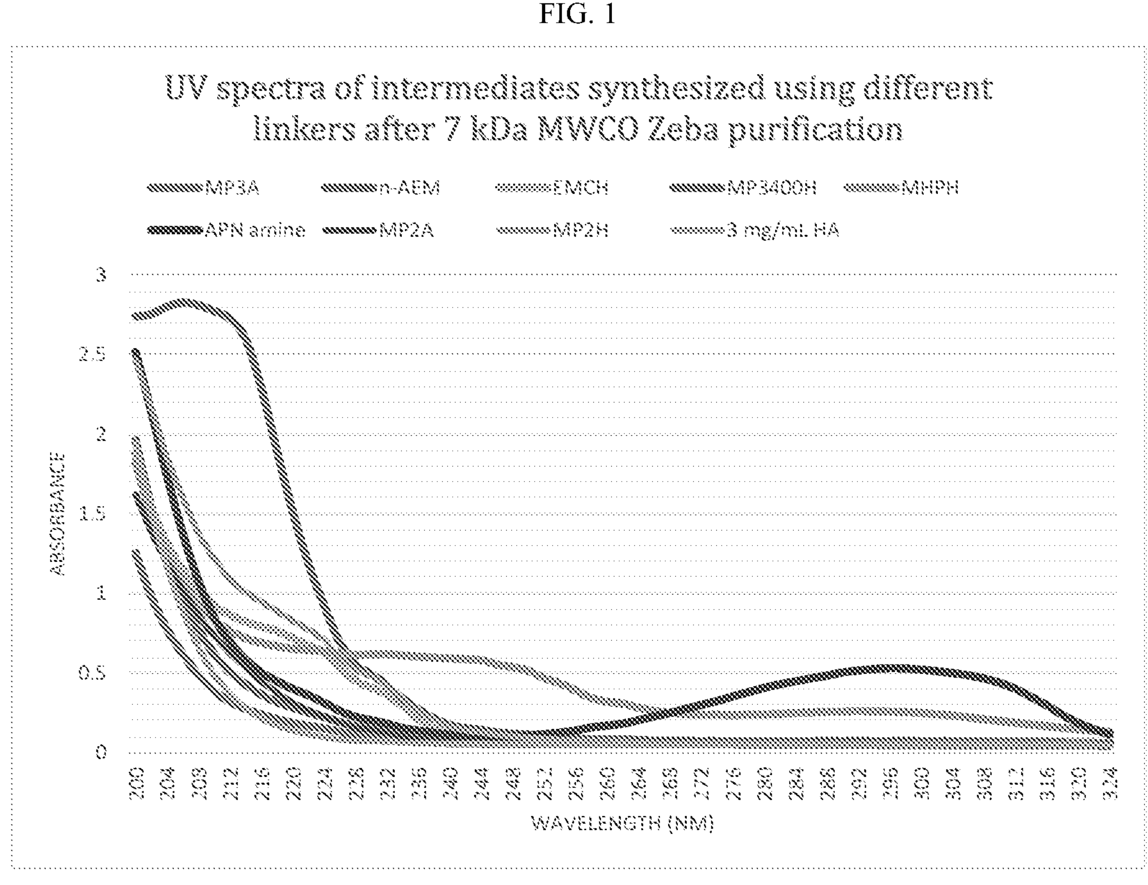
FIG. 1 shows UV spectra of purified 830 kDa hyaluronic acid intermediates synthesized using different thiol reactive linkers. See Table 2 for conjugates.
Figure 2:
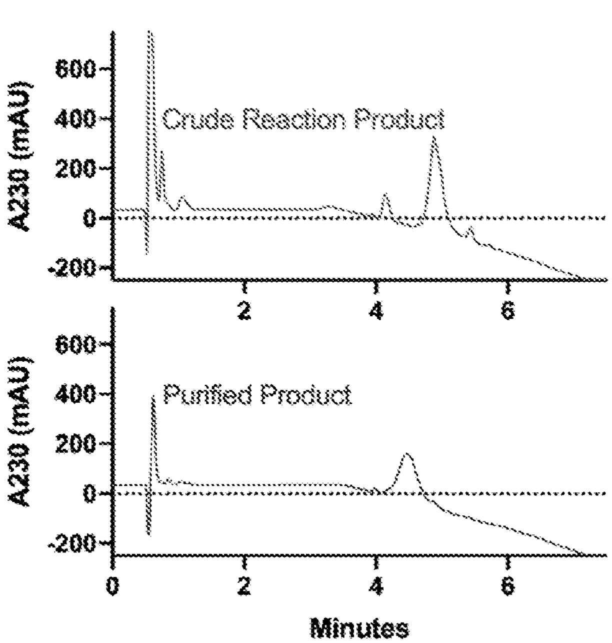
FIG. 2 shows reverse phase HPLC analysis of HyA-(Mal PEG2 Hydrazide) intermediate product before and after purification through a Zeba 7 kDa MWCO desalting column.
Figure 3:
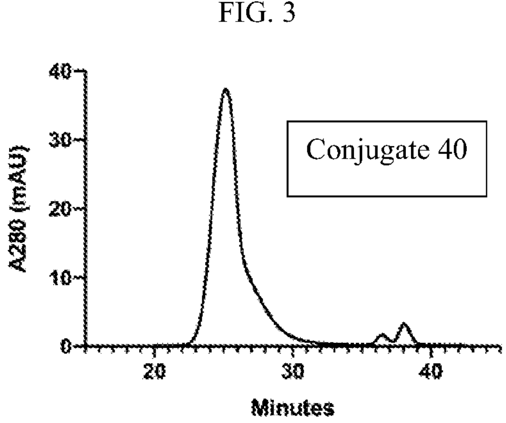
FIG. 3 shows SEC trace of conjugate 40 showing the conjugate peak, followed by the smaller DARPin dimer and monomer peaks.
Figure 4:
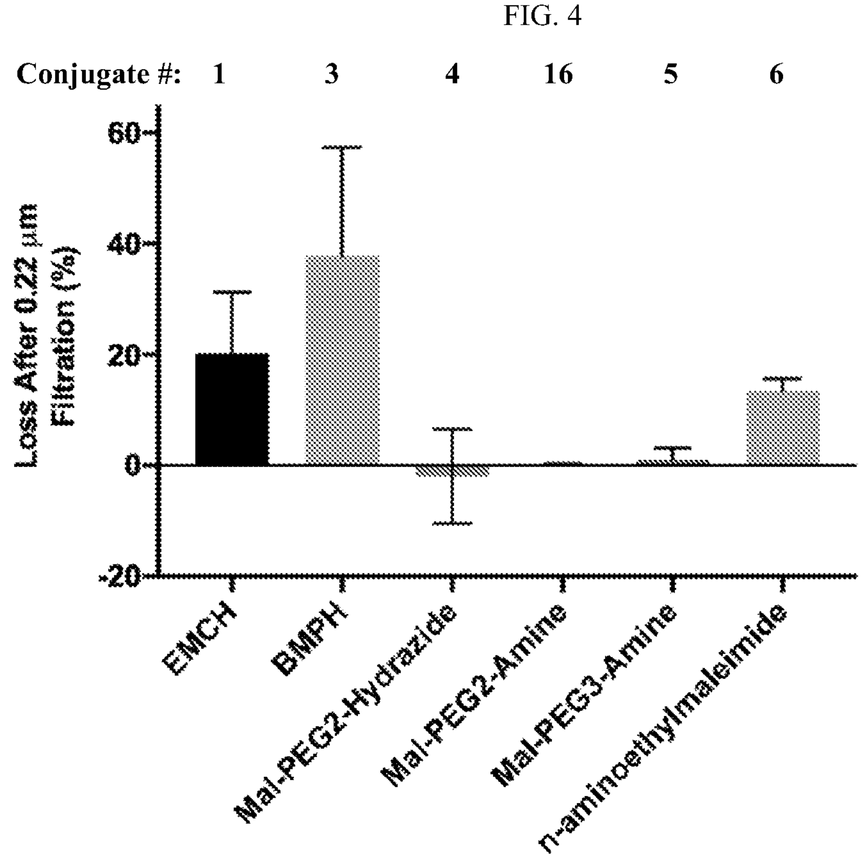
FIG. 4 shows percent loss after 0.22 um filtration for peptide protein conjugates 1 (EMCH), 3 (BMPH), 4 (MP2H), 16 (MP2A), 5 (MP3A), and 6 (n-AEM) linkers.
Figure 5:
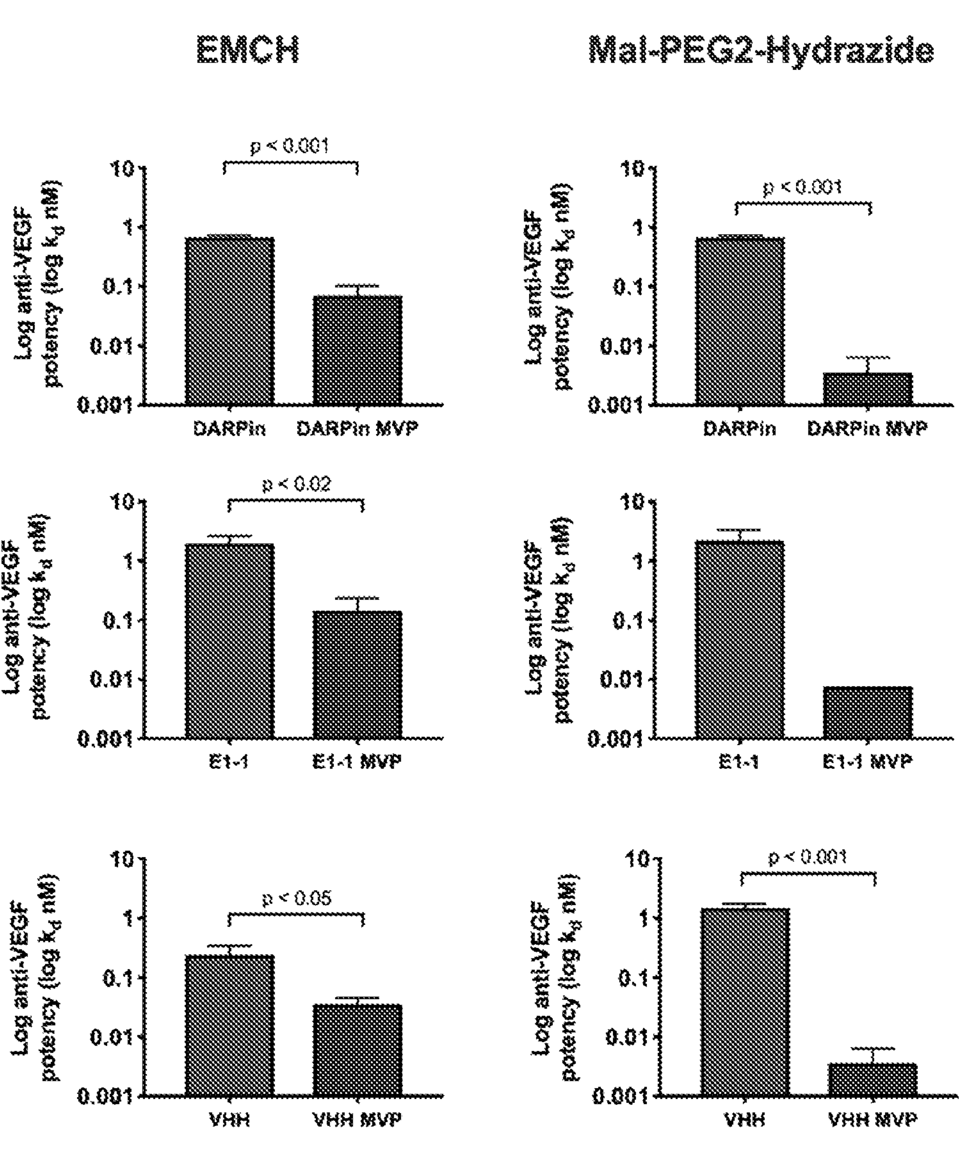
FIG. 5 shows improved log anti-VEGF potency for MVPs with a Mal-PEG2-hydrazide linker and a peptide of DARPin, E1-1 or VHH compared to MVPs with an EMCH linker.

The present invention provides peptide-polymer conjugates using hydrophilic linkers to covalently link each peptide to the polymer. The hydrophilic polymers provide added stability to the peptide-polymer conjugates.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"Thiol reactive group" refers to a group capable of reacting with a thiol to form a covalent bond to the sulfur atom. Representative thiol reactive groups include, but are not limited to, thiol, TNB-thiol, haloacetyl, aziridine, acryloyl, vinylsulfone, APN (3-arylpropiolonitrile), maleimide and pyridyl disulfide. Reaction of the thiol reactive group with a thiol can form a disulfide or a thioether.

"Thiol" refers to the —SH functional group.

"Heteroalkyl" refers to an alkyl group of any suitable length and having from 1 to 6 heteroatoms such as N, O and S. Additional heteroatoms can also be useful, including, but not limited to, B, Al, Si and P. The heteroatoms can also be oxidized, such as, but not limited to, —S(O)— and —$S(O)_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Heteroalkylene" refers to a heteroalkyl group, as defined above, linking at least two other groups. The two moieties linked to the heteroalkylene can be linked to the same atom or different atoms of the heteroalkylene.

"Carboxy reactive group" refers to a group capable of reacting with a carboxy or carboxylic acid group, i.e., —COOH. Representative carboxy reactive groups include, but are not limited to, amine, hydrazide, alcohol and thiol. Reaction with a carboxy reactive group can form an amide, ester or thioester.

"HyA" as used herein refers to hyaluronic acid.

"CMC" refers to carboxymethyl cellulose.

"scFV" refers to small chain variable fragment antibody.

"VHH" as used herein refers to a single-domain heavy chain antibody.

"DARPin" refers to a designed ankyrin repeat protein, which is a genetically engineered antibody mimetic protein that can exhibit highly specific and high-affinity target protein binding.

"Articular joint" as used herein refers to the fibrous or cartilaginous joints, which is a fibrous or cartilaginous area wherein two or more bones connect to each other.

"Therapeutically effective amount" as used herein refers to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

"Biocompatible polymer" as used herein refers to a polymer compatible with the joints at the injection site. Representative biocompatible polymers include, but are not limited to polysaccharides, glycosaminoglycans, and hyaluronic acid.

"Polymer molecular weight" as used herein refers to the molecular weight of the polymer.

"Peptide," "polypeptide," and "protein" are used interchangeably herein, and refer to naturally occurring and synthetic amino acids of any length, as well as amino acid analogs and amino acid mimetics that function in a manner similar to the naturally occurring amino acids. The term "polypeptide" includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes post-translationally modified polypeptides.

"Modulate" as used herein refers to the ability of a compound to increase or decrease the function, or activity, of the associated activity (e.g., immune cell function).

"Immune cell function" includes, for example, modulation of an immune response. The modulation can be immunosuppressive or immunostimulatory. Examples of immune responses can include, but are not limited to a humoral immune response, a cell-mediate immune response, or an inflammatory response.

"Inhibition", "inhibits" and "inhibitor" as used herein refer to a compound that prohibits or a method of prohibiting, a specific action or function.

"Antibody" as used herein refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Antibodies are representative of a wide variety of receptors including hormone receptors, drug targets such as peripheral benzodiazepine receptor, and carrier proteins. Representative antibodies include, but are not limited to monoclonal IgG antibodies, IgG antibody fragments, single chain scFv antibodies, single-domain heavy-chain VHH antibodies, or engineered antibody-like scaffolds such as adnectins, affibodies, anticalins, DARPins, and engineered Kunitz-type inhibitors. Other examples also include receptor decoys of immunomodulatory cytokines such as Tumor Necrosis Factor-α and IL-1β, IL-6, or interferon-γ.

"Sulfide bond" as used herein refers to any moiety having a sulfur covalent bond.

"Diffusion half-life" as used herein refers to the time it takes for the initial concentration of the conjugate within a given volume or space to decrease by half, where the decrease in concentration is a function of the concentration gradient.

"Intra-articular half-life" as used herein refers to the time it takes for the initial concentration of the conjugate within a particular joint to decrease by half, where the transport out of the joint is via convection. Convective transport is the combination of transport via diffusion and advection, where advective transport is the transport of a substance by bulk motion.

"Pharmaceutical composition" as used herein refers to a product comprising the specified ingredients in the specified amounts, as well as any product, which results, directly or indirectly, from combination of the specified ingredients in the specified amounts. The pharmaceutical composition is generally safe for biological use.

"Pharmaceutically acceptable carrier" and "pharmaceutically acceptable excipient" as used herein refers to a substance that aids the administration of an active agent to an absorption by a subject. Pharmaceutical carrier and/or excipient useful in the present invention include, but are not limited to, binders, fillers, disintegrants, lubricants, coatings, sweeteners, flavors and colors. One of skill in the art will recognize that other pharmaceutical carriers and/or excipients are useful in the present invention.

III. Peptide-Polymer Conjugates

The present invention provides conjugates of high molecular weight polymers and a plurality of peptides that possess a potency greater than a similar concentration of the unconjugated peptide, where the peptides are covalently linked to the polymer via a hydrophilic linker. In some embodiments, the present invention provides a conjugate of Formula I:

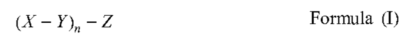

Formula (I)

wherein each X is independently a peptide having a molecular weight of from about 5 kDa to about 200 kDa; each Y is independently a hydrophilic linker; Z is a biocompatible polymer having a molecular weight of from about 0.1 MDa to about 3 MDa; and subscript n is an integer from 10 to 1000.

Anti-VEGF Peptides

Peptides that are suitable for inclusion in a conjugate, for use in a method of the present disclosure, include, but are not limited to, a neuroprotective polypeptide, an anti-angiogenic polypeptide, an anti-apoptotic factor, and a polypeptide that enhances function of a retinal cell.

Peptides that are suitable for inclusion in a conjugate, for use in a method of the present disclosure, include, but are not limited to, neuroprotective polypeptides (e.g., GDNF, CNTF, NT4, NGF, and NTN); anti-angiogenic polypeptides (e.g., a soluble vascular endothelial growth factor (VEGF) receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) Mol. Ther. 12:659); an Fc fusion protein comprising a soluble Flt polypeptide (see, e.g., Pechan et al. (2009) Gene Ther. 16:10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-Xl); and the like. Suitable polypeptides include, but are not limited to, glial derived neurotrophic factor (GDNF); fibroblast growth factor 2; neurturin (NTN); ciliary neurotrophic factor (CNTF); nerve growth factor (NGF); neurotrophin-4 (NT4); brain derived neurotrophic factor (BDNF); epidermal growth factor; rhodopsin; X-linked inhibitor of apoptosis; and Sonic hedgehog.

Peptides that are suitable for inclusion in a conjugate, for use in a method of the present disclosure, include, but are not limited to, a soluble vascular endothelial growth factor (VEGF) receptor; angiostatin, endostatin; vasostatin; retinal pigment epithelium-specific protein 65 kDa (RPE65); and compstatin. In some embodiments, the biologically active polypeptide is a soluble fms-like tyrosine kinase-1 (sFlt-1) polypeptide. In some embodiments, the biologically active polypeptide is a single-domain camelid (VHH) anti-VEGF antibody (VHH anti-VEGF antibody). In some embodiments, the biologically active polypeptide is a single chain Fv anti-VEGF antibody (scFv anti-VEGF antibody). In some embodiments, the peptide is an adnectin, an affibody, an anticalin, a DARPin, a Kunitz-type inhibitor, or a receptor decoy.

Peptides that are suitable for inclusion in a conjugate, for use in a method of the present disclosure, include, but are not limited to, glial derived neurotrophic factor, fibroblast growth factor 2, neurturin, ciliary neurotrophic factor, nerve growth factor, brain derived neurotrophic factor, epidermal growth factor, rhodopsin, X-linked inhibitor of apoptosis, retinoschisin, RPE65, retinitis pigmentosa GTPase-interacting protein-1, peripherin, peripherin-2, a rhodopsin, and Sonic hedgehog.

Suitable polypeptides also include retinoschisin. Suitable polypeptides include, e.g., retinitis pigmentosa GTPase regulator (RGPR)-interacting protein-1 (see, e.g., GenBank Accession Nos. Q96KN7, Q9EPQ2, and Q9GLM3); peripherin-2 (Prph2) (see, e.g., GenBank Accession No. NP_000313; and Travis et al. (1991) Genomics 10:733); peripherin; a retinal pigment epithelium-specific protein (RPE65) (see, e.g., GenBank AAC39660; and Morimura et al. (1998) Proc. Natl. Acad. Sci. USA 95:3088); and the like.

Suitable polypeptides also include: CHM (choroidermia (Rab escort protein 1)), a polypeptide that, when defective or missing, causes choroideremia (see, e.g., Donnelly et al. (1994) Hum. Mol. Genet. 3:1017; and van Bokhoven et al. (1994) Hum. Mol. Genet. 3:1041); and Crumbs homolog 1 (CRB1), a polypeptide that, when defective or missing, causes Leber congenital amaurosis and retinitis pigmentosa (see, e.g., den Hollander et al. (1999) Nat. Genet. 23:217; and GenBank Accession No. CAM23328).

Suitable peptides also include peptides that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) Ophthalmology 118:160-167); cone photoreceptor cGMP-gated cation channel beta-subunit (CNGB3) (see, e.g., Kohl et al. (2005) Eur J Hum Genet. 13(3):302); guanine nucleotide binding protein (G protein), alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) Nature 461(7265):784-787.

Peptides that are suitable for inclusion in a conjugate, for use in a method of the present disclosure, include an antibody. Suitable antibodies include, e.g., an antibody specific for VEGF; an antibody specific for tumor necrosis factor-alpha (TNF-$\alpha$); and the like.

Suitable antibodies include, but are not limited to, adalimumab, alemtuzumab, basiliximab, belimumab, bevacizumab, briakinumab, brodalumab, canakinumab, certolizumab, claakizumab, daclizumab, denosumab, efalizumab, epratuzumab, etaracizumab, fezakinumab, figitumumab, fontolizumab, gevokizumab, gotimumab, infliximab, namilumab, namilumab, natalizumab, neutrazumab, nextomab, ocaratuzumab, ofatumumab, olokizumab, pateclizumab, priliximab, ranibizumab, rituximab, secukinumab, sirukumab, sonepcizumab, tabalumab, tocilizumab, toralizumab, ustekinumab, vapaliximab, vedolizumab, veltuzumab, visilizumab, vorsetuzumab, and ziralimumab.

In some embodiments, the peptide is a soluble fins-like tyrosine kinase-1 (sFlt-1) polypeptide. In some embodiments, the peptide comprises an amino acid sequence having at least 80%, at least 85%, at least 90%, at least 95%, at least 98%, at least 99%, or 100%, amino acid sequence identity to a contiguous stretch of from 100 amino acids (aa) to 200 aa, from 200 aa to 300 aa, from 300 aa to 400 aa, from 400 aa to 500 aa, from 500 aa to 600 aa, from 600 aa to 700 aa, or from 700 aa to 755 aa, of the amino acid sequence depicted in SEQ ID NO:12. In some embodiments, the peptide comprises an amino acid sequence having at least 80%, at least 85%, at least 90%, at least 95%, at least 98%, at least 99%, or 100%, amino acid sequence identity to the amino acid sequence depicted in SEQ ID NO:13. In some embodiments, the peptide comprises an amino acid sequence having at least 80%, at least 85%, at least 90%, at least 95%, at least 98%, at least 99%, or 100%, amino acid sequence identity to the amino acid sequence depicted in SEQ ID NO:14. In some embodiments, the peptide comprises an amino acid sequence having at least 80%, at least 85%, at least 90%, at least 95%, at least 98%, at least 99%, or 100%, amino acid sequence identity to the amino acid sequence depicted in SEQ ID NO:15. In some embodiments, the peptide comprises the amino acid sequence depicted in SEQ ID NO:15.

In some embodiments, the peptide is an sFlt-1 polypeptide having a length of from 150 amino acids to 200 amino acids, from 200 to amino acids to 250 amino acids, from 250 amino acids to 300 amino acids, from 300 amino acids to 350 amino acids, or from 350 amino acids to 400 amino acids.

In some embodiments, the peptide is a scFv anti-VEGF antibody. Any suitable scFv anti-VEGF antibody can be used. A non-limiting example of an amino acid sequence of a scFv anti-VEGF antibody is provided in SEQ ID NO:16. An enterokinase cleavage site (DDDDK) and a poly(His) tract (HHHHHH) are present at the carboxyl terminus of the scFv anti-VEGF antibody depicted in F SEQ ID NO:16. In some embodiments, a scFv anti-VEGF antibody does not include an enterokinase cleavage site or a poly(His) tract.

In some embodiments, the peptide is a single domain camelid (VHH) anti-VEGF antibody. Any suitable VHH anti-VEGF antibody can be used. A non-limiting example of an amino acid sequence of a VHH anti-VEGF antibody is provided in SEQ ID NO:17. An enterokinase cleavage site (DDDDK) and a poly(His) tract (HHHHHH) are present at the carboxyl terminus of the VHH anti-VEGF antibody depicted in SEQ ID NO:17. In some embodiments, a VHH anti-VEGF antibody does not include an enterokinase cleavage site or a poly(His) tract.

In some embodiments, the peptide is an inhibitor of angiogenesis. In some embodiments, the peptide is a soluble vascular endothelial growth factor (VEGF) receptor, angiostatin, endostatin, vasostatin, an antibody specific for VEGF, or a DARPin specific for VEGF. In some embodiments, the peptide inhibits VEGF-A, VEGF-B, VEGF-C, VEGF-D, Ang-1, Ang-2, PDGF, or PlGF. In some embodiments, the peptide is a monoclonal IgG antibody, an IgG antibody fragment, a single-chain variable region antibody, a single-domain heavy chain antibody, an adnectin, an affibody, an anticalin, a DARPin, a Kunitz-type inhibitor, or a receptor decoy.

Anti-TNF Alpha Peptides

Peptides suitable in the present invention are those having a molecular weight of at least about 2 kDa, and exhibit tertiary structure. Representative peptides include, but are not limited to, polypeptides, one or more aptamers, avimer scaffolds based on human A domain scaffolds, diabodies, camelids, shark IgNAR antibodies, fibronectin type III scaffolds with modified specificities, antibodies, antibody fragments, proteins, peptides, polypeptides.

In some embodiments, the peptide is a therapeutic protein. Numerous therapeutic proteins are disclosed throughout the application such as, and without limitation, erythropoietin, granulocyte colony stimulating factor (G-CSF), GM-CSF, interferon alpha, interferon beta, human growth hormone, and imiglucerase.

In some embodiments, the peptide can be selected from specifically identified protein or peptide agents, including, but not limited to: Aβ, agalsidase, alefacept, alkaline phosphatase, aspariginase, amdoxovir (DAPD), antide, becaplermin, botulinum toxin including types A and B and lower molecular weight compounds with botulinum toxin activity, calcitonins, cyanovirin, denileukin diftitox, erythropoietin (EPO), EPO agonists, dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, N-Acetylgalactosamine-6-sulfate sulfatase, collagen, cyclosporin, alpha defensins, beta defensins, desmopressin, exendin-4, cytokines, cytokine receptors, granulocyte colony stimulating factor (G-CSF), thrombopoietin (TPO), alpha-1 proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, parathyroid hormone, parathyroid hormone related peptide, OP-1; acidic fibroblast growth factor, basic fibroblast growth factor, Fibroblast Growth Factor 21, CD-40 ligand, heparin, human serum albumin, low molecular weight heparin (LMWH), interferon alpha, interferon beta, interferon gamma, interferon omega, interferon tau, consensus interferon, human lysyl oxidase-like-2 (LOXL2); interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-15, interleukin-17, interleukin-21, interleukin-23, p40, interleukin-13 receptor, interleukin-17 receptor; lactoferrin and lactoferrin fragments, luteinizing hormone releasing hormone (LHRH), insulin, pro-insulin, insulin analogues, leptin, ghrelin, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF) (e.g., TNF-α and TNF-β), TNF receptors (e.g., TNF-α receptor and TNF-β receptor), CTLA4, CTLA4 receptor, monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$ tositumomab, trastuzumab, tuvirumab, visilizumab, and fragments and mimetics thereof.

In some embodiments, the peptide is a fusion protein. For example, and without limitation, the peptide can be an immunoglobulin or portion of an immunoglobulin fused to one or more certain useful peptide sequences. For example, the peptide may contain an antibody Fc fragment. In one embodiment, the peptide is a CTLA4 fusion protein. For example, the peptide can be an Fc-CTLA4 fusion protein. In another embodiment, the peptide is a Factor VIII fusion protein. For example, the peptide can be an Fc-Factor VIII fusion protein.

In some embodiments, the peptide is a human protein or human polypeptide, for example, a heterologously produced human protein or human polypeptide. Numerous proteins and polypeptides are disclosed herein for which there is a corresponding human form (i.e., the protein or peptide is normally produced in human cells in the human body). Therefore, in one embodiment, the peptide is the human form of each of the proteins and polypeptides disclosed herein for which there is a human form. Examples of such human proteins include, without limitation, human antibodies, human enzymes, human hormones and human cytokines such as granulocyte colony stimulation factor, granulocyte macrophage colony stimulation factor, interferons (e.g., alpha interferons and beta interferons), human growth hormone and erythropoietin.

Other examples of therapeutic proteins include, without limitation, factor VIII, b-domain deleted factor VIII, factor VIIa, factor IX, anticoagulants; hirudin, alteplase, tpa, reteplase, tpa, tpa—3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-aphal, consensus ifn, ifn-beta, ifn-beta 1b, ifn-beta 1a, ifn-gamma (e.g., 1 and 2), ifn-lambda, ifn-delta, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen cal 25, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the i12 receptor, chimeric mab directed against the alpha chain of the i12 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alpha (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone. And any of these can be modified to have a site-specific conjugation point (a N-terminus, or C-terminus, or other location) using natural (for example, a serine to cysteine substitution) (for example, formylaldehyde per method of Redwood Biosciences) or non-natural amino acid.

Examples of therapeutic antibodies (or their respective scFv or Fab fragments) useful in the present invention include, but are not limited to, Anti-TNF inhibitors such as the TNF receptor decoy etanercept and the monoclonal antibodies adalimumab, infliximab, golimumab, and certolizumab, the IL-6 monoclonal antibody inhibitor siltuximab, the IL-17 monoclonal antibody inhibitors secukinumab and ixekizumab, the IL-12/23 monoclonal antibody inhibitor ustekinumab, integrin receptor antagonists such as the monoclonal antibody inhibitors natalizumab and etrolizumab, the CLTA receptor antagonist abatacept, the IL-13 monoclonal antibody inhibitor tralokinumab, chemokine inhibitors such as the monoclonal antibodies eldelumab and bertilumab, and IL-1 inhibitors such as the receptor decoy rilonacept and the such as the monoclonal antibody canakinumab.

Other examples of therapeutic antibodies (or their respective scFv or Fab fragments) useful in the present invention include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIc receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-$\alpha V\beta$ integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-$\alpha$ antibody (CATI-BASF); CDP870 is a humanized anti-TNF-$\alpha$ Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-$\alpha$ IgG4 antibody (Celltech); LDP-02 is a humanized anti-$\alpha 4\beta 7$ antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-$\beta$.sub.2 antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Proteins and peptides disclosed herein can be produced by any useful method including production by in vitro synthesis and by production in biological systems. Typical examples of in vitro synthesis methods which are well known in the art include solid-phase synthesis ("SPPS") and solid-phase fragment condensation ("SPFC"). Biological systems used for the production of proteins are also well known in the art. Bacteria (e.g., *E. coli* and *Bacillus* sp.), yeast (e.g., *Saccharomyces cerevisiae* and *Pichia pastoris*) tobacco leaves (via tobacco mosaic virus) are widely used for the production of heterologous proteins. In addition, heterologous gene expression for the production of peptides for use as disclosed herein can be accomplished using animal cell lines such as mammalian cell lines (e.g., CHO cells). In one particularly useful embodiment, the peptides are produced in transgenic or cloned animals such as cows, sheep, goats and birds (e.g., chicken, quail, ducks and turkey), each as is understood in the art. See, for example, U.S. Pat. No. 6,781,030, issued Aug. 24, 2004, the disclosure of which is incorporated in its entirety herein by reference.

Protein or polypeptides useful in the present invention may also comprise non-naturally occurring amino acids in addition to the common naturally occurring amino acids found in proteins and polypeptides. In addition to being present for the purpose of altering the properties of a polypeptide or protein, non-naturally occurring amino acids can be introduced to provide a functional group that can be used to link the protein or polypeptide directly to the random copolymer. Furthermore, naturally occurring amino acids, e.g., cysteine, tyrosine, tryptophan can be used in this way.

Non-naturally occurring amino acids can be introduced into proteins and peptides by a variety of means. Some of the techniques for the introduction of non-natural amino acids are discussed in U.S. Pat. No. 5,162,218, the disclosure of which is incorporated in its entirety herein by reference. First, non-naturally occurring amino acids can be introduced by chemical modification of a polypeptide or protein on the amino acid side chain or at either the amino terminus or the carboxyl terminus. Non-limiting examples of chemical modification of a protein or peptide might be methylation by agents such as diazomethane, or the introduction of acetylation at an amino group present in lysine's side chain or at the amino terminus of a peptide or protein. Another example of the protein/polypeptide amino group modification to prepare a non-natural amino acid is the use of methyl 3-mercaptopropionimidate ester or 2-iminothiolane to introduce a thiol (sulfhydryl, —SH) bearing functionality linked to positions in a protein or polypeptide bearing a primary amine. Once introduced, such groups can be employed to form a covalent linkage to the protein or polypeptide.

Second, non-naturally occurring amino acids can be introduced into proteins and polypeptides during chemical synthesis. Synthetic methods are typically utilized for preparing polypeptides having fewer than about 200 amino acids, usually having fewer than about 150 amino acids, and more usually having 100 or fewer amino acids. Shorter proteins or polypeptides having less than about 75 or less than about 50 amino acids can be prepared by chemical synthesis.

The synthetic preparation methods that are particularly convenient for allowing the insertion of non-natural amino acids at a desired location are known in the art. Suitable synthetic polypeptide preparation methods can be based on Merrifield solid-phase synthesis methods where amino acids are sequentially added to a growing chain (Merrifield (1963) J. Am. Chem. Soc. 85:2149-2156). Automated systems for synthesizing polypeptides by such techniques are now commercially available from suppliers such as Applied Biosystems, Inc., Foster City, Calif. 94404; New Brunswick Scientific, Edison, N.J. 08818; and Pharmacia, Inc., Biotechnology Group, Piscataway, N.J. 08854.

Examples of non-naturally occurring amino acids that can be introduced during chemical synthesis of polypeptides include, but are not limited to: D-amino acids and mixtures of D and L-forms of the 20 naturally occurring amino acids, N-formyl glycine, ornithine, norleucine, hydroxyproline, beta-alanine, hydroxyvaline, norvaline, phenylglycine, cyclohexylalanine, t-butylglycine (t-leucine, 2-amino-3,3-dimethylbutanoic acid), hydroxy-t-butylglycine, amino butyric acid, cycloleucine, 4-hydroxyproline, pyroglutamic acid (5-oxoproline), azetidine carboxylic acid, pipecolinic acid, indoline-2-carboxylic acid, tetrahydro-3-isoquinoline carboxylic acid, 2,4-diaminobutyricacid, 2,6-diaminopimelic acid, 2,4-diaminobutyricacid, 2,6-diaminopimelicacid, 2,3-diaminopropionicacid, 5-hydroxylysine, neuraminic acid, and 3,5-diiodotyrosine.

Third, non-naturally occurring amino acids can be introduced through biological synthesis in vivo or in vitro by insertion of a non-sense codon (e.g., an amber or ocher codon) in a DNA sequence (e.g., the gene) encoding the polypeptide at the codon corresponding to the position where the non-natural amino acid is to be inserted. Such techniques are discussed for example in U.S. Pat. Nos. 5,162,218 and 6,964,859, the disclosures of which are incorporated in their entirety herein by reference. A variety of methods can be used to insert the mutant codon including oligonucleotide-directed mutagenesis. The altered sequence is subsequently transcribed and translated, in vivo or in vitro in a system which provides a suppressor tRNA, directed against the nonsense codon that has been chemically or enzymatically acylated with the desired non-naturally occurring amino acid. The synthetic amino acid will be inserted at the location corresponding to the nonsense codon. For the preparation of larger and/or glycosylated polypeptides, recombinant preparation techniques of this type are usually preferred. Among the amino acids that can be introduced in this fashion are: formyl glycine, fluoroalanine, 2-Amino-3-mercapto-3-methylbutanoic acid, homocysteine, homoarginine and the like. Other similar approaches to obtain non-natural amino acids in a protein include methionine substitution methods.

Where non-naturally occurring amino acids have a functionality that is susceptible to selective modification, they are particularly useful for forming a covalent linkage to the protein or polypeptide. Circumstances where a functionality is susceptible to selective modification include those where the functionality is unique or where other functionalities that might react under the conditions of interest are hindered either stereochemically or otherwise.

Other antibodies, such as single domain antibodies are useful in the present invention. A single domain antibody (sdAb, called Nanobody by Ablynx) is an antibody fragment consisting of a single monomeric variable antibody domain. Like a whole antibody, the sdAb is able to bind selectively to a specific antigen. With a molecular weight of only 12-15 kDa, single domain antibodies are much smaller than common whole antibodies (150-160 kDa). A single domain antibody is a peptide chain of about 110 amino acids in length, comprising one variable domain (VH) of a heavy chain antibody, or of a common IgG.

Unlike whole antibodies, single domain antibody (sdAbs) such as VHH do not show complement system triggered cytotoxicity because they lack an Fe region. Camelid and fish derived sdAbs are able to bind to hidden antigens that are not accessible to whole antibodies, for example to the active sites of enzymes.

A sdAb can be obtained by immunization of dromedaries, camels, llamas, alpacas or sharks with the desired antigen and subsequent isolation of the mRNA coding for heavy chain antibodies. Alternatively they can be made by screening synthetic libraries. Camelids are members of the biological family Camelidae, the only living family in the suborder Tylopoda. Camels, dromedaries, Bactrian Camels, llamas, alpacas, vicunas, and guanacos are in this group.

Peptides useful in the present invention also include, but are not limited to, a macrocyclic peptide, a cyclotide, an LDL receptor A-domain, a soluble receptor, an enzyme, a peptide multimer, a domain multimer, an antibody fragment multimer, and a fusion protein.

In some embodiments, the peptide modulates the activity of immune cell function. In some embodiments, the peptide inhibits tumor necrosis factor-α, interleukin-1β, interleukin-6, or interferon-γ. In some embodiments, the peptide inhibits tumor necrosis factor-α. In some embodiments, the peptide is a monoclonal IgG antibody, an IgG antibody fragment, a single-chain variable region antibody, a single-domain heavy chain antibody, an adnectin, an affibody, an anticalin, a DARPin, a Kunitz-type inhibitor, or a receptor decoy.

In some embodiments, the peptide can be anti-TNFa single-domain heavy-chain (VHH) antibody. In some embodiments, the peptide can be anti-TNFa affibody. In some embodiments, the peptide can be anti-TNFa designed ankyrin repeat protein (DARPin). In some embodiments, the peptide can be anti-IL-1B single-chain (scFv) antibody. In some embodiments, the peptide can be soluble interleukin receptor 2 (sILR2). In some embodiments, the peptide has an amino acid sequence that is SEQ ID NO:1, SEQ ID NO:2, SEQ ID NO:6, SEQ ID NO:7, SEQ ID NO:8, SEQ ID NO:9, SEQ ID NO:10 or SEQ ID NO:11. In some embodiments, the peptide has an amino acid sequence that is SEQ ID NO:1, SEQ ID NO:2, SEQ ID NO:6, SEQ ID NO:7, SEQ ID NO:8, SEQ ID NO:9, or SEQ ID NO:10. In some embodiments, the peptide has an amino acid sequence that is SEQ ID NO:1, SEQ ID NO:2, SEQ ID NO:6, SEQ ID NO:7, SEQ ID NO:9, SEQ ID NO:10 or SEQ ID NO:11. In some embodiments, the peptide has an amino acid sequence that is SEQ ID NO:6, SEQ ID NO:7, SEQ ID NO:9, or SEQ ID NO:11. In some embodiments, the peptide has an amino acid sequence that is SEQ ID NO:6, SEQ ID NO:7, or SEQ ID NO:9. In some embodiments, the peptide has an amino acid sequence that is SEQ ID NO:6. In some embodiments, the peptide has an amino acid sequence that is SEQ ID NO:7. In some embodiments, the peptide has an amino acid sequence that is SEQ ID NO:9.

Peptides useful in the present invention can have a molecular weight of at least 2 kDa. Peptides useful in the present invention can have a molecular weight of at least 2 kDa and exhibit a tertiary structure. For example, the molecular weight of the peptide can be from about 2 kDa to about 150 kDa, from about 5 kDa to about 150 kDa, from about 5 kDa to about 100 kDa, from about 2 kDa to about 50 kDa, from about 5 kDa to about 50 kDa, from about 5 kDa to about 30 kDa, from about 10 kDa to about 30 kDa, or from about 10 kDa to about 20 kDa. Representative molecular weights for the peptide includes about 2 kDa, or 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 110, 120, 130, 140, or about 150 kDa. In some embodiments, the peptide has a molecular weight of from about 5 kDa to about 30 kDa. In some embodiments, the peptide has a molecular weight of from about 10 kDa to about 20 kDa.

Linkers

The linkers of the present invention are hydrophilic linkers. The hydrophilic linkers can include naturally occurring molecules like nucleic acid bases, dimers, and oligomers, carbohydrate monomers or oligosaccharides of a variety of compositions, dextrans, dipeptides or oligopeptides. Other hydrophilic linkers can include, but are not limited to, ethylene glycol dimers, trimers, oligomers and polymers, as well as polyvinyl alcohol, polyvinyl acetate, polyacrylate, peptoids, D- or artificial amino acid containing peptides, polymer brushes, polyelectrolyte brushes, synthetic carbohydrate mono and oligomers, cleavable linkers. Any combination of the above like nucleic acid-amino acid-synthetic polymer, etc.

In some embodiments, each hydrophilic linker independently has the formula:

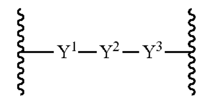

wherein $Y^1$ is a thiol reactive group; $Y^2$ is a $C_{3-20}$ heteroalkylene having from 1 to 6 heteroatoms each independently N, O or S, or $—(CH_2CH_2O)_m—$, wherein subscript m is an integer of from 1 to 100; and $Y^3$ is a carboxy reactive group.

In some embodiments, $Y^2$ is a $C_{3-20}$ heteroalkylene having from 1 to 6 heteroatoms each independently N, O or S. In some embodiments, $Y^2$ is $—(CH_2CH_2O)_m—$, wherein subscript m is an integer of from 1 to 100.

In some embodiments, each hydrophilic linker independently has the formula:

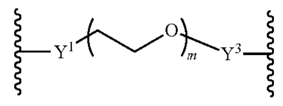

wherein $Y^1$ is a thiol reactive group; $Y^3$ is a carboxy reactive group; and subscript m is an integer of from 1 to 100. In some embodiments, subscript m is an integer of from 1 to 10. In some embodiments, subscript m is an integer of from 1 to 5. In some embodiments, subscript m is an integer of from 2 to 5. In some embodiments, subscript m is 2. In some embodiments, subscript m is 3. In some embodiments, subscript m is 4.

In some embodiments, $Y^1$ is a thiol, arylpropiolonitrile or maleimide; and $Y^3$ is an amine or a N-acylhydrazide. In some embodiments, $Y^1$ is maleimide; and $Y^3$ is an amine or a N-acylhydrazide. In some embodiments, $Y^1$ is maleimide; and $Y^3$ is an amine. In some embodiments, $Y^1$ is maleimide; and $Y^3$ is a N-acylhydrazide. In some embodiments, $Y^1$ is arylpropiolonitrile; and $Y^3$ is an amine or a N-acylhydrazide. In some embodiments, $Y^1$ is arylpropiolonitrile; and $Y^3$ is an amine. In some embodiments, $Y^1$ is arylpropiolonitrile; and $Y^3$ is a N-acylhydrazide.

In some embodiments, the hydrophilic linker has the formula:

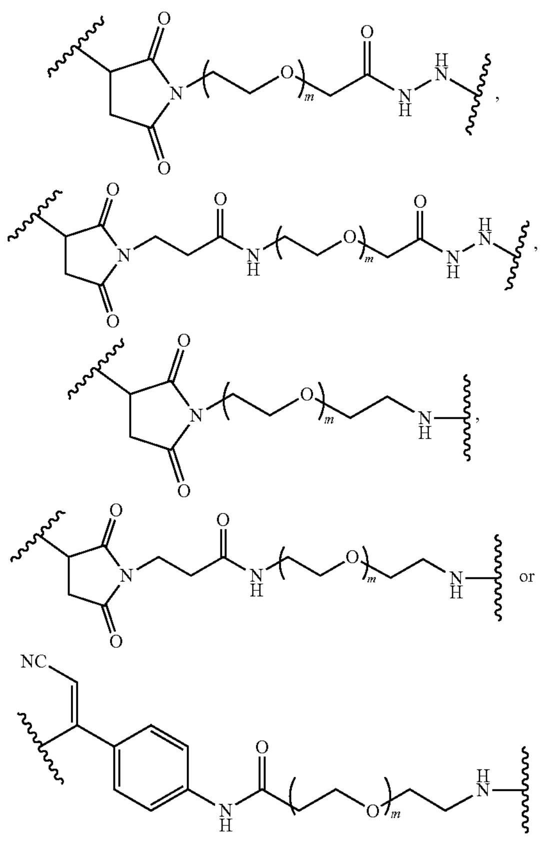

wherein subscript m is an integer of from 1 to 100. In some embodiments, the hydrophilic linker has the formula:

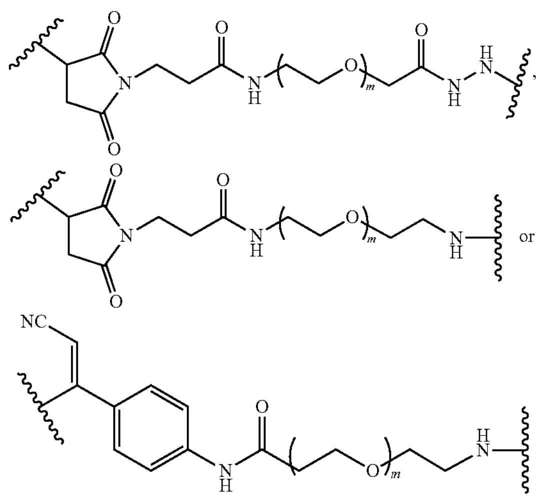

wherein subscript m is an integer of from 1 to 100. In some embodiments, subscript m is an integer of from 1 to 10. In some embodiments, subscript m is an integer of from 1 to 5. In some embodiments, subscript m is an integer of from 2 to 5. In some embodiments, subscript m is 2. In some embodiments, subscript m is 3. In some embodiments, subscript m is 4.

In some embodiments, the hydrophilic linker has the formula:

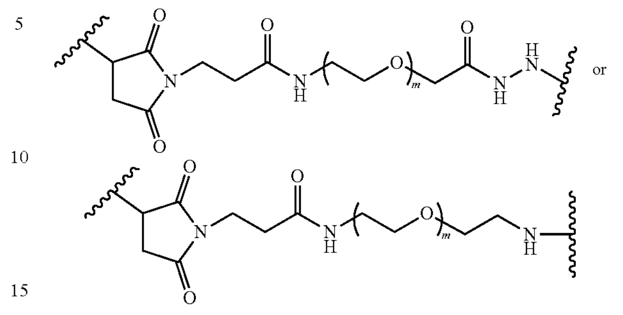

wherein subscript m is an integer of from 1 to 100. In some embodiments, subscript m is an integer of from 1 to 10. In some embodiments, subscript m is an integer of from 1 to 5. In some embodiments, subscript m is an integer of from 2 to 5. In some embodiments, subscript m is 3.

In some embodiments, the hydrophilic linker has the formula:

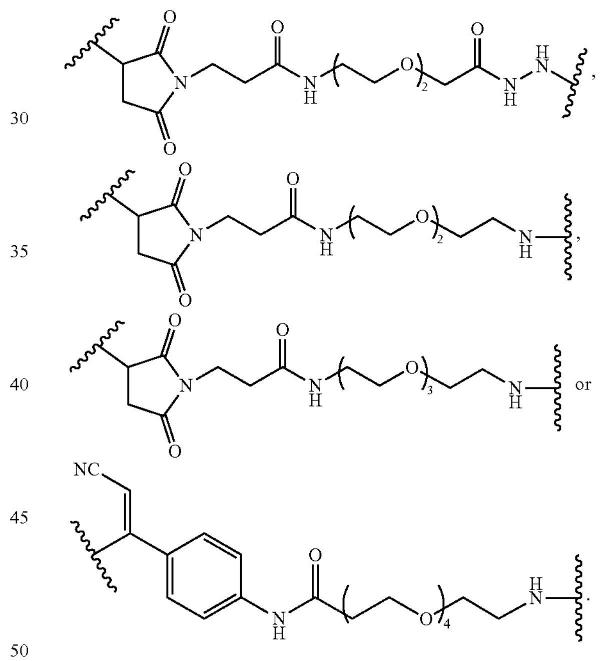

In some embodiments, the hydrophilic linker has the formula:

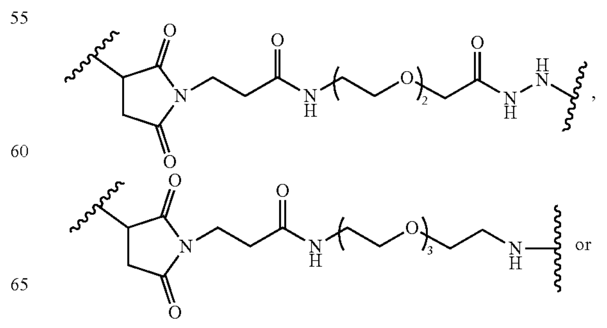

-continued

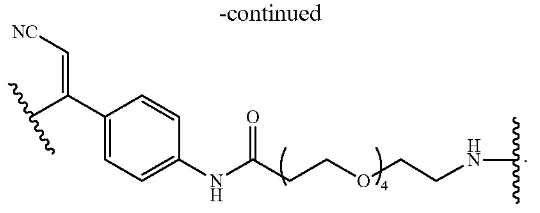

In some embodiments, the hydrophilic linker has the formula:

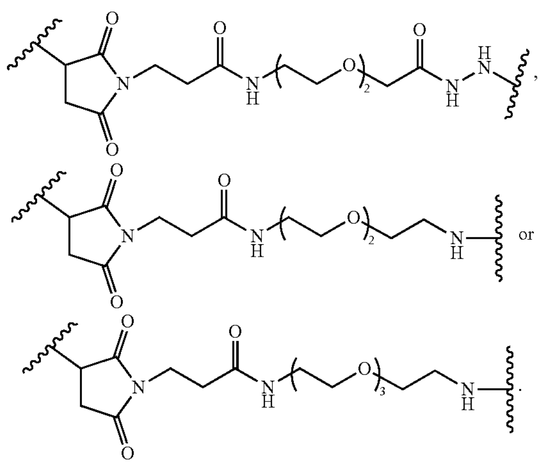

In some embodiments, the hydrophilic linker has the formula:

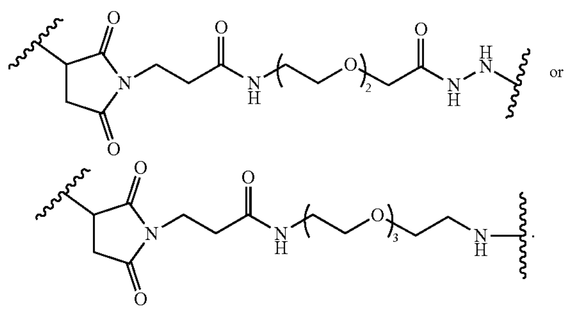

Biocompatible Polymers

Polymers useful in the conjugates of the present invention include any suitable biocompatible polymer. Biocompatible polymers are hydrophilic polymers that generally do not trigger an immune response. Suitable biocompatible polymers include, but are not limited to, polysaccharides, glycosaminoglycan, hyaluronic acid and derivatives thereof, cellulose, carboxymethylcellulose and derivatives thereof, heparin and derivatives thereof, dermatin, starch and modified starches, chondroitin, chitosan, carboxymethyl chitosan and others. The biocompatible polymer can also include polyvinylchloride, polytetrafluoroethylene, polyethersulfone, polyethylene, polyetheretherketone, polysulfone, polypropylene, poly(ethylene glycol), poly(propylene glycol), polyurethanes, ethylene vinyl acetate copolymers, collagen, poly isobutylene, ethylene vinyl alcohol copolymers, polyethylene polycarbonate, polycaprolactone, polylactide, polyglycolide, carbomers, polyesters, polyethers, polyanhydrides, polyacrylates, polyvinyl acetates, polyvinyl pyrrolidones, polysaccharides (such as hyaluronic acid, hydroxyalkylcelluloses, carboxyalkylcelluloses, or derivatives thereof), polyether, derivatives thereof and combinations thereof. The biocompatible polymers can be further modified by methods such as sulfation, sulfonation, deuteration, etc.

Polysaccharides useful as the biocompatible polymer include, but are not limited to, cellulose, carboxymethylcellulose, methyl cellulose, hydroxypropyl cellulose, chitin, glycosaminoglycans, chondroitin sulfate, hyaluronan (hyaluronic acid), heparin, heparan sulfate, among others. In some embodiments, the biocompatible polymer can be a polysaccharide. In some embodiments, the biocompatible polymer can be a glycosaminoglycan. In some embodiments, the biocompatible polymer can be hyaluronic acid.

The biocompatible polymer of the present invention can be of any suitable molecular weight. For example, suitable biocompatible polymers can have a molecular weight of from about 0.1 MDa to about 3 MDa, or about 100 kDa to about 3,000 kDa. A polymer molecular weight can typically be expressed as the number average molecular weight ($M_n$) or the weight average molecular weight ($M_w$). The number average molecular weight is the mathematical mean of the molecular masses of the individual macromolecules. The weight average molecular weight is influenced by larger molecules and so is a larger number than the number average molecular weight. The ratio of $M_w/M_n$ is the polydispersity of the polymer and represents the breadth of molecular weights in the polymer sample. Reference to molecular weights in the present invention are to the weight average molecular weight ($M_w$) unless stated otherwise.

Molecular weights useful for biocompatible polymer include, but are not limited to, from about 0.1 MDa to about 3 MDa, from about 0.1 MDa to about 2 MDa, from about 0.2 MDa to about 1.5 MDa, from about 0.8 MDa to about 3 MDa, from about 1 MDa to about 3 MDa, from about 1.5 MDa to about 3 MDa, or from about 1 MDa to about 2 MDa. In some embodiments, the biocompatible polymer has a molecular weight of from about 0.1 MDa to about 3 MDa. In some embodiments, the biocompatible polymer has a molecular weight of from about 0.1 MDa to about 2 MDa. In some embodiments, the biocompatible polymer has a molecular weight of from about 0.2 MDa to about 1.5 MDa. In some embodiments, the biocompatible polymer has a molecular weight of from about 0.8 MDa to about 3 MDa. The biocompatible polymer can have a molecular weight of about 0.1 MDa, or 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or about 3 MDa. In some embodiments, the biocompatible polymer has a molecular weight of at least about 0.85 MDa. In some embodiments, the biocompatible polymer has a molecular weight of about 0.9 MDa. In some embodiments, the biocompatible polymer has a molecular weight of at least about 1 MDa. In some embodiments, the biocompatible polymer has a molecular weight of about 2 MDa.

The biocompatible polymer can have a molecular weight of from about 2 kDa to about 750 kDa per peptide, or 5 kDa to about 600 kDa per peptide, from about 5 kDa to 500 kDa, from about 5 kDa to about 400 kDa, from about 5 kDa to about 300 kDa, from about 5 kDa to about 200 kDa, to about 5 kDa to about 100 kDa, from about 5 kDa to about 50 kDa, from about 5 kDa to about 40 kDa, from about 5 kDa to about 30 kDa, from about 5 kDa to about 20 kDa, or from about 5 kDa to about 10 kDa per peptide. The biocompatible polymer can have a molecular weight per peptide of about 5 kDa, or 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or about 100 kDa.

Conjugates

The peptide-polymer conjugates of the present invention can include any suitable combination of peptide and biocompatible polymer where the molar ratio of peptide to polymer is at least 5:1. Representative molar ratios of peptide to biocompatible polymer useful in the present invention include from 5:1 to about 1000:1, from 5:1 to about 500:1, from 5:1 to about 400:1, from about 10:1 to about 500:1, from about 10:1 to about 400:1, from about 10:1 to about 300:1, from about 10:1 to about 200:1, from about 10:1 to about 100:1, from about 20:1 to about 100:1, from about 30:1 to about 100:1, from about 50:1 to about 100:1, from about 10:1 to about 50:1, from about 20:1 to about 50:1, or from about 30:1 to about 50:1. Other molar ratios of peptide to biocompatible polymer useful in the present invention include from about 50:1 to about 500:1, from about 50:1 to about 400:1, from about 50:1 to about 300:1, or from about 50:1 to about 200:1. Representative molar ratios of peptide to biocompatible polymer include about 10:1, or 15:1, 20:1, 25:1, 30:1, 35:1, 40:1, 45:1, 50:1, 60:1, 70:1, 80:1, 90:1, 100:1, 125:1, 150:1, 175:1, 200:1, 250:1, 300:1, 350:1, 450:1, 500:1, 550:1, 600:1, 650:1, 700:1, 750:1, 800:1, 850:1, 900:1, 950:1 or about 1000:1. In some embodiments, subscript n is an integer of from 10 to 400. In some embodiments, subscript n is an integer of from 10 to 100. In some embodiments, subscript n is an integer of from 50 to 100.

The conjugates of the peptide of biocompatible polymer of the present invention can have longer diffusion half-lives compared to the unconjugated peptide. For example, the conjugate can have a diffusion half-life of at least 2 times longer than that of the peptide, or 3, 4, 5, 6, 7, 8, 9, 10, 15, 20, 25, 30, 35, 40, 45, 50, 60, 70, 80, 90, or at least 100 times longer than that of the peptide. The diffusion half-life of the conjugate can be from about 2 to about 100 times longer than the peptide, or from about 2 to about 50, from about 10 to about 100, from about 25 to about 100, from about 50 to about 100 times longer than the peptide. In some embodiments, the diffusion half-life of the conjugate is at least about 2 times longer than the peptide. In some embodiments, the diffusion half-life of the conjugate is from about 2 to about 100 times longer than the peptide.

The conjugates of the present invention can also have longer intra-articular half-lives compared to the unconjugated peptide. For example, the conjugate can have an intra-articular half-life that is at least 20% longer than the unconjugated peptide, or at least 50, 75, 100, 150, 200, 250, 300, 350, 400, 450, 500, 600, 700, 800, 900 or 1000% longer than the unconjugated peptide. The intra-articular half-life of the conjugate can be from about 20% to about 1000% longer than the unconjugated peptide, or from about 100% to about 1000%, or from about 100% to about 500%, or from about 100% to about 300% longer than the unconjugated peptide. In some embodiments, the intra-articular half-life of the conjugate is at least about 20% longer than the peptide. In some embodiments, the intra-articular half-life of the conjugate is from about 20% to about 1000% longer than the peptide.

In some embodiments, the biocompatible polymer has a molecular weight of from about 0.8 MDa to about 3 MDa; and each peptide has a molecular weight of from about 5 kDa to about 50 kDa; wherein each peptide is covalently linked to the polymer, and the molar ratio of the peptides to the polymer in the conjugate is at least about 10:1. In some embodiments, the biocompatible polymer has a molecular weight of from about 0.8 MDa to about 2 MDa; and each peptide has a molecular weight of from about 5 kDa to about 50 kDa; wherein each peptide is covalently linked to the polymer, and the molar ratio of the peptides to the polymer in the conjugate is at least about 10:1. In some embodiments, the biocompatible polymer has a molecular weight of from about 1 MDa to about 2 MDa; and each peptide has a molecular weight of from about 5 kDa to about 50 kDa; wherein each peptide is covalently linked to the polymer, and the molar ratio of the peptides to the polymer in the conjugate is at least about 10:1. In some embodiments, the biocompatible polymer has a molecular weight of from about 1 MDa to about 2 MDa; and each peptide has a molecular weight of from about 5 kDa to about 50 kDa; wherein each peptide is covalently linked to the polymer, and the molar ratio of the peptides to the polymer in the conjugate is at least about 20:1. In some embodiments, the biocompatible polymer has a molecular weight of about 2 MDa; and each peptide has a molecular weight of from about 5 kDa to about 50 kDa; wherein each peptide is covalently linked to the polymer, and the molar ratio of the peptides to the polymer in the conjugate is at least about 50:1.

A drug that exhibits greater intravitreal residence time may be preferred by the patient as well relative to a drug product that must be administered more frequently for an equivalent therapeutic function. While the intravitreal injection is us performed under topical anesthesia and is generally not regarded as painful, it is burdensome for the patient. It must be performed by a clinician, and thus an office visit is required for each administration of the drug. There is typically short-term irritation and blurred vision due to increased tearing. There may also be short tear changes to the appearance of the eye at the vicinity of the injection site. Finally, progressive and irreversible disease damage can occur when the patient delays treatment, and less frequent opportunities for delayed treatment corresponds to better overall long-term efficacy. Thus, patients would likely exhibit a preference for an equivalent therapy that would require fewer intravitreal injections.

The need for less frequent injections would also be preferable from the physician's perspective. The intravitreal injections must be performed by an ophthalmologist, and thus this procedure can occupy a substantial portion of their clinic time. The number of patients that are receiving the intravitreal therapy in their practice can be limited by the frequency that each patient must receive the intravitreal injections. Less frequent injection would increase the number patients that are able receive the method of therapy. A longer acting drug would also be preferable to a depot or long-term drug delivery device, as these typically require a longer implantation procedure and access to a procedure room, which may offset the benefits of less frequent administration for the clinician.

A conjugate comprising a biologically active polypeptide and a biocompatible polymer exhibits a half-life in the vitreous that is greater than the half-life in the vitreous of the biologically active polypeptide not conjugated to the biocompatible polymer. The increased half-life of the conjugate in the vitreous confers certain advantages, including, e.g., reduced burden on the patient; reduced number and/or frequency of administrations; increased safety; decreased incidence of infection; increased patient compliance; and increased efficacy. In addition, a conjugate as described herein allows use of polypeptides for treatment of ocular disorders, which polypeptides would not, in unconjugated form, be retained in the eye for a time period suitable for therapy.

In some embodiments, an effective amount of a conjugate is an amount that is effective to inhibit pathological angiogenesis in the eye of the individual. For example, in some cases, an effective amount of a conjugate is an amount that, when administered in one or more doses, is effective to inhibit pathological angiogenesis in the eye of the individual by at least 10%, at least 15%, at least 20%, at least 25%, at least 30%, at least 40%, at least 50%, at least 60%, at least 70%, or at least 80%, or more than 80%, compared to the degree of pathological angiogenesis in the eye in the absence of treatment with the conjugate, or before treatment with the conjugate.

In some embodiments, an effective amount of a conjugate is an amount that is effective to reduce intraocular pressure in the eye of the individual. For example, in some cases, an effective amount of a conjugate is an amount that, when administered in one or more doses, is effective to reduce intraocular pressure by at least 10%, at least 15%, at least 20%, at least 25%, at least 30%, at least 40%, at least 50%, at least 60%, at least 70%, or at least 80%, or more than 80%, compared to the intraocular pressure in the eye in the absence of treatment with the conjugate, or before treatment with the conjugate.

In some embodiments, an effective amount of a conjugate is an amount that is effective to reduce macular edema in the eye of the individual. For example, in some cases, an effective amount of a conjugate is an amount that, when administered in one or more doses, is effective to reduce macular edema by at least 10%, at least 15%, at least 20%, at least 25%, at least 30%, at least 40%, at least 50%, at least 60%, at least 70%, or at least 80%, or more than 80%, compared to the level of macular edema in the eye in the absence of treatment with the conjugate, or before treatment with the conjugate.

In some embodiments, an effective amount of a conjugate is an amount that is effective to increase visual acuity in an eye of the individual. For example, in some cases, an effective amount of a conjugate is an amount that, when administered in one or more doses, is effective to increase visual acuity in an eye of the individual by at least at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, or at least 10-fold, or more than 10-fold, compared to the visual acuity in the eye in the absence of treatment with the conjugate, or before treatment with the conjugate.

In some embodiments, an effective amount of a conjugate is an amount that is effective to inhibit progression of an ocular disease in an individual. For example, in some cases, an effective amount of a conjugate is an amount that, when administered in one or more doses, is effective to inhibit progression of an ocular disease in the individual by at least 10%, at least 15%, at least 20%, at least 25%, at least 30%, at least 40%, at least 50%, at least 60%, at least 70%, or more, compared to the progression in the absence of treatment with the conjugate, or before treatment with the conjugate.

For example, is in some cases, an effective amount of a conjugate is an amount that, when administered in one or more doses, is effective to inhibit progression of non-exudative ARMD to exudative ARMD or to inhibit progression of non-exudative ARMD to a more severe form. In some embodiments, an effective amount of a conjugate is an amount that is effective to inhibit progression of early ARMD (AREDS 2) to intermediate ARMD (AREDS 3) or to advanced ARMD (AREDS 4). In some embodiments, an effective amount of a conjugate is an amount that is effective to inhibit progression of intermediate ARMD (AREDS 3) to advanced ARMD (AREDS 4).

In some embodiments, an effective amount of a conjugate is an amount that is effective to enhance a biological activity of a retinal cell, e.g., where the retinal cell is a photoreceptor, a retinal ganglion cell, a Muller cell, a bipolar cell, an amacrine cell, a horizontal cell, or a retinal pigmented epithelium cell.

In some embodiments, a conjugate comprising a biologically active polypeptide and a biocompatible polymer exhibits a half-life in the vitreous of from about 12 hours to about 24 hours, from about 1 day to about 3 days, from about 3 days to about 7 days, from one week to about 2 weeks, from about 2 weeks to about 4 weeks, or from about 1 month to about 6 months.

In some embodiments, a conjugate comprising a biologically active polypeptide and a biocompatible polymer exhibits a therapeutically efficacious residence time in the vitreous of from about 12 hours to about 24 hours, from about 1 day to about 3 days, from about 3 days to about 7 days, from one week to about 2 weeks, from about 2 weeks to about 4 weeks, from about 1 month to about 3 months, or from about 3 months to about 6 months.

The biological activity of a polypeptide conjugated to the polymer substrate is enhanced relative to the activity of the polypeptide in soluble form, e.g., compared to the activity of the polypeptide not conjugated to the polymer. In some embodiments, the biological activity of the polypeptide of a polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide in soluble (unconjugated) form.

In some embodiments, the biological activity of the polypeptide of a suitable polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide in when conjugated to the polymer at a 1:1 molar ratio.

In some embodiments, the biological activity of the polypeptide of a suitable polypeptide-polymer conjugate is at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the biological activity of the polypeptide when present in admixture with the polymer.

In some embodiments, the half-maximal effective concentration (EC50) of the polypeptide of a subject polypeptide-polymer conjugate is at least about 10%, at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, lower than the EC50 of the polypeptide in soluble (unconjugated form).

In some embodiments, the half-maximal inhibitory concentration (IC50) of the polypeptide of a subject polypeptide-polymer conjugate is at least about 10%, at least about 25%, at least about 50%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, lower than the IC50 of the polypeptide in soluble (unconjugated form).

Whether the biological activity of the polypeptide of a polypeptide-polymer conjugate is increased relative to the biological activity of the polypeptide in soluble (unconjugated) form is readily determined using an appropriate assay(s) for the biological activity.

The molar ratio of the polypeptide to the polymer can vary from about 5:1 to about 100:1, e.g., from about 5:1 to about 7:1, from about 7:1 to about 10:1, from about 10:1 to about 2:1, from about 12:1 to about 15:1, from about 15:1 to about 20:1, from about 20:1 to about 25:1, from about 25:1 to about 30:1, from about 30:1 to about 35:1, from about 35:1 to about 40:1, from about 40:1 to about 45:1, from about 45:1 to about 50:1, from about 50:1 to about 60:1, from about 60:1 to about 70:1, from about 70:1 to about 80:1, from about 80:1 to about 90:1, or from about 90:1 to about 100:1.

For example, where a polypeptide polymer conjugate comprises a polypeptide that inhibits angiogenesis (e.g., the polypeptide is an anti-angiogenic polypeptide), in some embodiments, the anti-angiogenic polypeptide of a polypeptide-polymer conjugate inhibits angiogenesis by at least about 10%, at least about 15%, at least about 20%, at least about 25%, at least about 30%, at least about 40%, at least about 50%, at least about 60%, at least about 75%, at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, or more, compared to the degree of inhibition of angiogenesis by the anti-angiogenic polypeptide when present in admixture with the polymer, when in soluble (unconjugated) form, or when conjugated to the polymer at a 1:1 molar ratio.

IV. Pharmaceutical Compositions

In some embodiments, the present invention provides a pharmaceutical composition including a conjugate of the present invention and a pharmaceutically acceptable excipient.

A. Formulation

For preparing pharmaceutical compositions from the conjugates of the present invention, pharmaceutically acceptable carriers can be either solid or liquid. Solid form preparations include powders, cachets, and dispersible granules. A solid carrier can be one or more substances, which may also act as diluents, binders, preservatives, disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the conjugates of the present invention.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the conjugates of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolality.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the conjugates of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration into a body cavity such as the intra articular space of a joint. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46: 1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

B. Administration

The conjugates and compositions of the present invention can be delivered by any suitable means, including oral, parenteral and topical methods. In some embodiments, the delivery method is intra-articular.

The pharmaceutical preparation is preferably in unit dosage form. In such form the preparation is subdivided into unit doses containing appropriate quantities of the conjugates and compositions of the present invention. The unit dosage form can be a packaged preparation, the package containing discrete quantities of preparation, such as packeted tablets, capsules, and powders in vials or ampoules.

The conjugates and compositions of the present invention can be co-administered with other agents. Co-administration includes administering the conjugate or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the conjugates and compositions of the present invention can each be administered once a day, or two, three, or more times per day so as to provide the preferred dosage level per day.

In some embodiments, co-administration can be accomplished by co-formulation, i.e., preparing a single pharmaceutical composition including the conjugates and compositions of the present invention and any other agent. Alternatively, the various components can be formulated separately.

The conjugates and compositions of the present invention, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg. The composition can also contain other compatible therapeutic agents. The conjugates described herein can be used in combination with one another, with other active agents known to be useful in modulating a glucocorticoid receptor, or with adjunctive agents that may not be effective alone, but may contribute to the efficacy of the active agent.

V. Methods of Ocular Treatment

Ocular disorders that can be treated using a method of the present disclosure include, but are not limited to, macular degeneration, choroidal neovascularization, macular edema, retinal neovascularization, proliferative vitreoretinopathy, glaucoma, and ocular inflammation.

Ocular diseases that can be treated using a method of the present disclosure include, but are not limited to, acute macular neuroretinopathy; Behcet's disease; choroidal neovascularization; diabetic uveitis; non-infectious uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy and diabetic macular edema), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

In some embodiments, the ocular disease is glaucoma, retinitis pigmentosa, macular degeneration, retinoschisis, Leber's Congenital Amaurosis, diabetic retinopathy, achromotopsia, or color blindness. In some embodiments, the ocular disorder is macular degeneration, choroidal neovascularization, retinal neovascularization, proliferative vitreoretinopathy, glaucoma, or ocular inflammation. In some embodiments, the ocular disorder is macular degeneration, choroidal neovascularization, retinal neovascularization, proliferative vitreoretinopathy, diabetic retinopathy, glaucoma, or ocular inflammation.

Subjects suitable for treatment with a method of the present disclosure include individuals who have been diagnosed as having an ocular disease or disorder, e.g., any of the above-listed ocular diseases or disorders. Subjects suitable for treatment with a method of the present disclosure include individuals who have been treated for an ocular disease or disorder, and who have failed to respond to the treatment.

Individuals suitable for treatment with a method of the present disclosure include individuals with reduced visual acuity due to an ocular disease or disorder. Individuals suitable for treatment with a method of the present disclosure include individuals with abnormally high ocular pressure due to an ocular disease or disorder. Individuals suitable for treatment with a method of the present disclosure include individuals with pathological angiogenesis in an eye due to an ocular disease or disorder.

Visual acuity can be measured using, for example, a Snellen chart, a Bailey-Lovie chart, a decimal progression chart, a Freiburg visual acuity test, a measurement of minimum angle of resolution (MAR), Best Corrected Visual Acuity (BCVA) test, log of the Minimum Angle of Resolution (LogMAR) test, etc. Metamorphopsia (visual distortion) may be measured using an Amsler chart. Contrast sensitivity may be measured using a Pelli-Robson chart. Diagnostic studies include, but are not limited to, standard ophthalmologic examination of the fundus, stereo biomicroscopic examination of the macula, intravenous fundus fluorescein angiography, fundus photography, indocyanine green video-angiography, and optical coherence tomography. A subject displaying an abnormality on one or more of these diagnostic studies (e.g., a subject that falls outside a range that is considered normal for a healthy eye) may be treated in accordance with the present disclosure. For example, subjects may be classified as having early, intermediate, or advanced ARMD in accordance with the classification scheme used in the Age-Related Eye Diseases Study. A subject falling into any of the categories described therein, may be treated in accordance with a method of the present disclosure.

The conjugates useful in the method of treating an ocular disease or disorder can have any suitable vitreous half-life. For example, the vitreous half-life can be from about 12 hours to about 24 hours, from about 1 day to about 3 days, from about 3 days to about 7 days, from one week to about 2 weeks, from about 2 weeks to about 4 weeks, or from about 1 month to about 6 months. In some embodiments, the vitreous half-life of the conjugate is at least 2 weeks.

In some embodiments, the subject is a human.

The conjugates useful in the method of treating an ocular disease or disorder can be administered at any suitable interval. For example, the conjugate can be administered at least once a day, or at least once every 2, 3, 4, 5, 6 or 7 days, or at least once every 1, 2, 3 or 4 weeks, or at least once every 1, 2, 3, 4, 5, 6, 7, 8, 9, 10, 11 or 12 months. In some embodiments, the conjugate can be administered once every two months, once every three months, once every 6 months, or once a year. In some embodiments, the conjugate can be administered once every two months. In some embodiments, the conjugate can be administered once every three months. In some embodiments, the conjugate can be administered once every 6 months. In some embodiments, the conjugate can be administered once a year.

The conjugates useful in the method of treating an ocular disease or disorder can have any suitable vitreous half-life. For example, the vitreous half-life of the conjugate can be at least about 2-fold, at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 200-fold, at least about 500-fold, or at least about 1000-fold, or more than 1000-fold, greater than the vitreous half-life of the biologically active polypeptide not conjugated to the biocompatible polymer. In some embodiments, the vitreous half-life of the conjugate is at least 2-fold greater than the half-life of the biologically active polypeptide not conjugated to the biocompatible polymer. In some embodiments, the vitreous half-life of the conjugate is at least 5-fold greater than the half-life of the biologically active polypeptide not conjugated to the biocompatible polymer.

VI. Methods of Joint Treatment

The present invention provides a method of treating a disease or disorder in an articular joint using a peptide-polymer conjugate of the present invention. In some embodiments, the present invention provides a method of treating a disease or disorder in an articular joint, the method comprising injecting into the articular joint an effective amount of a conjugate of the present invention.

The present invention also provides methods of treating disease and disorders of the joint tissues using the conjugates of the present invention. Examples of diseases and disorders of the joint tissues include, but are not limited to rheumatoid arthritis, wear-related osteoarthritis, age-related osteoarthritis, post-traumatic osteoarthritis, psoriatic arthritis, and aseptic implant loosening, joint effusion, ankylosing spondylitis, bursitis, gout, reactive, arthritis, synovitis, and avascular necrosis. In some embodiments, the disease or disorder is rheumatoid arthritis, wear-related osteoarthritis, age-related osteoarthritis, post-traumatic osteoarthritis, psoriatic arthritis, and aseptic implant loosening, joint effusion, ankylosing spondylitis, bursitis, gout, reactive arthritis, synovitis, or avascular necrosis.

Many polypeptides are used as drugs to attenuate immune cell function have substantial utility in treating many joint disorders. Joint tissues are particularly susceptible to injury and disease because the typical cellular responses to these assaults, i.e., upregulating of inflammatory mediators, is also a signal to encourage catabolism of articular cartilage and resorption of the underlying bone tissues. Degeneration of the articular surfaces encourages the worsening of damage to the joint tissues and further up regulation of inflammatory mediators. Over time, these mechanisms generate a feed-forward loop that results in cumulative damage to the joint tissues.

Any joint of the human or animal body can be treated using the methods and conjugates of the present invention. Representative joints include, but are not limited to, fibrous joints, cartilaginous joints, synovial joints, facet joints, synarthrosis joints, amphiarthrosis joints, and diarthrosis joints. The joints can be simple joints having two articulation surfaces, a compound joint having three or more articulation surfaces, or complex joints having two or more articulation surfaces and an articular knee or meniscus. Anatomical joints that can be treated using the conjugates and methods of the present invention include, but are not limited to, hand joints including the fingers, elbow joints, wrist joints, shoulder joints, joints of the sternum and clavicle, vertebral joints, jaw and skull joints, pelvic and hip joints, knee joints, ankle joints and foot joints including the toes. The joints can also be classified as a plane joint, ball and socket joint, hinge joint, pivot joint, condyloid joint and saddle joint. The conjugates and methods of the present invention can be used to treat the tissues of the joint, including, but not limited to, connective tissue, cartilage, articulation surfaces, synovial cavities, meniscus, and others.

Examples of drugs that are designed to attenuate immune cell function include antibodies that can interfere with Tumor Necrosis Factor-$\alpha$ and IL-1$\beta$, IL-6, or interferon-$\gamma$. Other examples include selective antibody inhibitors of T cell and B cell function. These antibodies may be monoclonal IgG antibodies, IgG antibody fragments, single chain scFv antibodies, single-domain heavy-chain VHH antibodies, or engineered antibody-like scaffolds such as adnectins, affibodies, anticalins, DARPins, and engineered Kunitz-type inhibitors. Other examples also include receptor decoys of immunomodulatory cytokines such as Tumor Necrosis Factor-$\alpha$ and IL-1$\beta$, IL-6, or interferon-$\gamma$.

One common side effect of using anti-inflammatory drugs such as those listed above is a higher risk of infection. Because they attenuate the body's immune responses, the immune system becomes impaired to fight bacteria, viruses, and parasites. Therefore, the benefits of systemic use of these drugs needs to be weighed carefully against the risks associated with systemic immune suppression. In the case of diseases where the whole body is affected by a hyperimmune disorder, such as rheumatoid arthritis, systemic use of immune attenuating drugs may be justified. However, for conditions effecting only one or a limited number of joints, the system risk of infection often does not justify the systemic use of these drugs.

As an alternative, intra-articular (IA) administration of immune modulating drugs has been proposed to prevent or inhibit the long-term effects of inflammation that are associated with osteoarthritis. However, these drugs are rapidly cleared out of the joint space and do not provide adequate duration of therapy after IA administration. After IA injection, the half-life of anti-inflammatory proteins in the synovium is short (<1.5 hours). This is evident from clinical studies where inflammation inhibitors, including infliximab and etanercept, have been administered by IA injection in humans for a variety of joint disorders. Some of these studies report a significant reduction in joint inflammation, but acknowledge that frequent (e.g. weekly) administration was required for a successful outcome. Thus, IA anti-inflammatory therapy using existing drugs would be limited by high costs and the inconvenience of frequent IA dosing. Clearly, methods to extend anti-inflammatory drug bioactivity within the synovial fluid are needed to enable this therapeutic approach for treating joint disorders.

The primary symptoms associated with joint disorders are pain, effusion, limited range of motion, and pathological remodeling of the joint anatomy. Efficacy for a treatment to treat joint disorders may include a reduction in pain as measured by a generalized assessment, such as the visual assessment score. Efficacy may also be determined based on an improved score using a system that is specific to a particular joint disorder, such as the WOMAC score for osteoarthritis, the ACR20 for rheumatoid arthritis, the Psoriatic Arthritis Quality of Life for psoriatic arthritis, or the SASSS for ankylosing spondylitis. Efficacy may also be measured using a functional output, such as an increase in pain free walking distance or an increase in the range of joint motion. Efficacy may also be measured based on radiographic evidence showing restoration of normal joint anatomy.

The methods of treating a disease or disorder in an articular joint can use a peptide-polymer conjugate of the present invention having a longer diffusion half-life than the peptide. For example, the conjugate can have a diffusion half-life of at least 2 times longer than that of the peptide, or 3, 4, 5, 6, 7, 8, 9, 10, 15, 20, 25, 30, 35, 40, 45, 50, 60, 70, 80, 90, or at least 100 times longer than that of the peptide. The diffusion half-life of the conjugate can be from about 2 to about 100 times longer than the peptide, or from about 2 to about 50, from about 10 to about 100, from about 25 to about 100, from about 50 to about 100 times longer than the peptide. In some embodiments, the diffusion half-life of the conjugate is at least about 2 times longer than the peptide. In some embodiments, the diffusion half-life of the conjugate is from about 2 to about 100 times longer than the peptide.

The methods of treating a disease or disorder in an articular joint can use a peptide-polymer conjugate of the present invention having a longer intra-articular half-life longer than the peptide. For example, the conjugate can have an intra-articular half-life that is at least 20% longer than the unconjugated peptide, or at least 50, 75, 100, 150, 200, 250, 300, 350, 400, 450, 500, 600, 700, 800, 900 or 1000% longer than the unconjugated peptide. The intra-articular half-life of the conjugate can be from about 20% to about 1000% longer than the unconjugated peptide, or from about 100% to about 1000%, or from about 100% to about 500%, or from about 100% to about 300% longer than the unconjugated peptide. In some embodiments, the intra-articular half-life of the conjugate is at least about 20% longer than the peptide.

In some embodiments, the intra-articular half-life of the conjugate is from about 20% to about 1000% longer than the peptide.

The conjugate can be administered at any suitable frequency or amount as discussed above. In some embodiments, the conjugate is injected into the articular joint no more than about once a month. In some embodiments, the conjugate is injected into the articular joint from about once a month to once every 6 months. In some embodiments, the conjugate is injected into the articular joint once every 2 months or once every 3 months.

A. Osteoarthritis

In 2015, an estimated 7.75 million Americans experienced symptoms of osteoarthritis (OA) that could be associated with a known joint injury. Post-traumatic OA (PTOA) accounts for at least 15% of all OA cases, although it is assumed many other OA diagnoses may also be related to a prior joint trauma. Due to a lack of disease modifying therapies, joint replacement surgery is often the only treatment option to eliminate the associated discomfort and restore mobility. However, PTOA is often diagnosed in younger patients, for whom joint replacement is not a viable option. Overall, the cost of treating these PTOA patients exceeds $4B in health care costs each year.

Short-term inhibition of injury-related inflammation will limit the long-term symptoms of PTOA. Many types of joint injury have been associated with PTOA, including dislocations, ligament tears, meniscal damage, and intra-articular fractures. Although the initial damage may be acute, the injury is sufficient to initiate a cascade of inflammatory mediators. The resulting chronic whole-joint inflammation can encourage catabolism of the articular cartilage, resulting in further tissue damage that accumulates over time and presents as PTOA. TNFα and IL-1β have well-known roles in mediating joint inflammation. These cytokines interact to promote destruction of cartilage, which occurs by both downregulating the expression of the cartilage matrix components and upregulating the expression of matrix metalloproteinases (MMPs). TNFα also stimulates osteoclast recruitment, and induces apoptosis of bone-forming osteoblasts in inflammatory environments, which contributes to the erosion of articular cartilage tissues. TNFα and IL-1β are compelling targets for mitigating the inflammatory response to joint injury. Inhibiting these key acute inflammatory cytokines in the joint environment has been proposed for early intervention to stall the progression of PTOA.

B. Inflammation Due to Immune Response to Intra-Articular Microparticles

Wear occurring between the articular surfaces of a joint can generate particles at the micron scale that drive joint inflammation and osteolysis. Wear particles may be generated due to abrasion between endogenous surfaces, such as ossified cartilage lesions, osteophytes (bone spurs), or exposed subchondral bone lesion. This type of wear particle generation occurs frequently in later stage of OA, resulting in severe joint pain and immobility. This additional inflammatory response accelerates the rate of joint tissue degeneration in OA.

Wear particles may also be formed between the surfaces of an artificial joint. In 2015, more than 7 million Americans were living with an implanted artificial joint. Nearly 250,000 of these individuals will eventually require a revision surgery due to osteolysis of the bone surrounding the device, eventually resulting in device loosening and failure.

Wear-related inflammation stems from the foreign body response to otherwise inert microparticles shed from the articulating surfaces. Macrophages inside the synovial lining readily recognize wear microparticles as foreign bodies, release pro-inflammatory factors that recruit other active immune cells to the synovium, and stimulate osteoclast expansion while simultaneously inhibiting bone formation. Thus, sustained inflammation triggers a feed-forward cycle where cartilage degeneration and osteolysis leads to more abrasions between articulating surfaces and more movement and physical stress that in turn produces more particles.

In some embodiments, the peptide modulates the activity of immune cell function. In some embodiments, the peptide inhibits tumor necrosis factor-α, interleukin-1β, interleukin-6, or interferon-γ. In some embodiments, the peptide inhibits tumor necrosis factor-α.

Tumor necrosis factor (TNFα) is a compelling target for controlling the foreign body response. TNFα has a well-known role in mediating joint inflammation. TNFα also stimulates osteoclast recruitment, and induces apoptosis of bone-forming osteoblasts in inflammatory environments, leading to osteolysis of subchondral bone. Inhibition of TNFα using a systemically-administered receptor antagonist (etanercept) has been shown to reduce bone resorption induced by wear particles in mice, although the risks associated with systemic anti-TNFα are not generally regarded as acceptable for localized conditions. As an alternative, IA anti-TNFα therapy has been proposed to prevent or inhibit the osteolytic response to intra-articular wear particle In some embodiments, the peptide is a monoclonal IgG antibody, an IgG antibody fragment, a single-chain variable region antibody, a single-domain heavy chain antibody, an adnectin, an affibody, an anticalin, a DARPin, a Kunitz-type inhibitor, or a receptor decoy.

The methods of the present invention include a peptide-polymer conjugate comprising a biocompatible polymer having a molecular weight of from about 0.1 MDa to about 2 MDa; and a plurality of peptides each having a molecular weight of from about 5 kDa to about 100 kDa, wherein each peptide is covalently linked to the polymer, wherein there is from about 50 kDa of polymer to about 5 kDa of polymer for every peptide, and wherein the molar ratio of peptides to polymer is at least 5:1.

In some embodiments, the conjugate comprises a peptide having the CDRs according to SEQ ID NO:3 to SEQ ID NO:5:

```
                              (SEQ ID NO: 3)
DHSGYTYTIG,

                              (SEQ ID NO: 4)
ARIYWSSGNTYYADSVKG,
and

                              (SEQ ID NO: 5)
RDGIPT.
```

In some embodiments, the conjugate comprises a peptide having an amino acid sequence according to SEQ ID NO:1:

```
                                    (SEQ ID NO: 1)
QVQLQESGGGLVQPGGSLRLSCAASGRTFSDHSGYTYTIGWFRQAPGKER

EFVARIYWSSGNTYYADSVKGRFAISRDIAKNTVDLTMNNLEPEDTAVYY

CAARDGIPTSRSVESYNYWGQGTQVTVSS.
```

In some embodiments, the conjugate comprises a peptide having an amino acid sequence according to SEQ ID NO:2:

```
                                    (SEQ ID NO: 2)
SNAQVQLQESGGGLVQPGGSLRLSCAASGRTFSDHSGYTYTIGWFRQAPG

KEREFVARIYWSSGNTYYADSVKGRFAISRDIAKNTVDLTMNNLEPEDTA

VYYCAARDGIPTSRSVESYNYWGQGTQVTVSSSPSTPPTPSPSTPPGGC.
```

The conjugates of the present invention are well-positioned to ameliorate inflammation that occurs near joint to inhibit subsequent cartilage degeneration and osteolysis. These conjugates have been designed to exhibit biophysical attributes that are matched to the macromolecules of the synovial fluid that is retained within the joint. In addition, conjugating multiple copies or the bioactive polypeptide is sufficient to increase their potency by engaging multivalent interactions with their targets. Thus, this invention is well suited to enable methods of administering long-acting drugs locally to articulating joints for the treatment of various diseases.

One example target market for bioconjugates drugs is the ~25% patients of patients who experience chronic inflammation and effusion following joint injury and are thus at risk for developing PTOA. Options for these patients are currently limited to systemic analgesia and local corticosteroid treatment. Failure to resolve the prolonged inflammatory phase can lead to catabolism of articular cartilage and result in further injury that accumulates over time. A treatment based on anti-inflammatory bioconjugates and designed for administration every three months (or even less frequently) could mitigate the effect of long-term joint inflammation, thereby reducing pain and delaying or preventing the need for costly surgeries. These benefits would likely outweigh the downsides of repeated IA injections (as many as 4 per year), which may include risk of infection, inconvenience for the patient, and procedure costs.

Another example target market for bioconjugates drugs are patients who experience chronic inflammation and pain due to the development of calcified cartilage lesions, bone spurs, or subchondral bone lesions. Although surgical repair may eliminate the acute cause of the pain, existing inflammation, inflammation due to surgery, and inflammation to additional wear particles will accelerate joint damage and degeneration. Long-term options for these patients are currently limited to systemic analgesia and local corticosteroid treatment. Failure to resolve the prolonged inflammatory phase can lead to failure of the articulating surface, which requires joint replacement surgery to return the patient back to physical activity. A treatment based on anti-inflammatory bioconjugates and designed for administration every three months (or even less frequently) could mitigate the effect of long-term joint inflammation, thereby reducing pain and delaying or preventing the need for costly surgeries. These benefits would likely outweigh the downsides of repeated IA injections (as many as 4 per year), which may include risk of infection, inconvenience for the patient, and procedure costs.

Another example target market for bioconjugates drugs is the ~25% of patients with artificial joints who experience pain and effusion following joint replacement but do not demonstrate evidence of peri-implant infection to account for these symptoms. Options for these patients are currently limited to analgesia and clinical monitoring until subsequent osteolysis leads to device failure. A treatment based on anti-inflammatory bioconjugates designed for administration every three months or less frequent administration could mitigate the response to wear particles, thereby reducing pain and delaying or preventing the need for costly revision surgeries. These benefits would likely outweigh the downsides of chronic IA injections (as many as 4 per year), which may include risk of infection, inconvenience for the patient, and procedure costs.

Multivalent antibody conjugates are well-positioned to ameliorate inflammation that occurs due to joint injury or exposure to wear particles and inhibit the subsequent catabolic tissue damage. In addition to exhibiting high potency, the conjugates can be engineered with specific macromolecular properties will be retained within the joint. By conjugating an anti-inflammatory peptide to HyA that is sufficiently large to be retained with the synovium, the bioactive half-life of the conjugated antibody may be significantly extended compared to equivalent unconjugated antibodies.

VII. Examples

Abbreviations

HA/HyA: hyaluronic acid

EMCH: N-ε-maleimidocaproic acid hydrazide

MP2H: 1-[3-({[2-(3-Hydrazino-3-oxopropoxy)ethoxy]methyl}amino)-3-oxopropyl]-1H-pyrrole-2,5-dione MP77H (MP3400H): Maleimide $PEG_{77}$ Hydrazide, Maleimide 3.4 kDa PEG-CO—NHNH2

BMPH: N-(β-maleimidopropionic acid) hydrazide

MHPH: 5-Maleimido-2-hydraziniumpyridine hydrochloride n-AEM: n-aminoethylmaleimide APN-PEG4-amine: 3-{p-[3-(2-{2-[2-(2-Aminoethoxy)ethoxy]ethoxy}ethoxy)propionylamino]phenyl}propiolonitrile APN-amine: 3-(p-Aminophenyl)propiolonitrile APN-C4-amine-3-[p-(4-Aminobutyrylamino)phenyl]propiolonitrile MP2A: 1-(3-{$^2$-[2-(3-Hydrazino-3-oxopropoxy)ethoxy]ethylamino}-3-oxopropyl)-1H-pyrrole-2,5-dione or Maleimide-$PEG_2$-amine MP3A: 1-[3-(2-{2-[2-(2-Aminoethoxy)ethoxy]ethoxy}ethylamino)-3-oxopropyl]-1H-pyrrole-2,5-dione sNHS: N-hydroxysulfosuccinimide HOBt: hydroxybenzotriazole MVP: multivalent peptide polymer conjugate

Materials and Methods

The peptides and conjugates of the present invention can be prepared according to the methods described in WO 2017/100470 and PCT Application No. PCT/US19/21460 (WO2019/173777), each of which is incorporated herein in its entirety.

Example 1. Modification of Hyaluronic Acid with Hydrazide Linkers

To obtain diacylhydrazine linked heterobifunctional crosslinker modification of hyaluronic acid or other acid containing sugar aiming for a thiol reactive valency of ~10-400 (depending on crosslinker), suspend 830 kDa hyaluronic acid in 0.1 M 2-(N-morpholino)ethanesulfonic acid buffer pH 5.7 at 4 mg/mL by gentle rotation or mixing with nutation overnight at RT. To 3 mg (3.6 nmol, amount will vary based on polymer composition and MW) of HA in solution is added 50-500 equivalents hydroxybenzotriazole (HOBt) hydrate or N-hydroxysulfosuccinimide (s-NHS) as a 5-20 mg/mL stock solution in DMSO or buffer, followed by 50-1000-equivalents of hydrazide-X-thiol reactive linker in DMSO or buffer (10-25 mg/mL stock), and finally 9500 equivalents of 1-ethyl-3-(3-dimethylaminopropyl)carbodiimide hydrochloride (EDC) as a 1 g/mL stock in 0.1 M MES buffer pH 5.7 and bring final volume to 1 mL with buffer. Mix with gentle pipetting between each reagent addition. React at room temperature for 2 h with nutating mixer. After 2 h, purify the thiol reactive biopolymer using 7 kDa MWCO 5 mL Zeba desalting spin column equilibrated with 10% v/v glycerol pH 6.5 DPBS 0.01% v/v polysorbate 20. Elute product into clean conical tube using centrifuge at RT, elution time ~25-45 minutes. Use immediately for reaction with thiol or aliquot and flash freeze on dry ice.

Alternatively, reaction pH or equivalents of hydrazide linker, HOBt or sNHS, and EDC can be altered higher or lower in order to increase or decrease the number of thiol reactive small molecule linkers covalently linked per biopolymer (valency). Activated biopolymer intermediate can also be purified away from reactants using size exclusion chromatography, other desalting columns, tangential flow filtration, ion exchange chromatography, dialysis, or alcohol/acetone precipitation. Linkers that are >1000 Da will not be able to be purified by desalting and will require one of the other methods listed above.

TABLE 1

Intermediates

| Intermediate | Linker | HOBt eq. | Linker eq. | EDC eq. | [Maleimide] (μM) | Maleimide Valency assuming no HA loss | Linker reaction efficiency based on valency |
|---|---|---|---|---|---|---|---|
| 1 | EMCH | 50 | 500 | 9500 | 777.6 | 206 | 41% |
| 2 | EMCH | 50 | 500 | 9500 | 656.9 | 192 | 38% |
| 3 | BMPH | 50 | 500 | 9500 | 825.2 | 202 | 40% |
| 4 | MP2H | 50 | 500 | 9500 | 349 | 90 | 18% |
| 5* | EMCH | 500 | 1000 | 9500 | 638 | 204 | 20% |
| 6 | MP77H | 50 | 500 | 9500 | 172 | 62 | 12% |
| 7** | MHPH | 50 | 500 | 9500 | | | 0% |
| 8 | MP2H | 50 | 500 | 9500 | 227 | 83 | 17% |
| 9 | EMCH | 50 | 500 | 9500 | 520 | 179 | 36% |
| 10 | EMCH | 50 | 500 | 9500 | 810.75 | 252 | 50% |
| 11 | MP2H | 50 | 500 | 9500 | 155.17 | 49 | 10% |
| 12 | BMPH | 50 | 500 | 9500 | 806.42 | 258 | 52% |
| 13 | MP2H | 50 | 500 | 9500 | 177.5 | 48 | 10% |
| 14 | MP2H | 50 | 1000 | 9500 | 353.19 | 93 | 9% |
| 15 | MP2H | 50 | 1000 | 9500 | 476 | 137 | 14% |
| 16 | EMCH | 50 | 250 | 9500 | 418 | 122 | 49% |
| 17 | MP2H | 50 | 100 | 9500 | 44.49 | 13 | 13% |
| 18 | MP2H | 50 | 250 | 9500 | 96.81 | 30 | 12% |
| 19 | MP2H | 50 | 500 | 9500 | 219.12 | 67 | 13% |
| 20 | MP2H | 50 | 1000 | 9500 | 399.64 | 138 | 14% |
| 21 | EMCH | 50 | 50 | 9500 | 93.5 | 28 | 56% |
| 22 | EMCH | 50 | 100 | 9500 | 178.3 | 54 | 54% |
| 23 | EMCH | 50 | 250 | 9500 | 380.3 | 115 | 46% |
| 24 | EMCH | 50 | 500 | 9500 | 709.7 | 208 | 42% |
| 38 | MP2H | 50 | 500 | 9500 | 236 | 72 | 14% |
| 39 | EMCH | 50 | 500 | 9500 | 811 | 248 | 50% |
| 40 | EMCH | 50 | 500 | 9500 | | | |
| 41 | MP2H | 50 | 500 | 9500 | | | |
| 42*** | MP2H | 50 | 500 | 9500 | 827 | 171 | |

*Denotes use of sNHS in reaction.

**denotes product gelled upon thawing.

***denoted valency and maleimide concentration determined by UV.

TABLE 2

Intermediates

| Intermediate | Linker | Maleimide Valency |
|---|---|---|
| 30 | MP3A | 30 |
| 28 | n-AEM | 27 |
| 5 | EMCH | 204 |
| 6 | MP77H | 62 |
| 7 | MHPH | ND |
| 29 | APN-C4-amine | 66 |
| 31 | MP2A | 44 |
| 4 | MP2H | 90 |

Example 2. Modification of Hyaluronic Acid with Amine Linkers

To obtain amide linked heterobifunctional crosslinker modification of hyaluronic acid or other acid containing sugar, aiming for a thiol reactive valency of ~2-200 (depending on crosslinker), suspend 830 kDa hyaluronic acid in 0.1 M 2-(N-morpholino)ethanesulfonic acid buffer pH 6.5 at 4 mg/mL by gentle rotation or mixing with nutation overnight at RT. To 3 mg (3.6 nmol) of HA in solution is added 9500 equivalents of 1-ethyl-3-(3-dimethylaminopropyl)carbodiimide hydrochloride (EDC) as a 1 g/mL stock in 0.1 M MES buffer pH 6.5, followed by 50-500 equivalents N-hydroxysulfosuccinimide (sNHS) or hydroxybenzotriazole (HOBt) hydrate as a 5-20 mg/mL stock solution in buffer or DMSO, and finally 1000 equivalents of amine-X-thiol reactive linker in DMSO (10-25 mg/mL stock) or 1:1 DMSO:0.1 M sodium bicarbonate for HCl salt, and bring final volume to 1 mL with buffer. Mix with gentle pipetting between each reagent addition. React at room temperature for 2 h with nutating mixer. After 2 h, purify the thiol reactive biopolymer using 7 kDa MWCO 5 mL Zeba desalting spin column equilibrated with 10% v/v glycerol pH 6.5 DPBS 0.01% v/v polysorbate 20. Elute product into clean conical tube using centrifuge at RT, elution time ~25-45 minutes. Use immediately for reaction with thiol or aliquot and flash freeze on dry ice.

Alternatively, equivalents of amine linker, HOBt or sNHS, and EDC, along with reaction pH, can be altered higher or lower in order to increase or decrease the number of thiol reactive small molecule linkers covalently linked per biopolymer (valency). Activated biopolymer intermediate can also be purified away from reactants using size exclusion chromatography, other desalting columns, tangential flow filtration, ion exchange chromatography, dialysis, or alcohol/acetone precipitation.

TABLE 3

| Intermediates | | | | | | | |
|---|---|---|---|---|---|---|---|
| Intermediate | Linker | sNHS eq. | Linker eq. | EDC eq. | [Maleimide] (μM) | Maleimide Valency assuming no HA loss | Linker reaction efficiency based on valency |
| 26* | n-AEM | 50 | 500 | 9500 | 96.8 | 27 | 5% |
| 27 | MP3A | 500 | 1000 | 9500 | 182 | 59 | 6% |
| 28 | n-AEM | 500 | 1000 | 9500 | 389 | 99 | 10% |
| 29 | APN C4 amine | 500 | 1000 | 9500 | 180 | 55 | 6% |
| 30 | MP3A | 500 | 1000 | 9500 | 85 | 30 | 3% |
| 31 | MP2A | 500 | 1000 | 9500 | 151 | 44 | 4% |
| 32 | APN PEG4 amine | 500 | 1000 | 9500 | 220 | 55 | 6% |
| 33 | APN amine | 500 | 1000 | 9500 | 15 | 5 | 1% |
| 34 | n-AEM | 500 | 1000 | 9500 | 102.8 | 24 | 2% |
| 35 | MP2A | 500 | 1000 | 9500 | 146.87 | 47 | 5% |
| 36 | n-AEM | 500 | 1000 | 9500 | 144.7 | 45 | 5% |
| 37 | MP3A | 500 | 1000 | 9500 | 127.02 | 42 | 4% |

*Denotes reaction ran with HOBt

Example 3. Linker Per Biopolymer Determination Using UV Absorbance Spectrum or Ellman's Reaction The average number of linkers covalently attached to the biopolymer backbone on a per biopolymer basis (valency) was determined by taking the UV spectra of purified, activated intermediate samples. A 1200 μM linker solution in the same buffer the final activated intermediate will be purified into was made and serial diluted one to one six times for a total of seven samples and a blank. The UV spectra is collected of each standard (200-324 nm, 2 nim step) using Biotek take 3 trio plate as a sample holder, analyzing samples in duplicate or quadruplicate. The slope of the standard curve generated by this data will give the product of molar absorptivity and pathlength for the linker in appropriate buffer across any wavelength of interest. A second UV spectra standard curve was generated using the biopolymer (i.e. 4 mg/mL 830 kDa hyaluronic acid, high purity) in same buffer using the buffer the final activated intermediate will be purified into. This solution was serial diluted one to one six times for a total of seven samples and a blank. The UV spectra is collected of each standard (200-324 nm, 2 nm step) using Biotek take 3 trio plate as a sample holder, analyzing samples in duplicate or quadruplicate. The slope of the standard curve generated by this data will give the product of molar absorptivity and pathlength for the biopolymer in appropriate buffer at different wavelengths. The plot of each of these solutions' absorbance values at 204 nm and 230 nm vs concentration was used to determine molar absorptivity*pathlength for the two molecules, where the absorptivity for the biopolymer is essentially zero 230 nm. Unknown samples must be in same buffer used to generate standard curves. The absorbance values at 204 and 230 nm were determined for unknown intermediates. This data was used to calculate unknown linker and biopolymer concentrations for Zeba purified intermediates by first calculating the linker concentration using the 230 nm standard curve generated for the linker. This concentration was then used to calculate the absorbance contribution of the linker at 204 nm. The difference between the total absorbance at 204 and the absorbance contribution from the linker at 204 nm was used to calculate the biopolymer concentration. From this information the v total number of covalently bound linkers per biopolymer or valency can be approximated, but this does not give information on the number of intact/thiol reactive maleimides.

Additionally, the number of thiol reactive groups per polymer can be calculated using a modified version of the colorimetric Ellman's assay. N-ethylmaleimide (NEM) standards was made using six 1:1 serial dilutions of a 400 μM NEM stock and these solutions were added to a well plate in triplicate. Thiol reactive intermediate samples were prepared in triplicate using two dilutions for six replicates per sample. Sodium 2-mercaptoethanesulfonate (MESNA) was added to all samples at a final concentration of 400 μM and the reaction was allowed to proceed 2 h at RT with orbital shaking (~200 rpm). After this time, Ellman's reagent (5,5-dithio-bis-(2-nitrobenzoic acid) was added to each sample for a final concentration of 0.5 mg/mL to initiate a colored product resulting from Ellman's reagent reaction with unreacted MESNA. The Ellman's reaction was allowed to proceed for 15 min with orbital shaking, after which the plate was analyzed for absorbance at 412 nm. The NEM standard curve allows for calculation of thiol reactive molecules, assuming that the molecules react with thiols at the same rate as NEM.

TABLE 4

| Linker Valency | | | |
|---|---|---|---|
| Intermediate | Thiol reactive linker | Linker Valency (UV) | Intact maleimide valency (Ellman's) |
| 1 | EMCH | 315 | 206 |
| 3 | BMPH | | 204 |
| 38 | MP2H | 170 | 72 |
| 27 | MP3A | 150 | 59 |
| 26 | n-AEM | 77 | 23 |
| 7 | MHPH | Gelled | Gelled |
| 101 | MP2H | 143 | 109 |
| 102 | MP3A | | 48 |
| 103 | MP3A | 149 | 51 |
| 29 | Amine-C4-APN | | 46 |

Example 4. Purity Determination

UV absorbance spectra were used to determine intermediate purity after subsequent Zeba purifications and to determine the number of Zeba spin column purifications needed to remove all reactants/byproducts from the activated biopolymer. Spectra from crude reaction mixtures were compared to spectra of samples after one or two Zeba purification column passes. The UV spectra for one and two Zeba pass samples overlaid identically, demonstrating that the spectra were the same and no change occurred between the first and second Zeba purification step. This confirmed that there was no change in UV signal of intermediate between $1^{st}$ and $2^{nd}$ Zeba spin column pass using 0.5 mL Zeba column, to demonstrate that one Zeba purification is enough to remove reactants from intermediate synthesis. Reverse phase HPLC can also be used to asses purity of intermediates. A reverse phase HPLC analysis of intermediate before and after Zeba column purification was performed using either an Agilent AdvanceBio RP-mAb-SB-C8 or Phenomenex Onyx Monolithic C18 column and a mobile phase consisting of a gradient of acetonitrile 0.1% TFA in 60 mM ammonium formate, which allowed for sufficient separation between product and reactant/reaction byproduct peaks. HPLC seems to show that there may be residual reactant (likely EDC) in small amounts but this needs to be further verified.

Example 5. Preparation of Peptide-Polymer Conjugates

To obtain bioconjugates with peptides conjugated to a range of intermediates synthesized using different small molecule linkers, a fixed concentration of peptide was combined with the polymer in PBS targeting ~0.5-2 protein equivalents per maleimide or targeting a fixed number of peptides per polymer and allowed to react at either 4° C. or ambient temperature for at least 4 and 2 hours respectively with rotation or nutating mixing (most reactions are ran at RT to improve solubility). In some cases before the conjugation reaction, 10-100 equivalents of a reducing agent such as DTT or TCEP HCl can be added per protein equivalent to reduce any disulfide bringing between peptides. This can be removed from the protein solution prior to conjugation by a desalting column or buffer exchange or can be added to the conjugation reaction directly in the form of TCEP immobilized on polymeric beads. During the conjugation reaction, one or more of the following was added to improve the reaction efficiency: 0.5-10 mM EDTA to minimize free thiol oxidation, tween20, carbohydrate, cosolvent, or glycerol to stabilize protein and/or help reduce non-specific interactions between protein and activated biopolymer, increased or decreased salt concentration to stabilize protein and/or help reduce non-specific interactions between protein and activated biopolymer. Unreacted peptide was removed from the peptide-polymer conjugates by one or more of the following methods: dialysis with 50-1000 kDa MWCO against an appropriate buffer (pH should be >1 unit above or below the pI of peptide) for two times for 4 hours each and once for at least 4 hours at 4° C.-room temperature, tangential flow filtration against DPBS pH 6-8, or 50 mM tris 150 mM NaCl pH 8-8.5 with EDTA and tween or other additives like trehalose, depending on peptide, FPLC polishing using a size exclusion column, FPLC polishing with an affinity chromatography column designed to bind the polymer component of the conjugate, or selective precipitation of the conjugates. If reaction efficiency is high enough (e.g., <4% unreacted protein present) purification may not be necessary.

Alternatively, to each solution of activated polymer, the peptide was added at a suitable peptide:polymer molar feed ratio and Tween-20 to a final concentration of 0.01%. The solution was allowed to react for 2 hours while agitating by rotation (~5 RPM) or nutation at ambient temperatures. Unreacted peptides were removed by were removed by dialysis using 100 kDa MWCO membranes against each of the following buffer solutions in sequence: First, phosphate buffered saline or equivalent tris buffered saline (pH depends on peptide) with 0.01% Tween-20 for at least 4 hours, second phosphate buffered saline with 0.01% Tween-20 overnight, and phosphate buffered saline with 0.01% Tween-20 for 4 hours at 4° C. or RT. Additives like tween20, EDTA, and carbohydrates can be added to enhance protein stability.

For peptide-polymer conjugate formation using commercially available antibodies, the antibody (2-10 mg/mL) was first activated with 5-20 molar equivalents of 2-iminothiolane (Traut's reagent) in order to generate free thiols on the antibody surface through a one hour ambient reaction at ambient with nutation. The activated antibody was purified using 0.5 mL 7 kDa MWCO Zeba columns. Thiol displaying antibodies can also be generated by partial or full reduction of the antibody using a reducing agent such as TCEP. After purification, the activated antibody was mixed with the EMCH or MP2H intermediate at 0.5-2 equivalents per maleimide and allowed to react at ambient for 2-3 hours mixing with nutation. The antibody conjugate reaction was then diluted to 800 L and purified using 1000 kDa MWCO dialysis cassette and dialyzed against an appropriate buffer (pH should be >1 unit above or below the pI of peptide) for two times for 4 hours each and once for at least 4 hours at 4° C.-room temperature. Alternate purification strategies are tangential flow filtration against DPBS pH 6-8, or 50 mM tris 150 mM NaCl pH 8-8.5 with EDTA and tween or other additives like trehalose, depending on peptide, FPLC polishing using a size exclusion column, FPLC polishing with an affinity chromatography column designed to bind the polymer component of the conjugate, or selective precipitation of the conjugates. If reaction efficiency is high enough (e.g., <4% unreacted protein present) purification may not be necessary.

To synthesize conjugates containing low molecular weight peptides (<5000 Da; see SEQ ID NO:20), the peptides were brought up in DMSO:buffer mixes to 10 mg/mL, reduced using 20 equivalents (TCEP) for 60 minutes at RT to produce free thiols or reduced using TCEP bound on beads for ease of purification of peptides <1500 Da. The peptides reduced with soluble TCEP were purified using 0.5 mL 7 kDa MWCO Zeba desalting columns. The purified activated peptides were mixed with intermediates at a ratio of 2-5 peptide equivalents per maleimide and allowed to react at RT for 2 h. In some cases, 0.5 equivalents of TCEP per peptide were added to keep the peptides containing disulfides from crosslinking through disulfide formation between two peptides or reaction of one peptide with two different polymer intermediates. Unreacted peptide was removed from the peptide-polymer conjugates by one or more of the following methods: dialysis with 50-100 kDa MWCO against an appropriate buffer (pH should be >1 unit above or below the pI of peptide, and may require a cosolvent like DMSO to keep conjugate soluble) for two times for 4 hours each and once for at least 4 hours at 4° C.-room temperature, desalting column with 40 kDa MWCO, tangential flow filtration against DPBS pH 6-8, or 50 mM tris 150 mM NaCl pH 8-8.5 with EDTA and tween or other additives like trehalose or cosolvents, depending on peptide, FPLC polishing using a size exclusion column, FPLC polishing with an affinity chromatography column designed to bind the polymer component of the conjugate, or selective precipitation of the conjugates. If reaction efficiency is high enough (e.g., <4% unreacted protein present) purification may not be necessary.

Verification of conjugation was determined using either SDS PAGE or HPLC size exclusion chromatography (SEC) to assess conjugate formation and percent unreacted protein after purification. Densitometry against a standard curve was used to quantify unreacted monomer in SDS PAGE analysis of purified conjugates stained with Coomassie blue or a fluorescent stain like SYBR Ruby. SEC peak areas at 280 nm were used to determine percent unreacted protein that remained the purified conjugates. For SEC, the conjugate was filtered prior to analysis to remove particles and analyzed using a Shodex OHpak LB-804 or 806 column or Phenomenex PolySep-6000 with DPBS as the mobile phase to get baseline trace at 280 nm. Additionally, SEC can be combined with multiangle light scattering (MALS) to determine the purified peptide-polymer conjugate radius of gyration and molecular weight.

The sequences were prepared accordingly to standard methods, obtained from various commercial sources, or provided by third parties. For example, SEQ ID NO:18 and SEQ ID NO:19 were provided by Hybrigenics Services.

TABLE 5

Reaction Efficiency of Conjugates

| Protein | Linker | Intermediate | Conjugate number | Peptide conc (mg/mL) | Valency | Conjugate Reaction Efficiency (including monomeric VHH) |
|---|---|---|---|---|---|---|
| aVEGF BI VHH | EMCH | 1 | 1* | 0.08 | 14 | 13% |
| aVEGF BI VHH | EMCH | 2 | 2* | ND | ND | ND |
| aVEGF BI VHH | BMPH | 3 | 3* | ND | ND | ND |
| aVEGF BI VHH | MP2H | 4 | 4 | 0.38 | 72 | 68% |
| aVEGF BI VHH | MP3A | 25 | 5 | 0.17 | 35 | 33% |
| aVEGF BI VHH | n-AEM | 26 | 6 | 0.26 | 50 | 48% |
| aVEGF DARPin | MP2H | 8 | 7 | 0.75 | 22 | 29% |
| aVEGF DARPin | MP3A | 30 | 8 | 0.27 | 6 | 23% |
| aVEGF DARPin | MP2A | 31 | 9 | 0.45 | 12 | 23% |
| aVEGF DARPin | EMCH | 9 | 10 | 0.46 | 18 | 12% |
| aVEGF E1-1 VHH | EMCH | 9 | 11 | 0.6 | 104 | 58% |
| aVEGF E1-1 VHH | MP2H | 8 | 13 | 0.46 | 51 | 62% |
| aVEGF E1-1 VHH | MP3A | 30 | 14 | 0.29 | 29 | 97% |
| aVEGF E1-1 VHH | MP2A | 31 | 15 | 0.27 | 28 | 64% |
| aTNFa FLAG VHH | MP2A | 35 | 16 | 0.89 | 22 | 47% |
| aTNFa FLAG VHH | n-AEM | 36 | 17 | 0.96 | 23 | 51% |
| aTNFa FLAG VHH | MP3A | 37 | 18 | 1.03 | 23 | 55% |
| aTNFa FLAG VHH | EMCH | 10 | 19 | 0.42 | 28 | 11% |
| aTNFa FLAG VHH | MP2H | 11 | 20 | 1.23 | 30 | 61% |
| aTNFa FLAG VHH | BMPH | 12 | 21 | 0.44 | 30 | 12% |
| aTNFa FLAG VHH | MP2H | 13 | 22 | 0.95 | 29 | 60% |
| aTNFa FLAG VHH | MP2H | 14 | 23 | 1.76 | 77 | 83% |
| G5-1 aVEGF VHH | MP2H | 15 | 24 | 0.372 | 52 | 74% |
| G5-1 aVEGF VHH | EMCH | 16 | 25 | 0.411 | 53 | 75% |
| aEGFR VHH | MP3A | 27 | 26 | 1.83 | 62 | 39% |
| aEGFR VHH | n-AEM | 28 | 27 | 1.92 | 68 | 43% |
| aEGFR VHH | EMCH | 5 | 28* | 0.35 | 7 | 4% |
| aEGFR VHH | APN C4 amine | 29 | 29 | 1.16 | 22 | 14% |
| aVEGF DARPin | MP2H | 38 | 30 | 1.07 | 50 | 74% |
| aVEGF DARPin | EMCH | 39 | 31*** | 1.07 | <179 | <72% |
| aVEGF DARPin | MP2H | 42 | 40 | 1.33 | 68 | 97% |
| Cy7-aVEGF DARPin | MP2H | | 41**** | 0.52 | 45 | 50% |

*Denotes reaction that precipitated during conjugate formation.

**Denotes viscous product that took >2x as long to filter.

***Denotes high percentage (>70%) of unreacted protein skewing valency and reaction efficiency.

****Denotes fluroescently tagged protein.

Example 6. Peptide-Polymer Binding Affinity

Binding affinity verification of the conjugates' bioactivity can be determined using one or more of the following methods. One example, BioLayer interferometry (BLI;

ForteBio Octet Red) was used to determine the binding affinity of each peptide and peptide-polymer conjugate to the target. Target peptides modified with biotin are adsorbed onto a glass BLI probe covalently modified with streptavidin surface layer. The probe with bound target molecules are then placed in solutions containing known concentrations of either the peptide-polymer conjugate or peptide alone. Laser light is passed down the length of the BLI probe, and the interference generated by the peptide or conjugate binding to the target on the probe tip can be correlated directly to the mass of peptide or conjugate bound. The k-on binding constant can be determined by collecting the interference data over time during target binding. The probe is then placed in a solution of buffer without conjugate or peptide. As the peptide or conjugate dissociate from the BLI probe, the laser light interference will reverse allowing for the calculation of the k-off constant. Together, this method allows BLI to measure the binding affinity ($k_d$) for each peptide and conjugate to its target.

Another example method for determining conjugate binding are using a plate-based colorimetric ELISA or cell-based assays such as DiscoverX assay (EuroFins). In the DiscoverX assay, target peptide (i.e VEGF) binds to a modified cell surface receptor resulting in receptor dimerization that activates an enzyme. This enzyme allows for quantitation of peptide binding by chemiluminescence. The conjugate or peptide of interest is incubated in a solution containing the cells and target peptide. Competitive binding between the target peptide and either the cell receptor or conjugate/peptide of interest results in varying degrees of receptor activation within the cells. The strength of binding and dissociation constants are quantified by addition of the chemiluminescent substrate and the resulting intensity of the chemiluminescence is collected and correlated to the amount of free target peptide available to dimerize the cell surface receptors, allowing for calculation of EC50/IC50. Generally, better bioactivity is observed for conjugates synthesized using hydrophilic linkers. In all cases, the peptide polymer conjugate has improved binding kinetics compared to unreacted protein.

TABLE 6

BLI Dissociation Constant of Conjugates

| Protein | Linker | Intermediate | Conjugate number | Protein conc (mg/mL) | Protein Valency | Dissociation constant by BLI (nM) |
|---|---|---|---|---|---|---|
| aVEGF BI VHH | EMCH | 1 | 1* | 0.08 | 14 | |
| aVEGF BI VHH | EMCH | 2 | 2* | ND | ND | |
| aVEGF BI VHH | BMPH | 3 | 3* | ND | ND | |
| aVEGF BI VHH | MP2H | 4 | 4 | 0.38 | 72 | 0.011 |
| aVEGF BI VHH | MP3A | 25 | 5 | 0.17 | 35 | |
| aVEGF BI VHH | n-AEM | 26 | 6 | 0.26 | 50 | 0.012 |
| aVEGF DARPin | MP2H | 8 | 7 | 0.75 | 22 | <0.001 |
| aVEGF DARPin | MP3A | 30 | 8 | 0.27 | 6 | 5.99 |
| aVEGF DARPin | MP2A | 31 | 9 | 0.45 | 12 | 1.381 |
| aVEGF DARPin | EMCH | 9 | 10 | 0.46 | 18 | 0.397 |
| aVEGF E1-1 VHH | EMCH | 9 | 11 | 0.6 | 104 | 1.763 |
| aVEGF E1-1 VHH | MP2H | 8 | 13 | 0.46 | 51 | 0.678 |
| aVEGF E1-1 VHH | MP3A | 30 | 14 | 0.29 | 29 | 1.31 |
| aVEGF E1-1 VHH | MP2A | 31 | 15 | 0.27 | 28 | 1.918 |
| aTNFa FLAG VHH | MP2A | 35 | 16 | 0.89 | 22 | 1.335 |
| aTNFa FLAG VHH | n-AEM | 36 | 17 | 0.96 | 23 | 0.566 |
| aTNFa FLAG VHH | MP3A | 37 | 18 | 1.03 | 23 | 0.886 |
| aTNFa FLAG VHH | EMCH | 10 | 19 | 0.42 | 28 | 0.239 |
| aTNFa FLAG VHH | MP2H | 11 | 20 | 1.23 | 30 | <0.001 |
| aTNFa FLAG VHH | BMPH | 12 | 21 | 0.44 | 30 | 0.274 |
| aTNFa FLAG VHH | MP2H | 13 | 22 | 0.95 | 29 | <0.001 |
| aTNFa FLAG VHH | MP2H | 14 | 23 | 1.76 | 77 | <0.001 |
| G5-1 aVEGF VHH | MP2H | 15 | 24 | 0.372 | 52 | 0.568 |
| G5-1 aVEGF VHH | EMCH | 16 | 25 | 0.411 | 53 | 0.732 |
| aEGFR VHH | MP3A | 27 | 26 | 1.83 | 62 | |
| aEGFR VHH | n-AEM | 28 | 27 | 1.92 | 68 | |
| aEGFR VHH | EMCH | 5 | 28* | 0.35 | 7 | |
| aEGFR VHH | APN C4 amine | 29 | 29 | 1.16 | 22 | |
| aVEGF DARPin | MP2H | 38 | 30 | 1.07 | 50 | |
| aVEGF DARPin | EMCH | 39 | 31*** | 1.07 | <179 | |
| aVEGF DARPin | MP2H | 42 | 40 | 1.33 | 68 | 0.0109 |
| Cy7-aVEGF DARPin | MP2H | | 41**** | 0.52 | 45 | |

*Denotes recation that precipitated during conjugate fromation.

***Denotes high percentage of unreacted protein (<70%).

****Denotes fluorescently tagged peptide

Example 7. Stability Determination

Several methods can be used to assess MVP stability initially and with time and storage at different temperatures. Turbidity was determined via visible light absorbance/scatter at ~660-700 nm and used to compare relative stabilities where higher turbidity indicates lower stability. Solution turbidity based on 660-700 nm absorbance increases with decreasing conjugate stability. A qualitative measure of turbidity or the presence of precipitate/aggregates was done by visual analysis. In many cases, aggregates and precipitates are visible by eye but can also be analyzed via microscope images or light scattering methods, which can be used to verify aggregation and assess aggregate size.

Stability and initial conjugate size was also assessed using HPLC size exclusion chromatography (SEC). This method was also used to analyze MVP formation, relative size by retention time, and percent unreacted protein after purification. To assess stability via SEC, MVP was filtered to remove particles and analyzed using a Shodex OHpak LB-804 or 806 column or Phenomenex PolySep-6000 with DPBS as the mobile phase to get baseline trace at 280 nm. After various time points samples were removed and analyzed using the same SEC method. Increases in retention time and peak width relative to the baseline sample indicated degradation. In addition, decreases in MVP peak area and/or increases in monomer and dimer protein species peak area also indicate MVP degradation. Percent conjugate loss was quantified by comparing peak area differences with time. The SEC stability analysis has also been coupled with MALS to quantify molecular weight and valency changes of the conjugate with age at different temperatures.

TABLE 7

| Conjugate Stability | | | |
|---|---|---|---|
| Conjugate | MVP valency | MVP stability | MVP filterability |
| 1 | 14 | Precipitated mid-reaction | some loss of UV signal after filtering |
| 3 | CNA | Precipitated mid-reaction | some loss of UV signal after filtering |
| 4 | 72 | no visible precipitation | no loss of UV signal after filtering |
| 15 | 28 | no visible precipitation | no loss of UV signal after filtering |
| 5 | 35 | no visible precipitation | no loss of UV signal after filtering |
| 6 | 50 | no visible precipitation | some loss of UV signal after filtering |
| 28 | 7 | Precipitated mid-reaction | ND |
| 26 | 62 | no visible precipitation | ND |
| 27 | 68 | no visible precipitation | ND |
| 38 | 75 | no visible precipitation | some loss of UV signal after filtering |
| 39 | 18 | Precipitated mid-reaction | CNA |

TABLE 7-continued

| Conjugate Stability | | | |
|---|---|---|---|
| Conjugate | MVP valency | MVP stability | MVP filterability |
| 34 | 52 | no visible precipitation | no loss of UV signal after filtering |
| 35 | 110 | no visible precipitation | no loss of UV signal after filtering |

CNA—could not analyze
ND—not determined

Example 8. Determination of Filterability

To determine the filterability of the peptide polymer conjugates generated with various small molecule linkers, the product was subject to spin filtration (i.e. cellulose acetate, 0.22 μm) or syringe filtration. For both methods, a sample was saved pre filtration for UV analysis and spectral comparison before and after filter. For spin filtration, the sample was loaded in the spin filter undiluted, pre-concentrated using a 100 kDa MWCO spin concentrator, or diluted 1:1 with buffer and centrifuged to elute. The filtered eluent absorbance spectrum was taken and plotted over the pre filtration absorbance spectrum to check for losses using change in signal or concentration changes calculated using the peptide extinction coefficient. The percent loss was calculated based on direct protein signal at 280 nm before and after filtration, or calculated concentration before and after filtration. In some cases, the purified conjugate or conjugate reaction was diluted 1:1 prior to purification or filtration. For syringe-based filtration, the plunger was removed from small volume luer lock syringe and a 0.45-5 μm syringe filter was loaded on the luer lock syringe. The sample to be filtered was pipetted into bottom of syringe. To filter the sample the plunger was reinserted into the syringe and the sample was pushed through the filter and captured in clean tube. This process is repeated using a 0.2 μm luer lock syringe filter with fresh syringe for sterile filtration. The filtered eluent absorbance spectrum was taken and plotted over the pre filtration absorbance spectrum to check for losses. The percent loss was calculated based on protein change in protein signal at 280 nm before and after filtration.

TABLE 8

| Recovery Data for Conjugates | | | | | | |
|---|---|---|---|---|---|---|
| Protein | Linker | Intermediate | Conjugate number | Peptide conc pre filtration (mg/mL) | Protein valency | Recovery upon 0.2 μm filtration |
| aVEGF BI VHH | EMCH | 1 | 1* | 0.08 | 14 | 73% |
| aVEGF BI VHH | EMCH | 2 | 2* | ND | ND | 69% |
| aVEGF BI VHH | BMPH | 3 | 3* | ND | ND | 72% |
| aVEGF BI VHH | MP2H | 4 | 4 | 0.38 | 72 | 103% |
| aVEGF BI VHH | MP3A | 25 | 5 | 0.17 | 35 | 102% |
| aVEGF BI VHH | n-AEM | 26 | 6 | 0.26 | 50 | 83% |
| aVEGF DARPin | MP2H | 8 | 7 | 0.75 | 22 | |
| aVEGF DARPin | MP3A | 30 | 8 | 0.27 | 6 | |
| aVEGF DARPin | MP2A | 31 | 9 | 0.45 | 12 | |
| aVEGF DARPin | EMCH | 9 | 10 | 0.46 | 18 | |
| aVEGF E1-1 VHH | EMCH | 9 | 11 | 0.6 | 104 | 97% |
| aVEGF E1-1 VHH | MP2H | 8 | 13 | 0.46 | 51 | 99% |
| aVEGF E1-1 VHH | MP3A | 30 | 14 | 0.29 | 29 | 100% |
| aVEGF E1-1 VHH | MP2A | 31 | 15 | 0.27 | 28 | 95% |
| aTNFa FLAG VHH | MP2A | 35 | 16 | 0.89 | 22 | 99% |
| aTNFa FLAG VHH | n-AEM | 36 | 17 | 0.96 | 23 | 92% |
| aTNFa FLAG VHH | MP3A | 37 | 18 | 1.03 | 23 | 96% |
| aTNFa FLAG VHH | EMCH | 10 | 19 | 0.42 | 28 | 86% |
| aTNFa FLAG VHH | MP2H | 11 | 20 | 1.23 | 30 | 94% |

TABLE 8-continued

Recovery Data for Conjugates

| Protein | Linker | Intermediate | Conjugate number | Peptide conc pre filtration (mg/mL) | Protein valency | Recovery upon 0.2 µm filtration |
|---|---|---|---|---|---|---|
| aTNFa FLAG VHH | BMPH | 12 | 21 | 0.44 | 30 | 72% |
| aTNFa FLAG VHH | MP2H | 13 | 22 | 0.95 | 29 | 102% |
| aTNFa FLAG VHH | MP2H | 14 | 23 | 1.76 | 77 | 95% |
| G5-1 aVEGF VHH | MP2H | 15 | 24 | 0.372 | 52 | 97% |
| G5-1 aVEGF VHH | EMCH | 16 | 25 | 0.411 | 53 | 34% |
| aEGFR VHH | MP3A | 27 | 26 | 1.83 | 62 | |
| aEGFR VHH | n-AEM | 28 | 27 | 1.92 | 68 | |
| aEGFR VHH | EMCH | 5 | 28* | 0.35 | 7 | |
| aEGFR VHH | APN C4 amine | 29 | 29 | 1.16 | 22 | |
| aVEGF DARPin | MP2H | 38 | 30 | 2.76 | 50 | 92% |
| aVEGF DARPin | EMCH | 39 | 31*** | 3.11 | <179 | |
| aVEGF DARPin | MP2H | 42 | 40 | 1.33 | 68 | |
| Cy7-aVEGF DARPin | MP2H | | 41**** | 0.52 | 45 | 100% |

Filtration recovery for peptide-polymer conjugates filtered using 0.2 µm.
*denotes reactions that precipitated during conjugate formation.
**denotes viscous product that took >2x as long to filter.
***denotes high percentage of unreacted protein in sample (>70%).
****denotes fluorecently tagged protein

Example 9. Synthesis of High Valency Peptide-Polymer Conjugates 830 kDa HA intermediates were synthesized using either EMCH or MP2H to display a range of maleimides per HA backbone by varying the equivalents of linker to HA using the methods described above. This allowed for synthesis of anti-TNFa peptide-polymer conjugates with a varying peptide valencies using the methods described above. These conjugates were analyzed using methods listed above to assess the relationship between conjugate peptide valency/potency and handling properties, reaction efficiency, maximal achievable valency, and binding kinetics of the resulting conjugates synthesized using either a hydrophobic or hydrophilic linker.

In this experiment it was found that the EMCH product was limited in maximum achievable valency and filtration recovery compared to MP2H due to the instability of high valency peptide protein conjugates based on EMCH (max valency 75). The MP2H conjugates (max valency 110) demonstrated overall better handling properties, filterability, and reaction efficiency while also being sterilizable via filtration at higher drug loads than the EMCH. The ability to sterilize the higher valency MP2H conjugates by filtration makes MP2H an improved drug candidate compared to the EMCH conjugates with regards to production process scaling. Since high valency EMCH conjugates are unfilterable, EMCH conjugate synthesis requires time consuming sterile processing to get the highest achievable drug load, but these processes do not scale to clinical scale drug production. MP2H conjugates allow for higher peptide valencies per molecule, which provides equivalent or improved bioactivity compared to the EMCH conjugates that are limited in drug loading by solubility properties. The improved stability of the MP2H conjugates also allows for generation of higher final concentration therapeutic solutions, allowing for a larger drug load per dose.

TABLE 9

Increased Drug Valencies of Conjugates

| Protein | Linker | Intermediate | Conjugate | Protein conc before filtration (mg/mL) | Protein valency | Recovery upon 0.2 µm filtration | Conjugate Reaction Efficiency (including monomeric VHH) | Dissociation constant by BLI |
|---|---|---|---|---|---|---|---|---|
| aH aTNFa VHH | MP2H | 17 | 32 | 0.41 | 10 | 102% | 63% | 54.99 |
| aH aTNFa VHH | MP2H | 18 | 33 | 0.7 | 22 | 101% | 68% | 2.388 |
| aH aTNFa VHH | MP2H | 19 | 34 | 1.3 | 52 | 105% | 69% | 0.123 |
| aH aTNFa VHH | MP2H | 20 | 35 | 1.91 | 110 | 101% | 73% | <0.001 |
| aH aTNFa VHH | EMCH | 21 | 36 | 0.82 | 15 | 102% | 48% | 0.968 |
| aH aTNFa VHH | EMCH | 22 | 37 | 1.48 | 28 | 100% | 46% | 0.017 |
| aH aTNFa VHH | EMCH | 23 | 38 | 3.39 | 75 | 88% | 57% | <0.001 |
| aH aTNFa VHH | EMCH | 24 | 39* | 0.7 | | | | |

Reaction yield, filtration result and binding properties peptide polymer conjugates synthesized using MP2H or EMCH linkers with a range of maleimide and peptide valencies.
*denotes precipitated reaction Example 10. Intra-Articular Half-Life A well-known rat model was used for evaluating the clearance rate of proteins from joints to measure the IA half-life of Anti-TNF bioconjugates (Arthritis Rheum. 1999; 42(10):2094). For this assay, rats were anesthetized and the knees on their hind limbs prepared for sterile injection. Using a 30 G needle, an injection was made through synovial membrane of each knee joint, and a 40 μL injection of sterile, buffered was made into the synovial fluid. In each right knee, the injections also contained either an anti-inflammatory peptide, or an anti-inflammatory peptide at an equivalent concentration of total peptide. Generally, peptides used for this experiment have been tagged with near-infrared fluorophore (e.g., Alexa Fluor 750) using routine peptide tagging methods. At various time points for up to 10 days after the inject, the rats were imaged using an in vivo imaging system (e.g., Perkin Elmer IVIS Spectrum) to determine the intensity of fluorescence signal (e.g., average radiant efficiency) at the knees. Each left knee was used as a contralateral imaging control. Near infrared reporters can be detected in rat knees with high sensitivity using an in vivo imaging system which will enable detection down to picogram amounts of protein in the joint. The half-life of each treatment was determined following IA injection using established exponential decay calculations for optical in vivo imaging (Pharmaceutical research. 2013; 30(1):257). Therefore, the peptide concentration was used to estimate the intra-articular half-life of each peptide or conjugate within the joints after administration. The synovial fluid can be collected at the end of the experiment for proteomic analysis via mass spectroscopy to measure the final concentration of the peptides in the knee joint.

Prior to administration, peptides were tagged with Alexa Fluor 750 or alternate near-infrared fluorescent probe (ThermoFisher) following the manufacturers protocol. Briefly, peptides were mixed with Sulfo-Cy7 or AF750-NHS ester at a 2:1 ratio of probe:peptide. The probe was allowed to react with the peptides for 1 hour at room temperature, and then quenched with by adding 1 part 1.5M Tris to each 10 parts of reaction solution. The peptides were purified using NAP-10 desalting columns and eluting with PBS, pH 7.0.

Figures 6, 7:
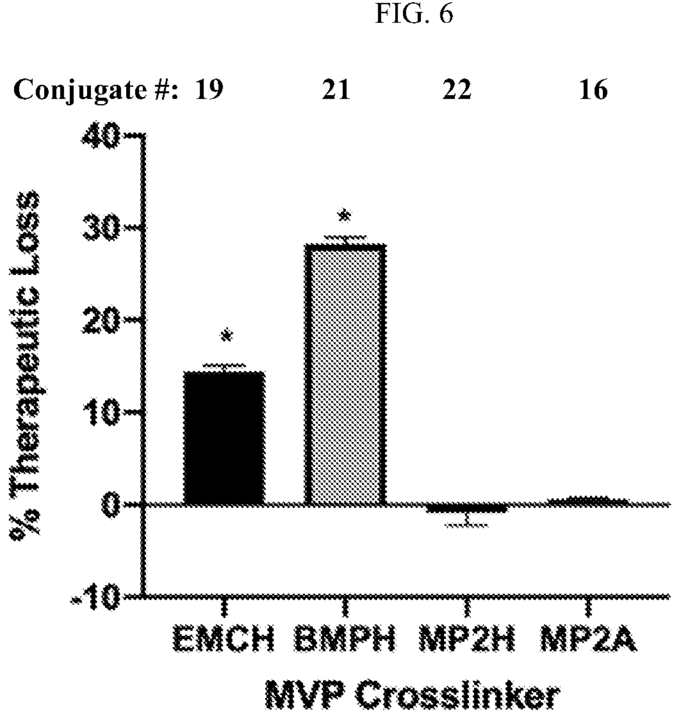
FIG. 6 shows a comparison of the amount of therapeutic protein loss after sterile (0.22.um) filtering anti-TNFa polymer conjugate 19, 21, 22, and 16 made using anti-TNFa VHH antibodies and various crosslinkers. EMCH and BMPH resulted in substantial conjugate loss during filtration whereas the loss for the maleimide PEG2 hydrazide (MP2H) and maleimide PEG2 amine (MP2A) linkers was negligible. *$p<0.001$ compared to zero, ANOVA with Tukey and n=4.
FIG. 7 shows a comparison of the intra-articular (IA) retention of anti-TNFa MVP made using anti-TNFa VHH antibodies and either EMCH or MP2H. Both MVPs had substantial increases in IA half-life compared to the unconjugated anti-TNFa VHH. The MVPs made with MP2H had a significantly longer intra-articular half-life compared to those made with EMCH (ANOVA with Tukey and n=4).
Figure 8A:
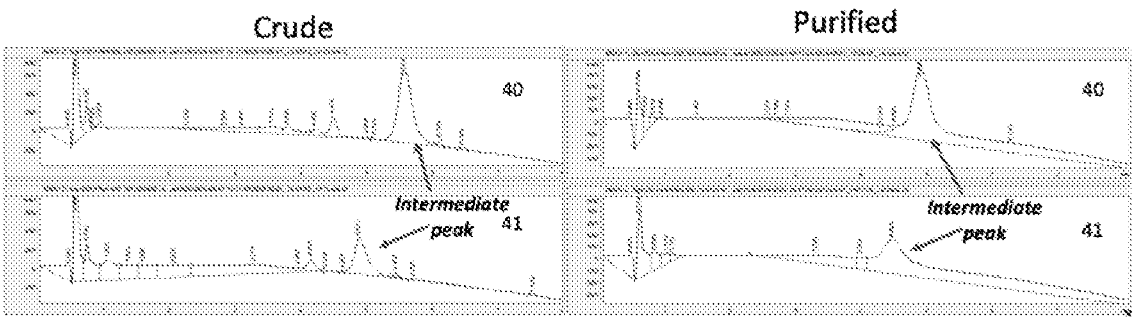
FIG. 8A and FIG. 8B each show Reverse Phase HPLC 230 and 254 nm traces showing the purification of intermediates 40 (EMCH, top) and 41 (MP2H, bottom) intermediate reaction products, crude (left) or purified (right) with a Zeba 7 kDa MWCO desalting column.
Figure 8B:
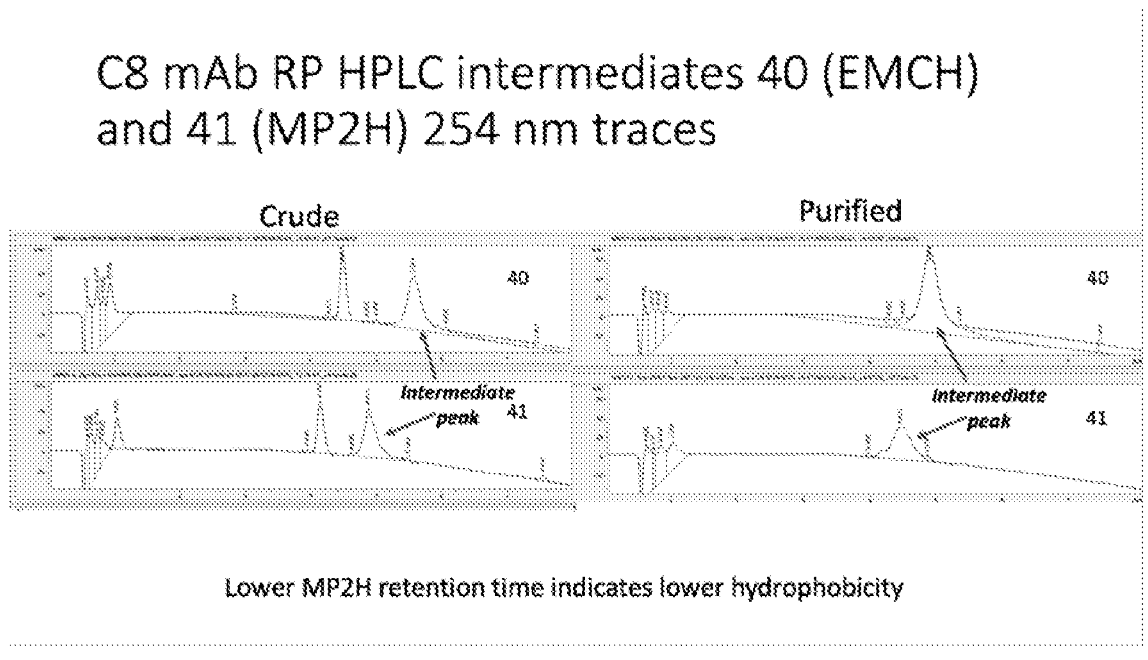
Figure 11:
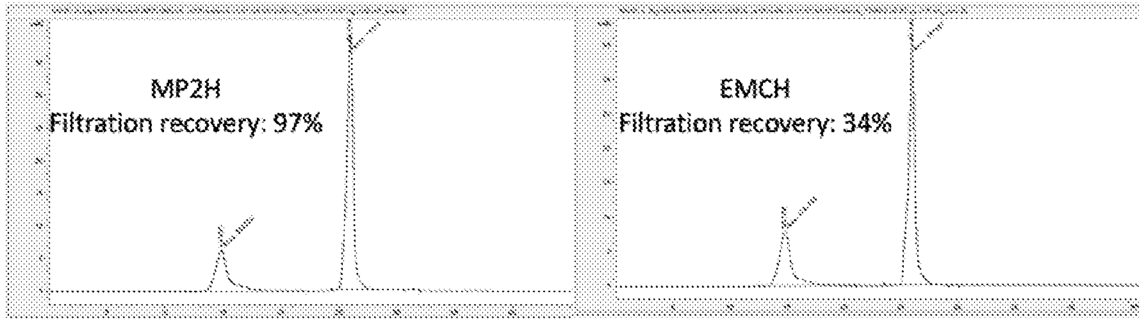
FIG. 11 shows HPLC SEC 280 nm traces for anti-VEGF G5-1 polymer conjugates 24 and 25 synthesized with 830 kDa HA intermediate consisting of either MP2H or EMCH linker and filtration recovery for the conjugates using a 0.2 μm filter.
Figure 12:
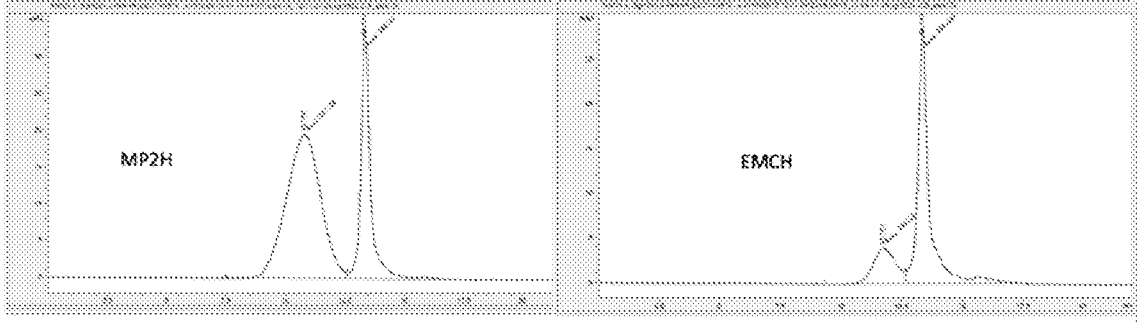
FIG. 12 shows HPLC SEC 280 nm traces for anti-VEGF DARPin conjugates 30 and 31 synthesized with 830 kDa HA intermediate consisting of either MP2H (30) or EMCH (31). EMCH linker shows lower reaction efficiency, size by retention time, and higher percent of unreacted DARPin compared to MP2H linker.
Figure 15A:
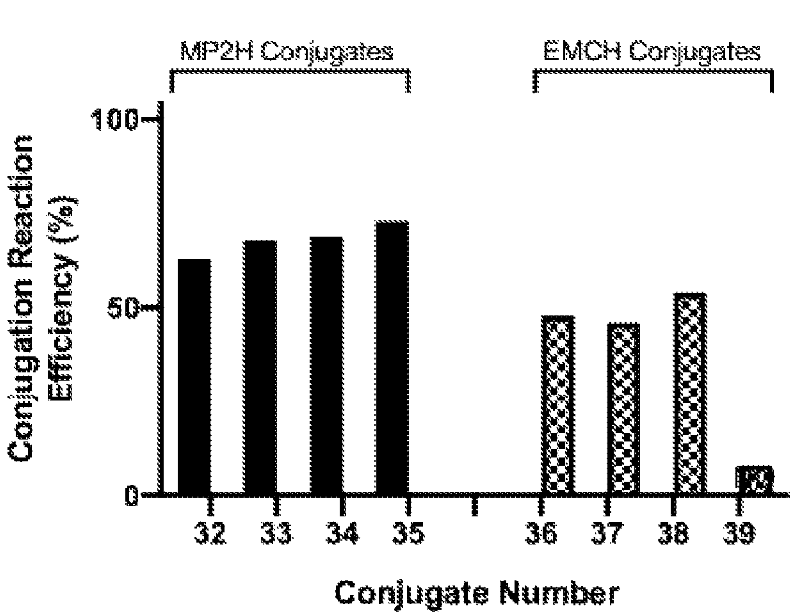
FIG. 15A and FIG. 15B show filtration recovery and reaction efficiency for MP2H (conjugates 32-35) or EMCH (conjugates 36-39) anti-TNFa-polymer conjugates synthesized at different potencies.
Figure 15B:
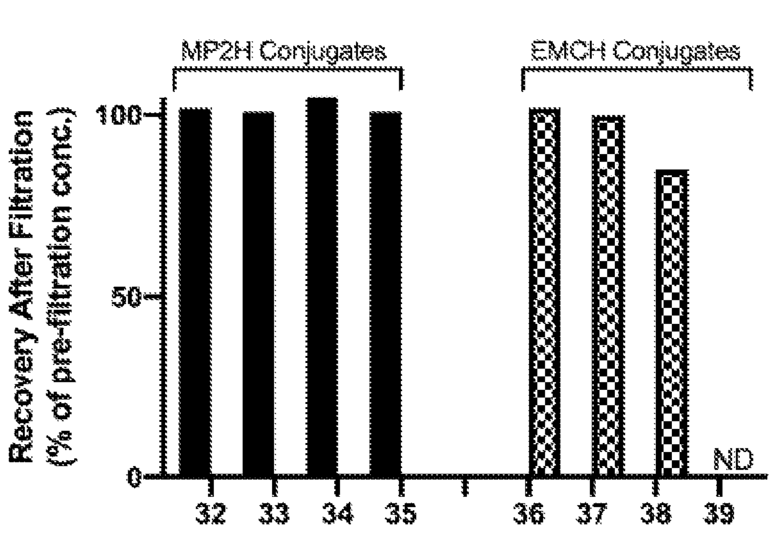
Figure 16:
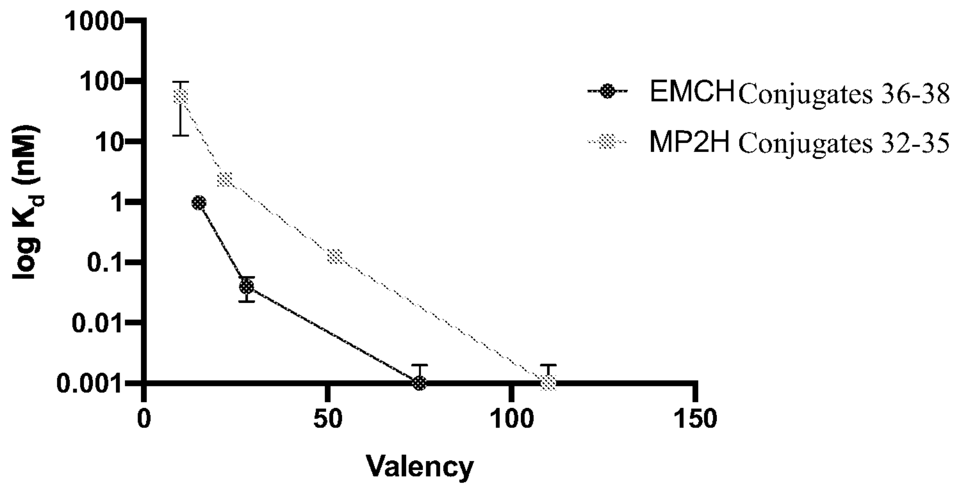
FIG. 16 shows binding kinetics for protein conjugates 32-35 (MP2H) or 36-38 (EMCH) anti-TNFa-polymer conjugates synthesized at different potencies. While EMCH showed higher binding affinity at lower valency vs MPH2, the EMCH conjugates were limited in the maximum achievable valency (precipitated above peptide valency of 75) and displayed lower reaction efficiency as well as poor handleability at higher peptide valencies. Kd of 0.001 indicates a read that is <LOD.

In one set of experiments (FIG. 7), the intra-articular half-life of anti-TNFα VHH antibodies (n=10) was compared to those of anti-inflammatory bioconjugates made from anti-TNFα VHH conjugated to 2000 kDA HyA with EMCH linker (n=4), and anti-TNFα VHH conjugated to 2000 kDA HyA with Mal-PEG2-hydrazide linker (n=4). The half-life of either bioconjugates made 2000 kDa HyA were significantly longer than the unconjugated VHH. In this experiment, the bioconjugates made with the Mal-PEG2-hydrazise linker exhibited approximately 30% longer retention time in the articular joint compared to the bioconjugates made with EMCH, despite both conjugates having the same size biopolymer component.

Example 11. Intravitreal Half-Life

A rabbit model can be used for determination of intravitreal half-life of the protein-polymer conjugates compared to unreacted peptide and analyzed via LCMS or radiant efficiency. For LCMS half life determination, animals received equimolar doses of either the peptide polymer conjugates or peptide alone by 50-μL intravitreal injections in each eye. On days 1, 4, 10, 20, 60 and 90, 3 rabbits were sacrificed from each group and enucleated eyes were prepared for LCMS quantitation of intravitreal peptide and conjugate concentrations after trypsin digestion. The LCMS concentration measurement method is not subject to interference by tissue sample matrix components and can quantify peptides in the tryptic digests unique to the anti-VEGF peptide down to 2 nM, which is sufficient to detect more than 10 intravitreal half-lives.

Figure 17:
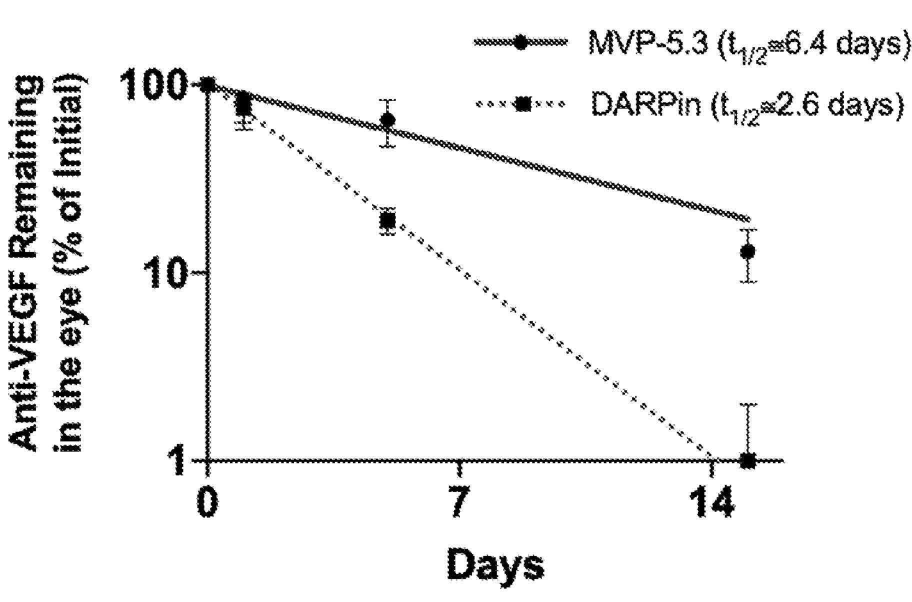
FIG. 17 shows intravitreal half-life of peptide protein conjugate 41 or peptide alone (DARPin).
Figure 19:
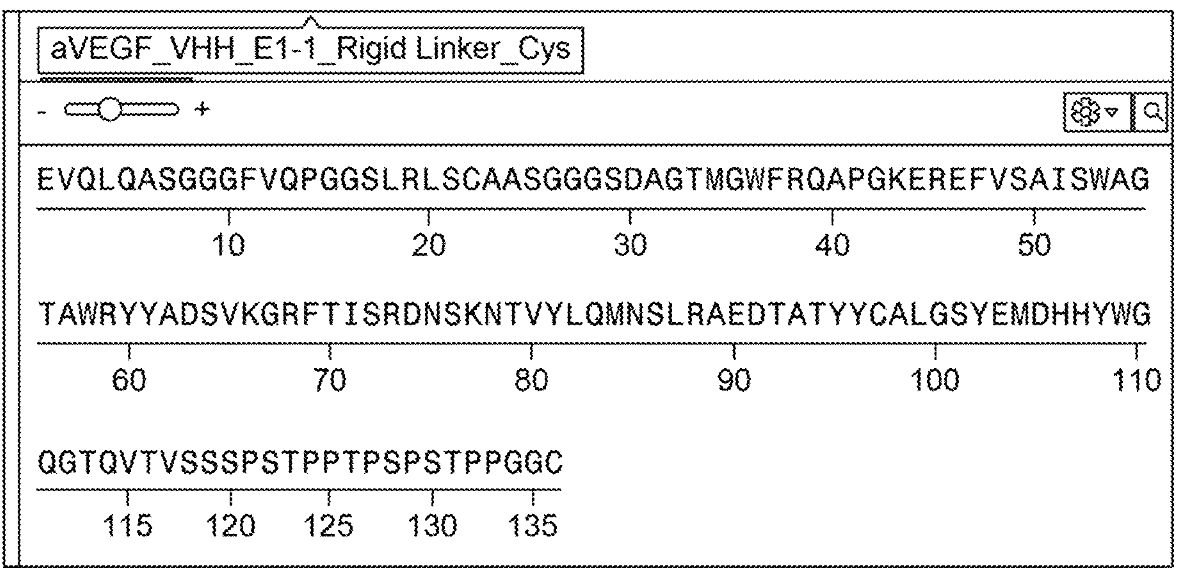
FIG. 19 shows an anti-VEGF VHH E1-1 sequence (SEQ ID NO: 18).
Figure 20:
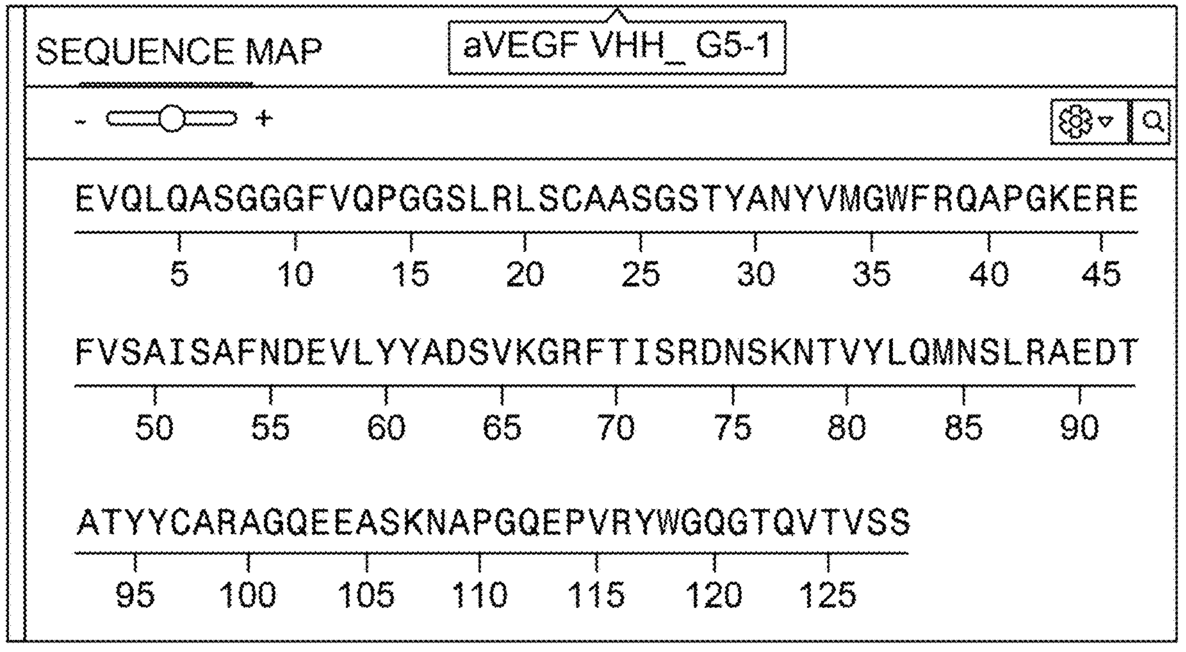
FIG. 20 shows an anti-VEGF VHH G5-1 sequence (SEQ ID NO: 19).

For generation of the data in FIG. 17, fluorescently tagged peptide or peptide protein conjugate were synthesized and administered intravitreally in rabbits to determine intravitreal half-life. Prior to administration, peptides were tagged with a near-infrared probe following the manufacturers protocol. Briefly, peptides were mixed with Sulfo-Cy7 or AF750-NHS ester at a 2:1 ratio of probe:peptide. The probe was allowed to react with the peptides for 1 hour at room temperature, and then quenched with by adding 1 part 1.5M Tris to each 10 parts of reaction solution. The peptides were purified using NAP-10 desalting columns and eluting with PBS, pH 7.0. Intravitreal injections of peptide or peptide polymer conjugate was injected into rabbit eyes at day 0. Rabbits were euthanized at noted times post intravitreal injection and the entire ocular globe was removed and snap frozen in liquid nitrogen. While frozen, the entire vitreous, retina and aqueous humor were dissected and placed into black 24 well plates. The Total Radiant Efficiency [p/s]/[μW/$cm^2$] of each individual tissue sample was imaged using an IVIS Spectrum imager (Perkin Elmer) with excitation/emission of 740/800 nm using tissue with 1 second exposure from uninjected control eyes as a blank. The intravitreal half-lives were then calculated using the total radiant efficiency linear regression analysis.

In this study it was observed that the peptide-polymer conjugates extend the intravitreal half live by two to three-fold compared to peptide alone. It has been demonstrated that for the protein polymer conjugate technology, higher valency results in higher bioactivity of the resulting molecule. Since the hydrophilic MP2H linker intermediates enable the synthesis of higher valency, higher concentration, better handling conjugates compared to EMCH and other hydrophobic linkers, the higher achievable valency of these conjugates will result in a maximum drug load to generate equivalent or greater bioactivity in vivo. The higher drug concentration allotted by the hydrophilic linkers will allow for higher doses achieve for the final drug product compared to the hydrophobic linkers. Additionally, hydrophobic linker-based conjugates used previously did not have the ability to be filtered for in vivo studies, so sterile processing methods had to be adopted to synthesize these conjugates. Sterile processing methods are timely and will not scale to large scale manufacturing processes, which will be required for clinical studies and drug manufacture.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

SEQUENCES (Anti-TNFa Single-Domain Heavy-chain (VHH) Antibody)

SEQ ID NO: 1

QVQLQESGGGLVQPGGSLRLSCAASGRTFSDHSGYTYTIGWFRQAPGKER

EFVARIYWSSGNTYYADSVKGRFAISRDIAKNTVDLTMNNLEPEDTAVYY

CAARDGIPTSRSVESYNYWGQGTQVTVSS (Anti-TNFa Single-Domain Heavy-chain (VHH) Antibody)

SEQ ID NO: 2

SNAQVQLQESGGGLVQPGGSLRLSCAASGRTFSDHSGYTYTIGWFRQAPGKER

EFVARIYWSSGNTYYADSVKGRFAISRDIAKNTVDLTMNNLEPEDTAVYY

CAARDGIPTSRSVESYNYWGQGTQVTVSSSPSTPPTPSPSTPPGGC

SEQ ID NO: 3

DHSGYTYTIG,

SEQ ID NO: 4

ARIYWSSGNTYYADSVKG

SEQ ID NO: 5

RDGIPT (Anti-TNFa Affibody)

SEQ ID NO: 6

SNACGGGVDN KFNKEVGWAF GEIGALPNLN ALQFRAFIIS LWDDPSQSAN 50

LLAEAKKLND AQAPK 65

(Anti-TNFa Single-Domain Heavy-chain (VHH) Antibody)

SEQ ID NO: 7

SNAQVQLQES GGGLVQPGGS LRLSCAASGR TFSDHSGYTY TIGWFRQAPG 50

KEREFVARIY WSSGNTYYAD SVKGRFAISR DIAKNTVDLT MNNLEPEDTA 100

VYYCAARDGI PTSRSVESYN YWGQGTQVTV SSSPSTPPTP SPSTPPGGCD 150

DDDKHHHHHH DYKDDDDK 168

(Anti-TNFa designed ankyrin repeat protein (DARPin))

SEQ ID NO: 8

SNADLGKKLL EVARAGQDDE VRILMANGAD VNAADHQSFT PLHLYAIFGH 50

LEIVEVLLKN GADVNASDWH GNTPLHLAAW IGHLEIVEVL LKYGADVNAT 100

DHSGSTPLHL AATLGHLEIV EVLLKYGADV NAQDKFGKTA FDISIDNGNE 150

DLAEILQKAA GGGSGGGSC 169

(Anti-IL-1B Single-Chain (scFv) Antibody)

SEQ ID NO: 9

SNAEIVMTQS PSTLSASVGD RVIITCQASQ SIDNWLSWYQ QKPGKAPKLL 50

IYRASTLASG VPSRFSGSGS GAEFTLTISS LQPDDFATYY CQNTGGGVSI 100

AFGQGTKLTV LGGGGGSGGG GSGGGGSGGG GSEVQLVESG GGLVQPGGSL 150

RLSCTASGFS LSSAAMAWVR QAPGKGLEWV GIIYDSASTY YASWAKGRFT 200

ISRDTSKNTV YLQMNSLRAE DTAVYYCARE RAIFSGDFVL WGQGTLVTVS 250

SSPSTPPTPS PSTPPGGC 268

(Soluble interleukin receptor 2 (sILR2))

SEQ ID NO: 10

HTGAARSCRF RGRHYKREFR LEGEPVALRC PQVPYWLWAS VSPRINLTWH 50

KNDSARTVPG EEETRMWAQD GALWLLPALQ EDSGTYVCTT RNASYCDKMS 100

IELRVFENTD AFLPFISYPQ ILTLSTSGVL VCPDLSEFTR DKTDVKIQWY 150

KDSLLLDKDN EKFLSVRGTT HLLVHDVALE DAGYYRCVLT FAHEGQQYNI 200

TRSIELRIKK KKEETIPVII SPLKTISASL GSRLTIPCKV FLGTGTPLTT 250

MLWWTANDTH IESAYPGGRV TEGPRQEYSE NNENYIEVPL IFDPVTREDL 300

HMDFKCVVHN TLSFQTLRTT VKESPSTPPT PSPSTPPGGC 340

-continued

Anti-(mouse)TNFa Single-Domain Heavy-chain (VHH) Antibody

SEQ ID NO: 11

SNAQVQLQDS GGGLVQAGGS LRLSCAASGG TFSSIIMAWF RQAPGKEREF 50

VGAVSWSGGT TVYADSVLGR FEISRDSARK SVYLQMNSLK PEDTAVYYCA 100

ARPYQKYNWA SASYNVWGQG TQVTVSSSPS TPPTPSPSTP PGGCDDDDKH 150

HHHHH 155

SEQ ID NO: 12

26 qsklk dpelslkgtq himqagqtlh lqcrgeaahk 61 wslpemvske serlsitksa cgrngkqfcs tltlntaqan htgfysckyl avptskkket 121 asaiyifisd tgrpfvemys eipeithmte grelvipcrv tspnitvtlk kfpldtlipd 181 gkriiwdsrk gfiisnatyk eiglltceat vnghlyktny lthrqtntii dvqistprpv 241 kllrghtlvl nctattplnt rvqmtwsypd eknkrasvrr ridqsnshan ifysvltidk 301 mqnkdkglyt crvrsgpsfk svntsvhiyd kafitvkhrk qqvletvagk rsyrlsmkvk 361 afpspevvwl kdglpateks aryltrgysl iikdvteeda gnytillsik qsnvfknlta 421 tlivnvkpqi yekavssfpd palyplgarq iltctaygip qptikwfwhp cnhnhaearc 481 dfcsnneesf ildadsnmgn riesitqrma iiegknkmas tlvvadsris giyiciasnk 541 vgtvgrnisf yitdvpngfh vnlekmpteg edlklsctvn kflyrdvtwi llrtvnnrtm 601 hysiskqkma itkehsitln ltimnvslqd sgtyacrarn vytgeeilqk keitirdqea 661 pyllrnlsdh tvaisssttl dchangvpep qitwfknnhk iqqepgiilg pgsstlfier 721 vleedegvyh ckatnqkgsv essayltvqg tsdksnlell tltctcvaal lfwllltlfi

SEQ ID NO: 13

26 gsklk cpelslkgtq himqagqtlh lqcrgeaahk 61 wslpervske serlsitksa cgrngkqfcs tltlntaqan htgfysckyl avptskkket 121 esaiyifisd tgrpfvemys eipeiihmte grelvipcrv tspnitvtlk kfpldtlipd 181 qkriiwdsrk qfiisnatyk eiqlltceat vnghlyktny lthrqtntii dvqistprpv 241 kllrghtlvl nctattplrt rvqmtwsypd eknkrasvrr ridqsnshan ifysvltidk 301 mqnkdkglyt crvrsgpsfk svntsvhi

SEQ ID NO: 14

142 jpeiihmte grelvipcrv tspnitvtlk kfpldtlipd 181 gkriiwdsrk gfiisnatyk eiglltceat vnghlyktny lthrqtntii dvqistprpv 241 kllrghtlvl nctattplnt rvqmtwsypd eknkrasvrr ridqsnshan ifysvltidk 301 mqnkdkglyt crvrsgpsfk svntsvhi sFlt sequence

SEQ ID NO: 15

MVSYWDTGVLLCALLSCLLLTGSSSGSKLKDPELSLKGTQHIMQAGQTLHLQCRGEAAHKWSLPEMV

SKESERLSITKSACGRNGKQFCSTLTLNTAQANHTGFYSCKYLAVPTSKKKETESAIYIFISDTGRP

FVEMYSEIPEIIHMTEGRELVIPCRVTSPNITVTLKKFPLDTLIPDGKRIIWDSRKGFIISNATYKE

IGLLTCEATVNGHLYKTNYLTHRQTNTIIDVQISTPRPVKLLRGHTLVLNCTATTPLNTRVQMTWSY

PDEKNKRASVRRRIDQSNSHANIFYSVLTIDKMQNKDKGLYTCRVRSGPSFKSVNTSVHIYDKAFIT

VKHCDDDDKHHHHHH scFv anti-VEGF antibody

SEQ ID NO: 16

MEIVMTQGPS TLSASVGDRV IITCQASEII HSVLAWYQQK PGKAPKLLQY 50

LASTLASGVP SRFSGSGSGA EFTLTISSLQ PDDFATTYCQ NVYLASTNGA 100

NFGQGTKLTV LGGGGGSGGG GSGGGGSGGG GSEVQLVESG GGLVQPGGSL 150

-continued

```
NLSCTASGFS LTDYYYMTWV KQAPGKGLEW VGFLDPDDDP YYATWAKGRF 200

TISRDNSKNT LYLQMNSLRA EDTAVYYCAG GDHNSGNGLD IWGQGTLVTV 250

SSSPSTPPTP SPSTPPGGCD DDDKHHHHHH                      280
```

anti-VEGF VHH

SEQ ID NO: 17

```
SNADVQLVES GGGLVQPGGS LRLSCAASGR TFSSYSMGNF RQAPGKEREF  50

VVAISKGGYK YDAVSLEGRF TISRDNAKNT VYLQINSLRP EDTAVYYCAS 100

SRAYGSSRLR LADTYEYNGQ GTLVTVSSSP STPPTPSPST PPGGCDDDDK 150

HHHHHH                                                156
```

natriuretic peptide C-type

SEQ ID NO: 20

Gly-Leu-Ser-Lys-Gly-Cys-Phe-Gly-Leu-Lys-Leu-Asp-Arg-Ile-Gly-Ser-

Met-Ser-Gly-Leu-Gly-Cys [Disulfide Bridge: 6-22]

anti-VEGF DARPin

SEQ ID NO: 21

```
SNAGSDLDKKLLEAARAGQDDEVRILMANGADVNARDSTGWTPLHLAAPWGHPEI

VEVLLKNGADVNAADFQGWTPLHLAAAVGHLEIVEVLLKYGADVNAQDKFGKTAF

DISIDNGNEDLAEILQKAAGGGSGGGSC
```

---

What is claimed is:

1. A conjugate of Formula I:

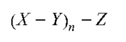

$$(X-Y)_n-Z \quad \text{Formula (I)}$$

wherein each X is independently a peptide, wherein the peptide is an antibody or a DARPin;

each Y is independently a hydrophilic linker, wherein the hydrophilic linker corresponds to any one of the following:

1-[3-({[2-(3-Hydrazino-3-oxopropoxy)ethoxy]methyl}amino)-3-oxopropyl]-1H-pyrrole-2,5-dione, 1-(3-{2-[2-(3-Hydrazino-3-oxopropoxy)ethoxy]ethylamino}-3-oxopropyl)-1H-pyrrole-2,5-dione, or 1-[3-(2-{2-[2-(2-Aminoethoxy)ethoxy]ethoxy}ethylamino)-3-oxopropyl]-1H-pyrrole-2,5-dione;

Z is a biocompatible polymer having a molecular weight of from about 0.8 MDa to about 3 MDa, wherein the biocompatible polymer is hyaluronic acid; and subscript n is an integer from 10 to 1000.

2. The conjugate of claim 1, wherein the peptide is an inhibitor of angiogenesis.

3. The conjugate of claim 2, wherein the peptide is an antibody specific for VEGF- or a DARPin specific for VEGF.

4. The conjugate of claim 2, wherein the peptide inhibits VEGF-A, VEGF-B, VEGF-C, VEGF-D, Ang-1, Ang-2, PDGF, or PlGF.

5. The conjugate of claim 2, wherein the peptide is a monoclonal IgG antibody, an IgG antibody fragment, a single-chain variable region antibody, a single-domain heavy chain antibody, or a DARPin.

6. The conjugate of claim 1, wherein the peptide modulates the activity of immune cell function.

7. The conjugate of claim 6, wherein the peptide inhibits tumor necrosis factor-α.

8. The conjugate of claim 6, wherein the peptide is a monoclonal IgG antibody, an IgG antibody fragment, a single-chain variable region antibody, a single-domain heavy chain antibody, or a DARPin.

9. The conjugate of claim 6, wherein the peptide has an amino acid sequence selected from the group consisting of SEQ ID NO:1, SEQ ID NO:2, SEQ ID NO:6, SEQ ID NO:7, SEQ ID NO:8, SEQ ID NO:9, and SEQ ID NO:10.

10. The conjugate of claim 6, wherein the peptide has a sequence:

(SEQ ID NO: 1)
QVQLQESGGGLVQPGGSLRLSCAASGRTFSDHSGYTYTIGWFRQAPGKER
EFVARIYWSSGNTYYADSVKGRFAISRDIAKNTVDLTMNNLEPEDTAVYY
CAARDGIPTSRSVESYNYWGQGTQVTVSS.

11. The conjugate of claim 1, wherein the biocompatible polymer has a molecular weight of about 0.9 MDa.

12. The conjugate of claim 1, wherein the biocompatible polymer has a molecular weight of about 2 MDa.

13. The conjugate of claim 1, wherein subscript n is an integer of from 10 to 400.

14. The conjugate of claim 1, wherein subscript n is an integer of from 10 to 100.

15. The conjugate of claim 1, wherein subscript n is an integer of from 50 to 100.

16. A pharmaceutical composition comprising the conjugate of claim 1, and a pharmaceutically acceptable carrier.

17. The conjugate of claim 1, wherein the hydrophilic linker corresponds to 1-(3-{2-[2-(3-Hydrazino-3-oxo-propoxy)ethoxy]ethylamino}-3-oxopropyl)-1H-pyrrole-2,5-dione.

18. The conjugate of claim 1, wherein the hydrophilic linker is

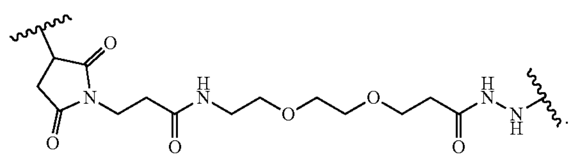 [SMILES: *NNC(=O)CCOCCOCCNC(=O)CCN1C(=O)CC(*)C1=O]

* * * * *